US007547551B2

(12) United States Patent
Schuler et al.

(10) Patent No.: US 7,547,551 B2
(45) Date of Patent: Jun. 16, 2009

(54) TRANSFECTION OF EUKARYONTIC CELLS WITH LINEAR POLYNUCLEOTIDES BY ELECTROPORATION

(75) Inventors: Gerold Schuler, Am Veilchenberg 25, 91080 Spardorf (DE); Zwi N. Berneman, Antwerpen (BE); Viggo F. I. Van Tendeloo, Lier (BE); Peter Ponsaerts, Deurne (BE); Isolde Strobel, Hartmannstr. 14, 91052, Erlangen (DE)

(73) Assignees: University of Antwerp., Antwerp (BE); Gerold Schuler, Spardorf (DE); Isolde Strobel, Erlangen (DE)

( * ) Notice: Subject to any disclaimer, the term of this patent is extended or adjusted under 35 U.S.C. 154(b) by 696 days.

(21) Appl. No.: 10/177,390

(22) Filed: Jun. 20, 2002

(65) Prior Publication Data

US 2003/0143743 A1 Jul. 31, 2003

Related U.S. Application Data

(60) Provisional application No. 60/299,817, filed on Jun. 21, 2001.

(51) Int. Cl.
*C12N 15/87* (2006.01)
(52) U.S. Cl. .................. 435/461; 435/366; 435/372
(58) Field of Classification Search ............... 536/23.1; 435/325, 461
See application file for complete search history.

(56) References Cited

U.S. PATENT DOCUMENTS 4,956,288 A * 9/1990 Barsoum .................. 435/6
5,554,528 A * 9/1996 Harrison et al. .......... 435/372.3
5,877,396 A * 3/1999 Ravetch et al. ............ 800/3

FOREIGN PATENT DOCUMENTS

EP 0 414 551 A2 2/1991
JP 03 164187 7/1991

OTHER PUBLICATIONS

Lieber et al. Stable High-Level Gene Expression in Mammalian Cells by T7 Phage Polymerase, 1993, Methods in Enzymology, vol. 217, pp. 47-66.*

Elliot et al, green Fluoresecent Protein: A Novel Viability Assay for Cryobiologival Applications, 2000, Cryobiology, vol. 40, pp. 360-369.*
Current Protocols in Cell Biology pp. 20.5.1-20.5.2 (2003).*
Pusch et al. Two open states and rate limiting gating steps revealed by intra cellular Na block of human KcnQ1 and KCNQ1/KCNE k Channels J. of Physiology 533.1 pp. 135-144 2001.*
EasyJecT Plus specifications form Wolf Laboratories Ltd, UK, printed Apr. 15, 2005.*
Arthur et al. "A comparison of gene transfer methods in human dendritic cells." *Cancer Gene Ther* 1997; 4: 17-25. Abstract provided.
Lea et al. "High efficiency protein transduction of quiescent and proliferating primary hematopoietic cells." *J. Biochem Biophys Methods*. 2003; 55(3): 251-8. Abstract provided.
Van Tendeloo et al. "Nonviral transfection of distinct types of human dendritic cells: high-efficiency gene transfer by electroporation into hematopoietic progenitor- but not monocyte-derived dendritic cells." *Gene Ther* 1998; 5(5): 700-7. Abstract provided.
Wessinger et al. "Gene transfer in purified human hematopoietic peripheral-blood stem cells by means of electroporation without prestimulation." *J. Lab Clin Med* 2003; 141(2): 138-49. Abstract provided.
Ebert et al. "Lymphocyte apoptosis: induction by gene transfer techniques." *Gene Ther* 1997; 4(4): 296-302. Abstract provided.
Strobel et al., *Gene Ther* 2000, 7(23): 2028-35. Abstract provided.
Watkins et al., *Vet Immunol. Immunopathol*., 1999, 72(1-2): 125-33. Abstract provided.
Lohman et al., *Cancer Gene Ther* 2000, 7(4): 605-14. Abstract provided.
Nucleic Acid V—Cell Engineering, 1st edition, 1st printing, published Sep. 6, 1993, Published by Tokyo Kagaku Dozin Co., Ltd.
Strobel, et al; "Human dendritic cells transfected with either RNA or DNA encoding influenza matrix protein M1 differ in their ability to stimulate cytotoxic T lymphocytes"; Gene Therapy (2000) 7, pp. 2028-2035.

* cited by examiner

*Primary Examiner*—James S Ketter
(74) *Attorney, Agent, or Firm*—Norris McLaughlin & Marcus PA

(57) ABSTRACT

The present invention provides an improved method for gene delivery in eukaryotic cells by electroporation, preferably in human hematopoietic cells, particular dendritic cells. The method of the invention is superior to lipofection and passive pulsing of mRNA and to electroporation of plasmid cDNA for gene delivery, including tumor antigen loading of dendritic cells.

17 Claims, 51 Drawing Sheets

— control
— mRNA
-- DNA

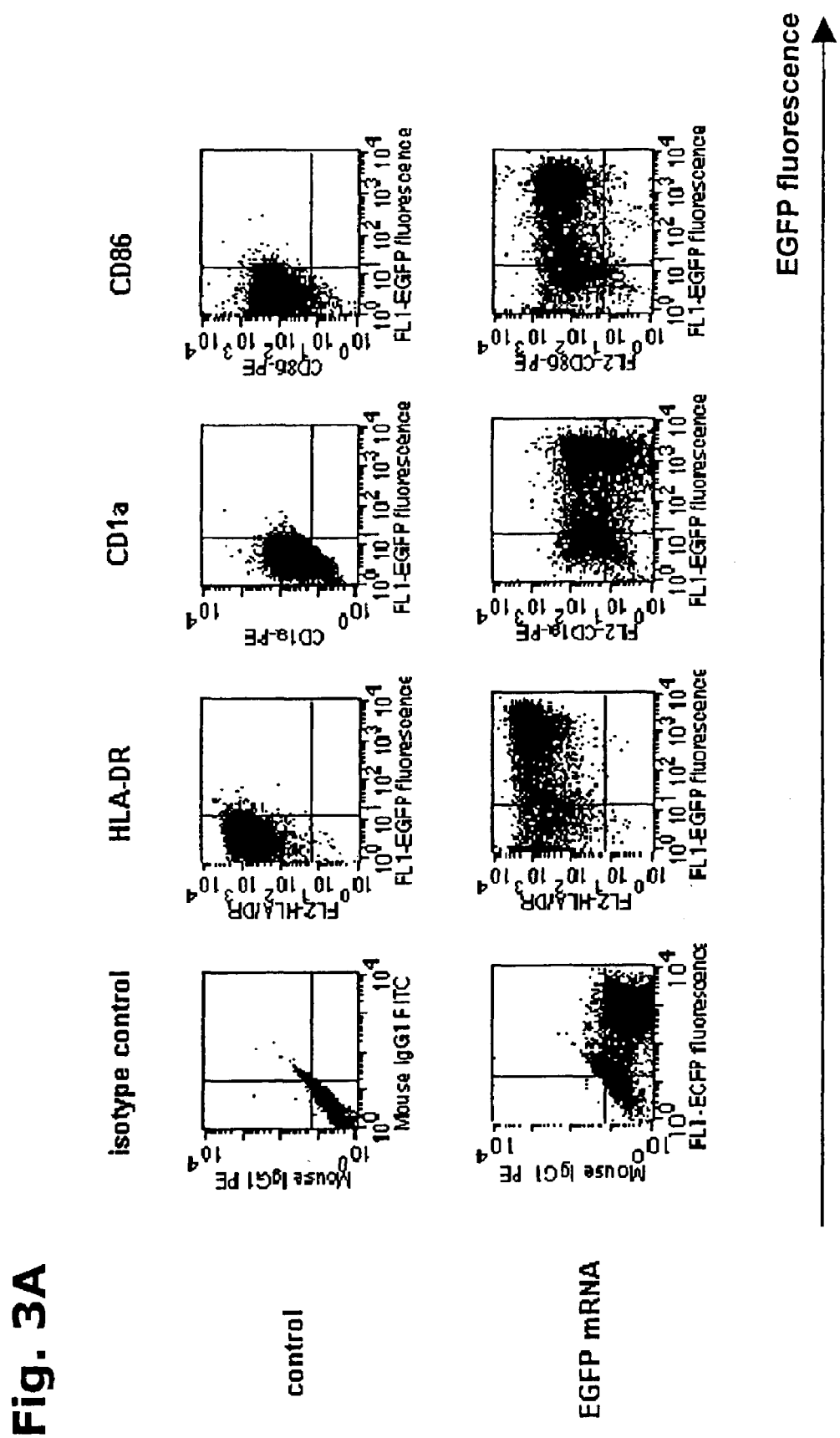

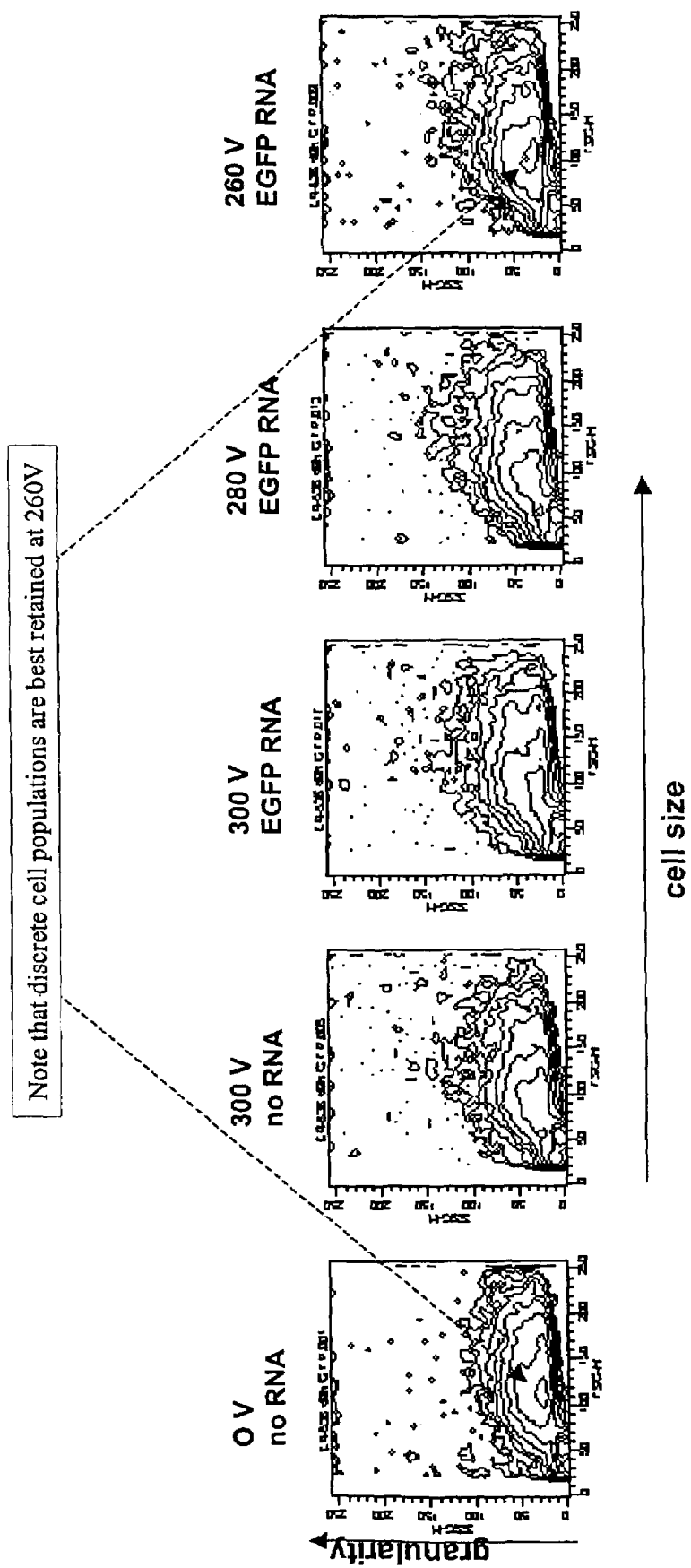

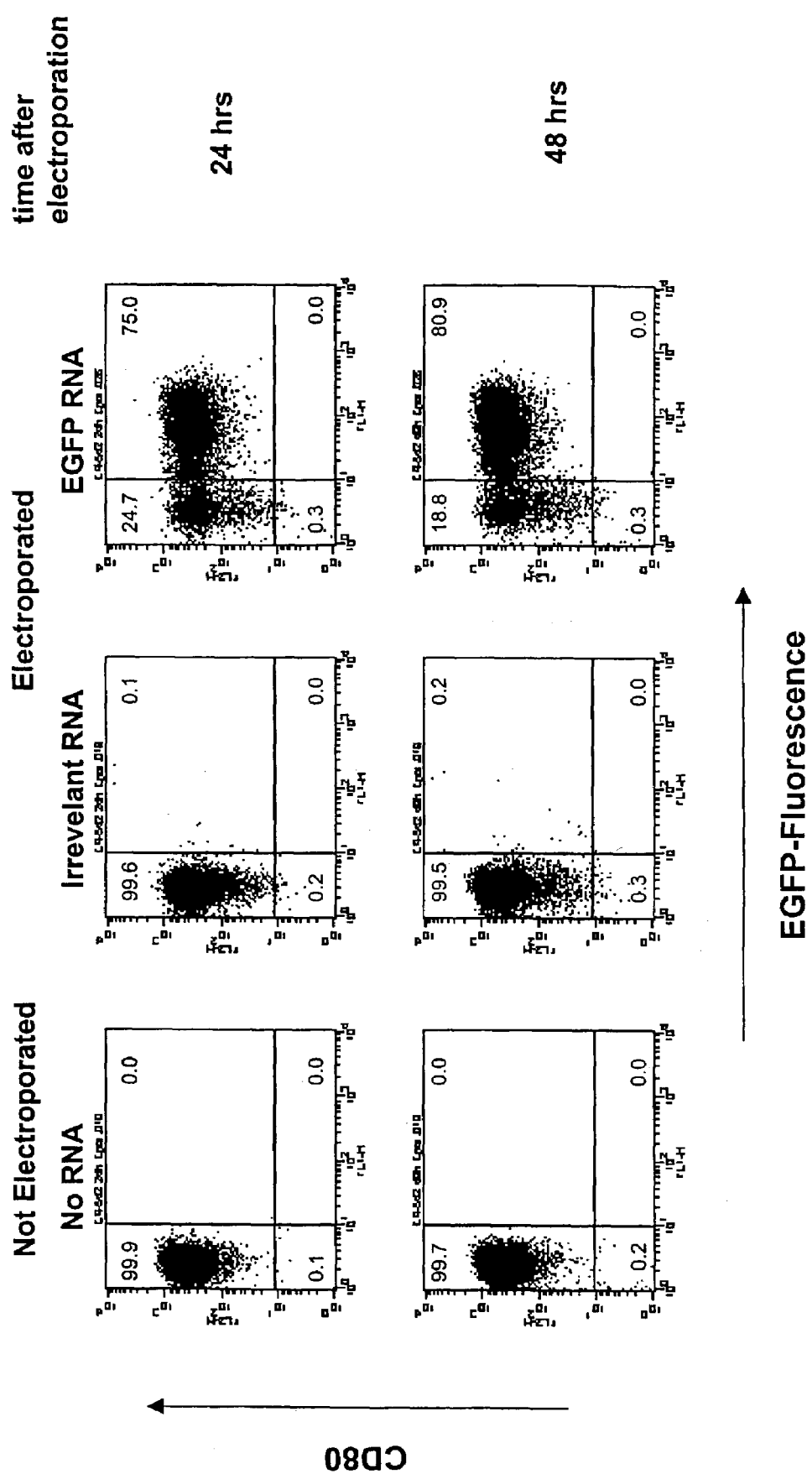

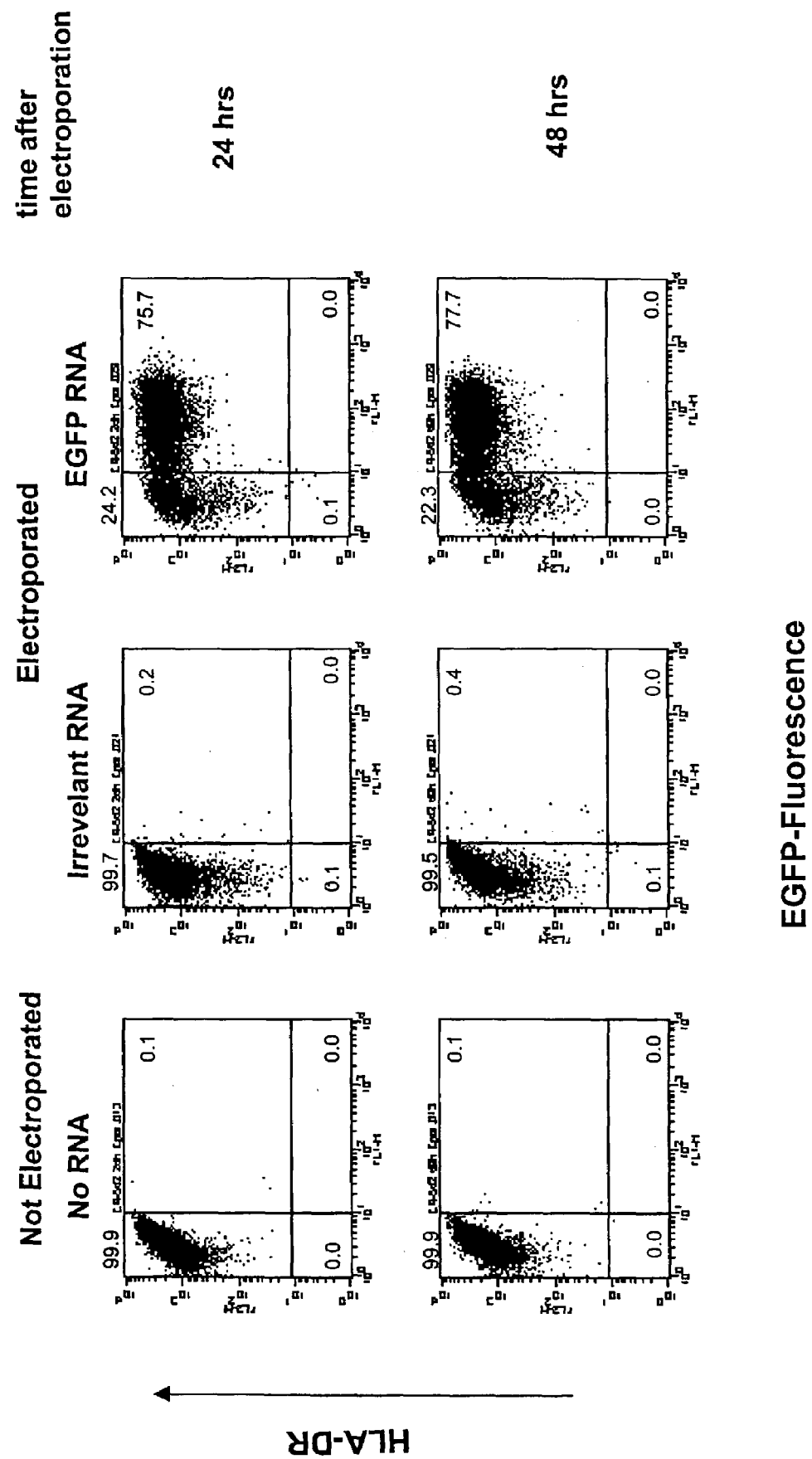

SEQUENCE LISTING

```
<160> NUMBER OF SEQ ID NOS: 34

<210> SEQ ID NO 1
<211> LENGTH: 4733
<212> TYPE: DNA
<213> ORGANISM: Artificial Sequence
<220> FEATURE:
<223> OTHER INFORMATION: Description of Artificial Sequence: pEGFP-N1
      cloning vector (Clonetech)
<220> FEATURE:
<221> NAME/KEY: CDS
<222> LOCATION: (679)..(1395)

<400> SEQUENCE: 1
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
```

-continued

```
acggtgggag gtctatataa gcagagctgg tttagtgaac cgtcagatcc gctagcgcta    600
ccggactcag atctcgagct caagcttcga attctgcagt cgacggtacc gcgggcccgg    660
gatccaccgg tcgccacc atg gtg agc aag ggc gag gag ctg ttc acc ggg      711
                    Met Val Ser Lys Gly Glu Glu Leu Phe Thr Gly
                     1               5                  10 gtg gtg ccc atc ctg gtc gag ctg gac ggc gac gta aac ggc cac aag      759
Val Val Pro Ile Leu Val Glu Leu Asp Gly Asp Val Asn Gly His Lys
             15                  20                  25 ttc agc gtg tcc ggc gag ggc gag ggc gat gcc acc tac ggc aag ctg      807
Phe Ser Val Ser Gly Glu Gly Glu Gly Asp Ala Thr Tyr Gly Lys Leu
         30                  35                  40 acc ctg aag ttc atc tgc acc acc ggc aag ctg ccc gtg ccc tgg ccc      855
Thr Leu Lys Phe Ile Cys Thr Thr Gly Lys Leu Pro Val Pro Trp Pro
     45                  50                  55 acc ctc gtg acc acc ctg acc tac ggc gtg cag tgc ttc agc cgc tac      903
Thr Leu Val Thr Thr Leu Thr Tyr Gly Val Gln Cys Phe Ser Arg Tyr
 60                  65                  70                  75 ccc gac cac atg aag cag cac gac ttc ttc aag tcc gcc atg ccc gaa      951
Pro Asp His Met Lys Gln His Asp Phe Phe Lys Ser Ala Met Pro Glu
                 80                  85                  90 ggc tac gtc cag gag cgc acc atc ttc ttc aag gac gac ggc aac tac      999
Gly Tyr Val Gln Glu Arg Thr Ile Phe Phe Lys Asp Asp Gly Asn Tyr
             95                 100                 105 aag acc cgc gcc gag gtg aag ttc gag ggc gac acc ctg gtg aac cgc     1047
Lys Thr Arg Ala Glu Val Lys Phe Glu Gly Asp Thr Leu Val Asn Arg
         110                 115                 120 atc gag ctg aag ggc atc gac ttc aag gag gac ggc aac atc ctg ggg     1095
Ile Glu Leu Lys Gly Ile Asp Phe Lys Glu Asp Gly Asn Ile Leu Gly
     125                 130                 135 cac aag ctg gag tac aac tac aac agc cac aac gtc tat atc atg gcc     1143
His Lys Leu Glu Tyr Asn Tyr Asn Ser His Asn Val Tyr Ile Met Ala
140                 145                 150                 155 gac aag cag aag aac ggc atc aag gtg aac ttc aag atc cgc cac aac     1191
Asp Lys Gln Lys Asn Gly Ile Lys Val Asn Phe Lys Ile Arg His Asn
                 160                 165                 170 atc gag gac ggc agc gtg cag ctc gcc gac cac tac cag cag aac acc     1239
Ile Glu Asp Gly Ser Val Gln Leu Ala Asp His Tyr Gln Gln Asn Thr
             175                 180                 185 ccc atc ggc gac ggc ccc gtg ctg ctg ccc gac aac cac tac ctg agc     1287
Pro Ile Gly Asp Gly Pro Val Leu Leu Pro Asp Asn His Tyr Leu Ser
         190                 195                 200 acc cag tcc gcc ctg agc aaa gac ccc aac gag aag cgc gat cac atg     1335
Thr Gln Ser Ala Leu Ser Lys Asp Pro Asn Glu Lys Arg Asp His Met
     205                 210                 215 gtc ctg ctg gag ttc gtg acc gcc gcc ggg atc act ctc ggc atg gac     1383
Val Leu Leu Glu Phe Val Thr Ala Ala Gly Ile Thr Leu Gly Met Asp
220                 225                 230                 235 gag ctg tac aag taaagcggcc gcgactctag atcataatca gccataccac         1435
Glu Leu Tyr Lys atttgtagag gttttacttg ctttaaaaaa cctcccacac ctcccctga acctgaaaca    1495 taaaatgaat gcaattgttg ttgttaactt gtttattgca gcttataatg gttacaaata   1555
aagcaatagc atcacaaatt tcacaaataa agcattttt tcactgcatt ctagttgtgg    1615
tttgtccaaa ctcatcaatg tatcttaagg cgtaaattgt aagcgttaat attttgttaa   1675
aattcgcgtt aaattttgt taatcagct cattttttaa ccaataggcc gaaatcggca    1735 aaatcccta taaatcaaaa gaatagaccg agatagggtt gagtgttgtt ccagtttgga   1795
```

```
acaagagtcc actattaaag aacgtggact ccaacgtcaa agggcgaaaa accgtctatc    1855
agggcgatgg cccactacgt gaaccatcac cctaatcaag ttttttgggg tcgaggtgcc    1915
gtaaagcact aaatcggaac cctaaaggga gcccccgatt tagagcttga cggggaaagc    1975
cggcgaacgt ggcgagaaag gaagggaaga aagcgaaagg agcgggcgct agggcgctgg    2035
caagtgtagc ggtcacgctg cgcgtaacca ccacacccgc cgcgcttaat gcgccgctac    2095
agggcgcgtc aggtggcact tttcggggaa atgtgcgcgg aacccctatt tgtttatttt    2155
tctaaataca ttcaaatatg tatccgctca tgagacaata accctgataa atgcttcaat    2215
aatattgaaa aaggaagagt cctgaggcgg aaagaaccaa ctgtggaatg tgtgtcagtt    2275
agggtgtgga agtccccag gctccccagc aggcagaagt atgcaaagca tgcatctcaa    2335
ttagtcagca accaggtgtg aaagtcccc aggctcccca gcaggcagaa gtatgcaaag    2395
catgcatctc aattagtcag caaccatagt cccgcccta actccgccca tcccgcccct    2455
aactccgccc agttccgccc attctccgcc ccatggctga ctaattttt ttatttatgc    2515
agaggccgag gccgcctcgg cctctgagct attccagaag tagtgaggag gctttttgg    2575
aggcctaggc ttttgcaaag atcgatcaag agacaggatg aggatcgttt cgcatgattg    2635
aacaagatgg attgcacgca ggttctccgg ccgcttgggt ggagaggcta ttcggctatg    2695
actgggcaca acagacaatc ggctgctctg atgccgccgt gttccggctg tcagcgcagg    2755
ggcgcccggt tctttttgtc aagaccgacc tgtccggtgc cctgaatgaa ctgcaagacg    2815
aggcagcgcg gctatcgtgg ctggccacga cgggcgttcc ttgcgcagct gtgctcgacg    2875
ttgtcactga agcgggaagg gactggctgc tattgggcga agtgccgggg caggatctcc    2935
tgtcatctca ccttgctcct gccgagaaag tatccatcat ggctgatgca atgcggcggc    2995
tgcatacgct tgatccggct acctgcccat tcgaccacca agcgaaacat cgcatcgagc    3055
gagcacgtac tcggatggaa gccggtcttg tcgatcagga tgatctggac gaagagcatc    3115
aggggctcgc gccagccgaa ctgttcgcca ggctcaaggc gagcatgccc gacggcgagg    3175
atctcgtcgt gacccatggc gatgcctgct tgccgaatat catggtggaa aatggccgct    3235
tttctggatt catcgactgt ggccggctgg gtgtggcgga ccgctatcag gacatagcgt    3295
tggctacccg tgatattgct gaagagcttg gcggcgaatg ggctgaccgc ttcctcgtgc    3355
tttacggtat cgccgctccc gattcgcagc gcatcgcctt ctatcgcctt cttgacgagt    3415
tcttctgagc gggactctgg ggttcgaaat gaccgaccaa gcgacgccca acctgccatc    3475
acgagatttc gattccaccg ccgccttcta tgaaaggttg gcttcggaa tcgttttccg    3535
ggacgccggc tggatgatcc tccagcgcgg ggatctcatg ctggagttct cgcccaccc    3595
taggggagg ctaactgaaa cacggaagga gacaataccg gaaggaaccc gcgctatgac    3655
ggcaataaaa agacagaata aaacgcacgg tgttgggtcg tttgttcata acgcggggt    3715
tcggtcccag ggctggcact ctgtcgatac cccaccgaga ccccattggg gccaatacgc    3775
ccgcgtttct tccttttccc caccccaccc cccaagttcg ggtgaaggcc cagggctcgc    3835
agccaacgtc ggggcggcag gccctgccat agcctcaggt tactcatata actttttagat    3895
tgatttaaaa cttcattttt aatttaaaag gatctaggtg aagatccttt ttgataatct    3955
catgaccaaa atcccttaac gtgagttttc gttccactga gcgtcagacc ccgtagaaaa    4015
gatcaaagga tcttcttgag atcctttttt tctgcgcgta atctgctgct tgcaaacaaa    4075
aaaaccaccg ctaccagcgg tggtttgttt gccggatcaa gagctaccaa ctctttttcc    4135
gaaggtaact ggcttcagca gagcgcagat accaaatact gtccttctag tgtagccgta    4195
```

```
gttaggccac cacttcaaga actctgtagc accgcctaca tacctcgctc tgctaatcct   4255
gttaccagtg gctgctgcca gtggcgataa gtcgtgtctt accgggttgg actcaagacg   4315
atagttaccg gataaggcgc agcggtcggg ctgaacgggg ggttcgtgca cacagcccag   4375
cttggagcga acgacctaca ccgaactgag atacctacag cgtgagctat gagaaagcgc   4435
cacgcttccc gaagggagaa aggcggacag gtatccggta agcggcaggg tcggaacagg   4495
agagcgcacg agggagcttc caggggggaaa cgcctggtat ctttatagtc ctgtcgggtt   4555
tcgccacctc tgacttgagc gtcgattttt gtgatgctcg tcagggggc ggagcctatg   4615 gaaaaacgcc agcaacgcgg ccttttacg gttcctggcc ttttgctggc cttttgctca   4675
catgttcttt cctgcgttat ccctgattc tgtggataac cgtattaccg ccatgcat    4733
```

<210> SEQ ID NO 2
<211> LENGTH: 239
<212> TYPE: PRT
<213> ORGANISM: Artificial Sequence
<220> FEATURE:
<223> OTHER INFORMATION: Description of Artificial Sequence: pEGFP-N1
      cloning vector (Clonetech)

<400> SEQUENCE: 2

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
    65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
           100                 105                 110

Val Lys Phe Glu Gly Asp Thr Leu Val Asn Arg Ile Glu Leu Lys Gly
       115                 120                 125

Ile Asp Phe Lys Glu Asp Gly Asn Ile Leu Gly His Lys Leu Glu Tyr
   130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 3
<211> LENGTH: 3023
<212> TYPE: DNA

```
<213> ORGANISM: Homo sapiens
<220> FEATURE:
<221> NAME/KEY: CDS
<222> LOCATION: (391)..(1737)

<400> SEQUENCE: 3
ggggtaagga gttcaaggca gcgcccacac ccgggggctc tccgcaaccc gaccgcctgt    60
ccgctccccc acttcccgcc ctccctccca cctactcatt cacccaccca cccacccaga   120
gccgggacgg cagcccaggc gcccgggccc cgccgtctcc tcgccgcgat cctggacttc   180
ctcttgctgc aggacccggc ttccacgtgt gtcccggagc cggcgtctca gcacacgctc   240
cgctccgggc ctgggtgcct acagcagcca gagcagcagg gagtccggga cccgggcggc   300
atctgggcca gttaggcgc cgccgaggcc agcgctgaac gtctccaggg ccggaggagc   360
cgcggggcgt ccgggtctga ccgcagcaa atg ggc tcc gac gtg cgg gac ctg     414
                                Met Gly Ser Asp Val Arg Asp Leu
                                 1               5 aac gcg ctg ctg ccc gcc gtc ccc tcc ctg ggt ggc ggc ggc tgt          462
Asn Ala Leu Leu Pro Ala Val Pro Ser Leu Gly Gly Gly Gly Cys
         10                  15                  20 gcc ctg cct gtg agc ggc gcg gcg cag tgg gcg ccg gtg ctg gac ttt      510
Ala Leu Pro Val Ser Gly Ala Ala Gln Trp Ala Pro Val Leu Asp Phe
 25                  30                  35                  40 gcg ccc ccg ggc gct tcg gct tac ggg tcg ttg ggc ggc ccc gcg ccg      558
Ala Pro Pro Gly Ala Ser Ala Tyr Gly Ser Leu Gly Gly Pro Ala Pro
                 45                  50                  55 cca ccg gct ccg ccg cca ccc ccg ccg ccg cct cac tcc ttc atc          606
Pro Pro Ala Pro Pro Pro Pro Pro Pro Pro Pro His Ser Phe Ile
             60                  65                  70 aaa cag gag ccg agc tgg ggc ggc gcg gag ccg cac gag gag cag tgc      654
Lys Gln Glu Pro Ser Trp Gly Gly Ala Glu Pro His Glu Glu Gln Cys
         75                  80                  85 ctg agc gcc ttc act gtc cac ttt tcc ggc cag ttc act ggc aca gcc      702
Leu Ser Ala Phe Thr Val His Phe Ser Gly Gln Phe Thr Gly Thr Ala
 90                  95                 100 gga gcc tgt cgc tac ggg ccc ttc ggt cct cct ccg ccc agc cag gcg      750
Gly Ala Cys Arg Tyr Gly Pro Phe Gly Pro Pro Pro Pro Ser Gln Ala
105                 110                 115                 120 tca tcc ggc cag gcc agg atg ttt cct aac gcg ccc tac ctg ccc agc      798
Ser Ser Gly Gln Ala Arg Met Phe Pro Asn Ala Pro Tyr Leu Pro Ser
                125                 130                 135 tgc ctc gag agc cag ccc gct att cgc aat cag ggt tac agc acg gtc      846
Cys Leu Glu Ser Gln Pro Ala Ile Arg Asn Gln Gly Tyr Ser Thr Val
            140                 145                 150 acc ttc gac ggg acg ccc agc tac ggt cac acg ccc tcg cac cat gcg      894
Thr Phe Asp Gly Thr Pro Ser Tyr Gly His Thr Pro Ser His His Ala
        155                 160                 165 gcg cag ttc ccc aac cac tca ttc aag cat gag gat ccc atg ggc cag      942
Ala Gln Phe Pro Asn His Ser Phe Lys His Glu Asp Pro Met Gly Gln
    170                 175                 180 cag ggc tcg ctg ggt gag cag cag tac tcg gtg ccg ccc ccg gtc tat      990
Gln Gly Ser Leu Gly Glu Gln Gln Tyr Ser Val Pro Pro Pro Val Tyr
185                 190                 195                 200 ggc tgc cac acc ccc acc gac agc tgc acc ggc agc cag gct ttg ctg     1038
Gly Cys His Thr Pro Thr Asp Ser Cys Thr Gly Ser Gln Ala Leu Leu
                205                 210                 215 ctg agg acg ccc tac agc agt gac aat tta tac caa atg aca tcc cag     1086
Leu Arg Thr Pro Tyr Ser Ser Asp Asn Leu Tyr Gln Met Thr Ser Gln
            220                 225                 230
```

```
ctt gaa tgc atg acc tgg aat cag atg aac tta gga gcc acc tta aag      1134
Leu Glu Cys Met Thr Trp Asn Gln Met Asn Leu Gly Ala Thr Leu Lys
        235                 240                 245 gga gtt gct gct ggg agc tcc agc tca gtg aaa tgg aca gaa ggg cag      1182
Gly Val Ala Ala Gly Ser Ser Ser Ser Val Lys Trp Thr Glu Gly Gln
    250                 255                 260 agc aac cac agc aca ggg tac gag agc gat aac cac aca acg ccc atc      1230
Ser Asn His Ser Thr Gly Tyr Glu Ser Asp Asn His Thr Thr Pro Ile
265                 270                 275                 280 ctc tgc gga gcc caa tac aga ata cac acg cac ggt gtc ttc aga ggc      1278
Leu Cys Gly Ala Gln Tyr Arg Ile His Thr His Gly Val Phe Arg Gly
                285                 290                 295 att cag gat gtg cga cgt gtg cct gga gta gcc ccg act ctt gta cgg      1326
Ile Gln Asp Val Arg Arg Val Pro Gly Val Ala Pro Thr Leu Val Arg
            300                 305                 310 tcg gca tct gag acc agt gag aaa cgc ccc ttc atg tgt gct tac cca      1374
Ser Ala Ser Glu Thr Ser Glu Lys Arg Pro Phe Met Cys Ala Tyr Pro
        315                 320                 325 ggc tgc aat aag aga tat ttt aag ctg tcc cac tta cag atg cac agc      1422
Gly Cys Asn Lys Arg Tyr Phe Lys Leu Ser His Leu Gln Met His Ser
    330                 335                 340 agg aag cac act ggt gag aaa cca tac cag tgt gac ttc aag gac tgt      1470
Arg Lys His Thr Gly Glu Lys Pro Tyr Gln Cys Asp Phe Lys Asp Cys
345                 350                 355                 360 gaa cga agg ttt tct cgt tca gac cag ctc aaa aga cac caa agg aga      1518
Glu Arg Arg Phe Ser Arg Ser Asp Gln Leu Lys Arg His Gln Arg Arg
                365                 370                 375 cat aca ggt gtg aaa cca ttc cag tgt aaa act tgt cag cga aag ttc      1566
His Thr Gly Val Lys Pro Phe Gln Cys Lys Thr Cys Gln Arg Lys Phe
            380                 385                 390 tcc cgg tcc gac cac ctg aag acc cac acc agg act cat aca ggt aaa      1614
Ser Arg Ser Asp His Leu Lys Thr His Thr Arg Thr His Thr Gly Lys
        395                 400                 405 aca agt gaa aag ccc ttc agc tgt cgg tgg cca agt tgt cag aaa aag      1662
Thr Ser Glu Lys Pro Phe Ser Cys Arg Trp Pro Ser Cys Gln Lys Lys
    410                 415                 420 ttt gcc cgg tca gat gaa tta gtc cgc cat cac aac atg cat cag aga      1710
Phe Ala Arg Ser Asp Glu Leu Val Arg His His Asn Met His Gln Arg
425                 430                 435                 440 aac atg acc aaa ctc cag ctg gcg ctt tgaggggtct ccctcgggga            1757
Asn Met Thr Lys Leu Gln Leu Ala Leu
                445 ccgttcagtg tcccaggcag cacagtgtgt gaactgcttt caagtctgac tctccactcc   1817 tcctcactaa aaaggaaact tcagttgatc ttcttcatcc aacttccaag acaagatacc   1877 ggtgcttctg gaaactacca ggtgtgcctg aagagttgg tctctgccct gcctactttt    1937 agttgactca caggccctgg agaagcagct aacaatgtct ggttagttaa agcccattg    1997 ccatttggtg tggattttct actgtaagaa gagccatagc tgatcatgtc ccctgaccc    2057 ttcccttctt tttttatgct cgttttcgct ggggatggaa ttattgtacc attttctatc   2117 atggaatatt tataggccag gcatgtgta tgtgtctgct aatgtaaact ttgtcatggt    2177 ttccatttac taacagcaac agcaagaaat aaatcagaga gcaaggcatc ggggtgaat    2237 cttgtctaac attcccgagg tcagccaggc tgctaacctg gaaagcagga tgtagttctg   2297 ccaggcaact tttaaagctc atgcatttca agcagctgaa gaaaaaatca gaactaacca   2357 gtacctctgt atagaaatct aaaagaattt taccattcag ttaattcaat gtgaacactg   2417 gcacactgct cttaagaaac tatgaagatc tgagattttt ttgtgtatgt ttttgactct   2477
```

-continued

```
tttgagtggt aatcatatgt gtctttatag atgtacatac ctccttgcac aaatggaggg      2537
gaattcattt tcatcactgg gagtgtcctt agtgtataaa aaccatgctg gtatatggct      2597
tcaagttgta aaaatgaaag tgactttaaa agaaaatagg ggatggtcca ggatctccac      2657
tgataagact gttttttaagt aacttaagga cctttgggtc tacaagtata tgtgaaaaaa     2717
atgagactta ctgggtgagg aaatccattg tttaaagatg gtcgtgtgtg tgtgtgtgtg      2777
tgtgtgtgtg tgtgtgttgt gttgtgtttt gttttttaag ggagggaatt tattatttac      2837
cgttgcttga aattactgtg taaatatatg tctgataatg atttgctctt tgacaactaa      2897
aattaggact gtataagtac tagatgcatc actgggtgtt gatcttacaa gatattgatg      2957
ataacactta aaattgtaac ctgcattttt cactttgctc tcaattaaag tctattcaaa      3017
aggaaa                                                                 3023
```

<210> SEQ ID NO 4
<211> LENGTH: 449
<212> TYPE: PRT
<213> ORGANISM: Homo sapiens

<400> SEQUENCE: 4

```
Met Gly Ser Asp Val Arg Asp Leu Asn Ala Leu Leu Pro Ala Val
  1               5                  10                  15

Ser Leu Gly Gly Gly Gly Cys Ala Leu Pro Val Ser Gly Ala Ala
                 20                  25                  30

Gln Trp Ala Pro Val Leu Asp Phe Ala Pro Pro Gly Ala Ser Ala Tyr
         35                  40                  45

Gly Ser Leu Gly Gly Pro Ala Pro Pro Ala Pro Pro Pro Pro
     50                  55                  60

Pro Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Val His Phe
                 85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270
```

```
Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
        290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
        370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
                420                 425                 430

Arg His His Asn Met His Gln Arg Asn Met Thr Lys Leu Gln Leu Ala
            435                 440                 445

Leu

<210> SEQ ID NO 5
<211> LENGTH: 458
<212> TYPE: DNA
<213> ORGANISM: Human papillomavirus type 16
<220> FEATURE:
<221> NAME/KEY: CDS
<222> LOCATION: (3)..(455)

<400> SEQUENCE: 5 ca atg ttt cag gac cca cag gag cga ccc gga aag tta cca cag tta       47
   Met Phe Gln Asp Pro Gln Glu Arg Pro Gly Lys Leu Pro Gln Leu
    1               5                  10                  15 tgc aca gag ctg caa aca act ata cat gat ata ata tta gaa tgt gtg      95
Cys Thr Glu Leu Gln Thr Thr Ile His Asp Ile Ile Leu Glu Cys Val
                20                  25                  30 tac tgc aag caa cag tta ctg cga cgt gag gta tat gac ttt gct ttt     143
Tyr Cys Lys Gln Gln Leu Leu Arg Arg Glu Val Tyr Asp Phe Ala Phe
            35                  40                  45 cgg gat tta tgc ata gta tat aga gat ggg aat cca tat gct gta tgt     191
Arg Asp Leu Cys Ile Val Tyr Arg Asp Gly Asn Pro Tyr Ala Val Cys
        50                  55                  60 gat aaa tgt tta aag ttt tat tct aaa att agt gag tat aga cat tat     239
Asp Lys Cys Leu Lys Phe Tyr Ser Lys Ile Ser Glu Tyr Arg His Tyr
65                  70                  75 tgt tat agt gtg tat gga aca aca tta gaa cag caa tac aac aaa ccg     287
Cys Tyr Ser Val Tyr Gly Thr Thr Leu Glu Gln Gln Tyr Asn Lys Pro
 80                  85                  90                  95 ttg tgt gat ttg tta att agg tgt att aac tgt caa aag cca ctg tgt     335
Leu Cys Asp Leu Leu Ile Arg Cys Ile Asn Cys Gln Lys Pro Leu Cys
                100                 105                 110 cct gaa gaa aag caa aga cat ctg gac aaa aag caa aga ttc cat aat     383
Pro Glu Glu Lys Gln Arg His Leu Asp Lys Lys Gln Arg Phe His Asn
            115                 120                 125
```

```
ata agg ggt cgg tgg acc ggt cga tgt atg tct tgt tgc aga tca tca    431
Ile Arg Gly Arg Trp Thr Gly Arg Cys Met Ser Cys Cys Arg Ser Ser
        130                 135                 140 aga aca cgt aga gaa acc cag ctg taa                                458
Arg Thr Arg Arg Glu Thr Gln Leu
    145                 150

<210> SEQ ID NO 6
<211> LENGTH: 151
<212> TYPE: PRT
<213> ORGANISM: Human papillomavirus type 16

<400> SEQUENCE: 6

Met Phe Gln Asp Pro Gln Glu Arg Pro Gly Lys Leu Pro Gln Leu Cys
 1               5                  10                  15

Thr Glu Leu Gln Thr Thr Ile His Asp Ile Ile Leu Glu Cys Val Tyr
             20                  25                  30

Cys Lys Gln Gln Leu Leu Arg Arg Glu Val Tyr Asp Phe Ala Phe Arg
         35                  40                  45

Asp Leu Cys Ile Val Tyr Arg Asp Gly Asn Pro Tyr Ala Val Cys Asp
     50                  55                  60

Lys Cys Leu Lys Phe Tyr Ser Lys Ile Ser Glu Tyr Arg His Tyr Cys
 65                  70                  75                  80

Tyr Ser Val Tyr Gly Thr Thr Leu Glu Gln Gln Tyr Asn Lys Pro Leu
                 85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 7
<211> LENGTH: 540
<212> TYPE: DNA
<213> ORGANISM: Artificial Sequence
<220> FEATURE:
<221> NAME/KEY: CDS
<222> LOCATION: (82)..(375)
<220> FEATURE:
<223> OTHER INFORMATION: Description of Artificial Sequence: fragment of
      human papilloma virus type 16 E7 gene

<400> SEQUENCE: 7
taatataagg ggtcggtgga ccggtcgatg tatgtcttgt tgcagatcat caagaacacg     60
tagagaaacc cagctgtaat c atg cat gga gat aca cct aca ttg cat gaa     111
                        Met His Gly Asp Thr Pro Thr Leu His Glu
                         1               5                  10 tat atg tta gat ttg caa cca gag aca act gat ctc tac tgt tat gag    159
Tyr Met Leu Asp Leu Gln Pro Glu Thr Thr Asp Leu Tyr Cys Tyr Glu
             15                  20                  25 caa tta aat gac agc tca gag gag gag gat gaa ata gat ggt cca gct    207
Gln Leu Asn Asp Ser Ser Glu Glu Glu Asp Glu Ile Asp Gly Pro Ala
         30                  35                  40 gga caa gca gaa ccg gac aga gcc cat tac aat att gta acc ttt tgt    255
Gly Gln Ala Glu Pro Asp Arg Ala His Tyr Asn Ile Val Thr Phe Cys
     45                  50                  55 tgc aag tgt gac tct acg ctt cgg ttg tgc gta caa agc aca cac gta    303
```

```
Cys Lys Cys Asp Ser Thr Leu Arg Leu Cys Val Gln Ser Thr His Val
         60                  65                  70 gac att cgt act ttg gaa gac ctg tta atg ggc aca cta gga att gtg      351
Asp Ile Arg Thr Leu Glu Asp Leu Leu Met Gly Thr Leu Gly Ile Val
 75                  80                  85                  90 tgc ccc atc tgt tct cag aaa cca taatctacca tggctgatcc tgcaggtacc    405
Cys Pro Ile Cys Ser Gln Lys Pro
                 95 aatggggaag agggtacggg atgtaatgga tggttttatg tagaggctgt agtggaaaaa    465 aaaacagggg atgctatatc agatgacgag aacgaaaatg acagtgatac aggtgaagat    525 ttggtagatt ttata                                                     540

<210> SEQ ID NO 8
<211> LENGTH: 98
<212> TYPE: PRT
<213> ORGANISM: Artificial Sequence
<220> FEATURE:
<223> OTHER INFORMATION: Description of Artificial Sequence: fragment of
      human papilloma virus type 16 E7 gene

<400> SEQUENCE: 8

Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn Asp Ser Ser
             20                  25                  30

Glu Glu Glu Asp Glu Ile Asp Gly Pro Ala Gly Gln Ala Glu Pro Asp
         35                  40                  45

Arg Ala His Tyr Asn Ile Val Thr Phe Cys Cys Lys Cys Asp Ser Thr
     50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
             85                  90                  95

Lys Pro

<210> SEQ ID NO 9
<211> LENGTH: 2627
<212> TYPE: DNA
<213> ORGANISM: Human immunodeficiency virus

<400> SEQUENCE: 9
gaattcagag cagaagacag tggcaatgag agtgaagggg atcaggagga attatcagca     60
ctggtgggga tggggcacga tgctccttgg gttattaatg atctgtagtg ctacagaaaa    120
attgtgggtc acagtctatt atggggtacc tgtgtggaaa gaagcaacca ccactctatt    180
ttgtgcatca gatgctaaag catatgatac agaggtacat aatgtttggg ccacacatgc    240
ctgtgtaccc acagacccca acccacaaga agtaaaattg gtaaatgtga cagaaaattt    300
taacatgtgg aaaaataacg tggtagaaca gatgcatgag gatataatca gtttatggga    360
tcaaagccta aagccatgtg taaaattaac cccactctgt gttactttaa attgcactga    420
tttgaggaat actactaata ccaataatag tactgctaat aacaatagta atagcgaggg    480
aacaataaag ggaggagaaa tgaaaaactg ctctttcaat atcaccacaa gcataagaga    540
taagatgcag aaagaatatg cacttcttta taaacttgat atagtatcaa tagataatga    600
tagtaccagc tataggttga taagttgtaa tacctcagtc attacacaag cttgtccaaa    660
gatatccttt gagccaattc ccatacacta ttgtgccccg gctggttttg cgattctaaa    720
```

```
gtgtaacgta aaaaagttca gtggaaaagg atcatgtaaa aatgtcagca cagtacaatg      780
tacacatgga attaggccag tagtatcagt tcaactgctg ttaaatggca gtctagcaga      840
agaagaggta gtaattagat ctgagaattt cactgataat gctaaaacca tcatagtaca     900
tctgaatgaa tctgtacaaa ttaattgtac aagacccaac tacaataaaa gaaaaaggat     960
acatatagga ccagggagag catttttatac aacaaaaaat ataaaggaa ctataagaca    1020 agcacattgt aacattagta gagcaaaatg gaatgacact ttaagacaga tagttagcaa    1080
attaaaagaa caatttaaga ataaaacaat agtctttact caatcctcag gaggggaccc    1140
agaaattgta atgcacagtt ttaattgtgg aggggaattt ttctactgta atacatcacc    1200 actgttttaat agtacttgga atggtaataa tacttggaat aatactacgg ggtcaaataa    1260
caatatcaca cttcaatgca aaataaaaca aattataaac atgtggcaga aagtaggaaa    1320
agcaatgtat gcccctccca ttgaaggaca aattagatgt tcatcaaata ttacagggct    1380
actattaaca agagatggtg gtaaggacac ggacacgaac gacaccgaga tcttcagacc    1440
tggaggagga gatatgaggg acaattggag aagtgaatta tataaatata agtagtaac    1500 aattgaacca ttaggagtag cacccaccaa ggcaaagaga agagtggtgc agagagaaaa    1560
aagagcagcg ataggagctc tgttccttgg gttcttagga gcggcaggaa gcactatggg    1620
cgcagcgtca gtgacgctga cggtacaggc cagactatta ttgtctggta tagtgcaaca    1680
gcagaacaat ttgctgaggg ccattgagtc gcaacagcat atgttgcaac tcacagtctg    1740
gggcatcaag cagctccagg caagagtcct ggctgtggaa agatacctaa aggatcaaca    1800
gctcctgggg ttttggggtt gctctggaaa actcatttgc accactactg tgccttggaa    1860
tgctagttgg agtaataaat ctctggatga tatttggaat aacatgacct ggatgcagtg    1920
ggaaagagaa attgacaatt acacaagctt aatatactca ttactagaaa aatcgcaaac    1980
ccaacaagaa aagaatgaac aagaattatt ggaattggat aaatgggcaa gtttgtggaa    2040
ttggtttgac ataacaaatt ggctgtggta tataaaaata ttcataatga tagtaggagg    2100
ctggtaggtt taagaatagt ttttactgta ctttctatag tgaatagagt taggcaggga    2160
tactcaccat tgtcgttgca gacccgcccc ccagttccga ggggacccga caggcccgaa    2220
ggaatcgaag aagaaggtgg agagagagac agagacacat ccggtcgatt agtgcatgga    2280
ttcttagcaa ttatctgggt cgacctgcgg agcctgttcc tcttcagcta ccaccacttg    2340
agagacttac tcttgattgc agcgaggagt gtggaacttc tgggacgcag ggggtgggaa    2400
gtcctcaaat attggtggaa tctcctacag tattggagtc aggaactaaa gaatagtgct    2460
gttagcttgc ttaatgccac agctatagca gtagctgagg ggacagatag ggttatagaa    2520
gtactgcaaa gagctggtag agctattctc cacataccta caagaataag acagggcttg    2580
gaaagggctt tgctataaga tgggtggcaa gtggtcaaag cggccgc                   2627

<210> SEQ ID NO 10
<211> LENGTH: 1564
<212> TYPE: DNA
<213> ORGANISM: Human immunodeficiency virus

<400> SEQUENCE: 10
gaattccatg ggtgcgagag cgtcggtatt aagcggggga gaattagatc gatgggaaaa      60
aattcggtta aggccagggg gaaagaaaaa atataaatta aaacatgtag tatgggcaag     120
cagggagcta gaacgattcg cagtcaatcc tggcctgtta gaaacatcag aaggctgtag     180
```

-continued

```
acaaatactg ggacagctac aaccatccct tcagacagga tcagaagaac gtaaatcatt      240
atataataca gtagcaaccc tctattgtgt gcatcaaaag atagagataa aagacaccaa      300
ggaagcttta gagaaaatag aggaagagca aaacaaaagt aagaaaaaag cacagcaagc      360
agcagctgac acaggaaaca gaggaaacag cagccaagtc agccaaaatt accccatagt      420
gcagaacatc caggggcaaa tggtacatca ggccatatca cctagaactt taaatgcatg      480
ggtaaaagta gtagaagaga aggctttcag cccagaagta atacccatgt tttcagcatt      540
atcagaagga gccaccccac aagatttaaa caccatgcta aacacagtgg ggggacatca      600
agcagccatg caaatgttaa aagagaccat caatgaggaa gctgcagaat gggatagatt      660
gcatccagtg catgcagggc ctattgcacc aggccagatg agagaaccaa ggggaagtga      720
catagcagga actactagta cccttcagga caaatagga tggatgacaa ataatccacc      780
tatcccagta ggagaaatct ataaaagatg gataatcctg ggattaaata aaatagtaag      840
gatgtatagc ccttccagca tcctggacat aagacaagga ccaaaggaac cctttagaga      900
ctatgtagac cggttctata aaactctaag agccgagcaa gcttcacagg aggtaaaaaa      960
ttggatgaca gaaaccttgt tggtccaaaa tgcgaaccca gattgtaaga ctattttaaa     1020
agcattggga ccagcagcta cactagaaga aatgatgaca gcatgtcagg gagtgggagg     1080
acctggtcat aaagcaggag ttttggcgga agcgatgagc caagtaacaa attcagctac     1140
cataatggtg cagagaggca attttaggaa tcaaagaaag attatcaagt gcttcaattg     1200
tggcaaagaa gggcacatag ccaaaaattg cagggcccct aggaaaaggg gctgttggaa     1260
atgtggaaag gaaggacacc aaatgaaaga ttgtactgag ggacaggcta atttttagg      1320 gaagatctgg ccttcctgca agggaaggcc agggaatttt cctcagagca gaacagagcc     1380
aacagcccca ccagaagaga gcttcaggtt tggggaagag acaacaactc cctaccagaa     1440
gcaggagaag aagcaggaga caatagacaa ggacctgtat cctttagctt ccctcaaatc     1500
actctttggc aacgacccat tgtcacaata agcggccgct cgagtctaga gggcccgttt     1560
aaac                                                                  1564
```

<210> SEQ ID NO 11
<211> LENGTH: 318
<212> TYPE: DNA
<213> ORGANISM: Human immunodeficiency virus

<400> SEQUENCE: 11

```
gaattcatgg agccagtaga tcctaaacta gagccctgga agcatccagg aagtcagcct       60
aagactgctt gtaacaattg ctattgtaaa aagtgttgct ttcattgcca gtttgtttc      120 acaaaaaaag gcttaggcat ctcctatggc aggaagaagc ggagacagcg acgaagatct      180
cctcaagaca gtgagactca tcaagtttct ctatcaaagc aacccgcctc ccagccccga      240
ggggacccga caggcccgaa ggaatcgaag aagaaggttg agagagagac agagacagat      300
ccggtcgatt aggtcgac                                                   318
```

<210> SEQ ID NO 12
<211> LENGTH: 318
<212> TYPE: DNA
<213> ORGANISM: Human immunodeficiency virus

<400> SEQUENCE: 12

```
gaattcatgg agccagtaga tcctaaacta gagccctgga agcatccagg aagtcagcct       60
aagactgctt gtaacaattg ctattcgaaa aagtgttgct ttcattgcca gtttgtttc      120
```

```
acaaaaaaag cttaggcat ctcctatggc aggaagacgc ggagacagct gcgaagatct    180
cctcaagaca gtgagactca tcaagtttct ctatcaaagc aacccgcctc ccagccccga    240
ggggacccga caggcccgaa ggaatcgaag aagaaggtgg agagagagac agagacagat    300
ccggtcgatt aggtcgac                                                  318

<210> SEQ ID NO 13
<211> LENGTH: 742
<212> TYPE: DNA
<213> ORGANISM: Human immunodeficiency virus

<400> SEQUENCE: 13
cctagaagaa taagacaggg ctttgaagcc gtgttgctat aaaatggggg gcaaatggtc     60
aaaatccagt atagttgggt ggcctgcagt aagagacaaa ataagaggaa ctgatccagc    120
agcaaaggga gtaggagcag cgtctcaaga cttagataaa tatggggcac ttacaagcag    180
caacacaccc gccaataatg ctgattgtgc ctggctggaa gcgcaagagg aggaaggaga    240
agtaggcttt ccagtcagac ctcaggtacc tttaagacca atgacttata agggagcatt    300
cgatctcggc ttcttttaa aagaaaaggg gggactggaa ggggtaattt actccaagaa    360
aaggcaagag atccttgatt tgtgggtcta tcacacacaa gcttcttcc ctgattggca    420 aaactacaca ccaggaccag gggtcagata tccattgacc tttggatggt gcttcaagct    480
agtgccagtt gacccaaggg aagtggaaga ggccaatgaa ggagaggaca actgcttact    540
gcatcctatg agcctgcatg gaatggagga tgcacacgga gaagtattaa ggtggaagta    600
tgacagtaaa ctagcacgca gacacatggc ccgcgagcta catccggagt attacaaaga    660
ctgctgacac agaagggact ttccgctggg actttccact ggggcgttcc aggaggagtg    720
gtctgggcgg gactgggagt gg                                            742

<210> SEQ ID NO 14
<211> LENGTH: 394
<212> TYPE: DNA
<213> ORGANISM: Human immunodeficiency virus

<400> SEQUENCE: 14
cccgggcatc tcctatggca ggaagaagcg gagacagcga cgaagagctc ctcaaggcag     60
tcagactcat caagtttctc tatcaaagca acccacctcc caatcccgag ggacccgac    120 aggcccgaag gaatagaaga agaaggtgga gagagagaca gagacagatc cattcgatta    180
gtgaacggat ccttagcact tatctgggac gatctgcgga gcctgtgcct cttcagctac    240
caccgcttga gagacttact cttgattgta cgaggattg tggaacttct gggacgcagg    300
gggtgggaag ccctcaaata ttggtggaat ctcctacaat attggagtca ggagctaaag    360
aatagtgctg ttagcttgct caatgccatc taga                               394

<210> SEQ ID NO 15
<211> LENGTH: 1524
<212> TYPE: DNA
<213> ORGANISM: Homo sapiens
<220> FEATURE:
<221> NAME/KEY: CDS
<222> LOCATION: (54)..(407)

<400> SEQUENCE: 15
agcagacaga ggactctcat taaggaaggt gtcctgtgcc ctgaccctac aag atg      56
                                                          Met
                                                           1
```

```
cca aga gaa gat gct cac ttc atc tat ggt tac ccc aag aag ggg cac        104
Pro Arg Glu Asp Ala His Phe Ile Tyr Gly Tyr Pro Lys Lys Gly His
              5                  10                  15 ggc cac tct tac acc acg gct gaa gag gcc gct ggg atc ggc atc ctg        152
Gly His Ser Tyr Thr Thr Ala Glu Glu Ala Ala Gly Ile Gly Ile Leu
         20                  25                  30 aca gtg atc ctg gga gtc tta ctg ctc atc ggc tgt tgg tat tgt aga        200
Thr Val Ile Leu Gly Val Leu Leu Leu Ile Gly Cys Trp Tyr Cys Arg
 35                  40                  45 aga cga aat gga tac aga gcc ttg atg gat aaa agt ctt cat gtt ggc        248
Arg Arg Asn Gly Tyr Arg Ala Leu Met Asp Lys Ser Leu His Val Gly
 50                  55                  60                  65 act caa tgt gcc tta aca aga aga tgc cca caa gaa ggg ttt gat cat        296
Thr Gln Cys Ala Leu Thr Arg Arg Cys Pro Gln Glu Gly Phe Asp His
             70                  75                  80 cgg gac agc aaa gtg tct ctt caa gag aaa aac tgt gaa cct gtg gtt        344
Arg Asp Ser Lys Val Ser Leu Gln Glu Lys Asn Cys Glu Pro Val Val
         85                  90                  95 ccc aat gct cca cct gct tat gag aaa ctc tct gca gaa cag tca cca        392
Pro Asn Ala Pro Pro Ala Tyr Glu Lys Leu Ser Ala Glu Gln Ser Pro
100                 105                 110 cca cct tat tca cct taagagccag cgagacacct gagacatgct gaaattattt        447
Pro Pro Tyr Ser Pro
    115 ctctcacact tttgcttgaa tttaatacag acatctaatg ttctcctttg gaatggtgta     507 ggaaaaatgc aagccatctc taataataag tcagtgttaa aattttagta ggtccgctag     567 cagtactaat catgtgagga aatgatgaga aatattaaat tgggaaaact ccatcaataa     627 atgttgcaat gcatgatact atctgtgcca gaggtaatgt tagtaaatcc atggtgttat     687 tttctgagag acagaattca agtgggtatt ctggggccat ccaatttctc tttacttgaa     747 atttggctaa taacaaacta gtcaggtttt cgaaccttga ccgacatgaa ctgtacacag     807 aattgttcca gtactatgga gtgctcacaa aggatacttt tacaggttaa gacaaagggt     867 tgactggcct atttatctga tcaagaacat gtcagcaatg tctctttgtg ctctaaaatt     927 ctattatact acaataatat attgtaaaga tcctatagct cttttttttt gagatggagt     987 ttcgcttttg ttgcccaggc tggagtgcaa tggcgcgatc ttggctcacc ataacctccg    1047 cctcccaggt tcaagcaatt ctcctgcctt agcctcctga gtagctggga ttacaggcgt    1107 gcgccactat gcctgactaa ttttgtagtt ttagtagaga cggggtttct ccatgttggt    1167 caggctggtc tcaaactcct gacctcaggt gatctgcccg cctcagcctc ccaaagtgct    1227 ggaattacag gcgtgagcca ccacgcctgg ctggatccta tatcttaggt aagacatata    1287 acgcagtcta attcatttc acttcaaggc tcaatgctat tctaactaat gacaagtatt     1347 ttctactaaa ccagaaattg gtagaaggat ttaaataagt aaaagctact atgtactgcc    1407 ttagtgctga tgcctgtgta ctgccttaaa tgtacctatg gcaatttagc tctcttgggt    1467 tcccaaatcc ctctcacaag aatgtgcaga agaaatcata aaggatcaga gattctg       1524

<210> SEQ ID NO 16
<211> LENGTH: 118
<212> TYPE: PRT
<213> ORGANISM: Homo sapiens

<400> SEQUENCE: 16

Met Pro Arg Glu Asp Ala His Phe Ile Tyr Gly Tyr Pro Lys Lys Gly
 1               5                  10                  15
```

```
His Gly His Ser Tyr Thr Thr Ala Glu Glu Ala Ala Gly Ile Gly Ile
             20                  25                  30

Leu Thr Val Ile Leu Gly Val Leu Leu Ile Gly Cys Trp Tyr Cys
         35                  40                  45

Arg Arg Arg Asn Gly Tyr Arg Ala Leu Met Asp Lys Ser Leu His Val
     50                  55                  60

Gly Thr Gln Cys Ala Leu Thr Arg Arg Cys Pro Gln Glu Gly Phe Asp
 65                  70                  75                  80

His Arg Asp Ser Lys Val Ser Leu Gln Glu Lys Asn Cys Glu Pro Val
                 85                  90                  95

Val Pro Asn Ala Pro Pro Ala Tyr Glu Lys Leu Ser Ala Glu Gln Ser
            100                 105                 110

Pro Pro Pro Tyr Ser Pro
        115

<210> SEQ ID NO 17
<211> LENGTH: 1722
<212> TYPE: DNA
<213> ORGANISM: Homo sapiens
<220> FEATURE:
<221> NAME/KEY: CDS
<222> LOCATION: (188)..(1114)

<400> SEQUENCE: 17
cgtagagttc ggccgaagga acctgaccca ggctctgtga ggaggcaagg ttttcagggg      60
acaggccaac ccagaggaca ggattccctg gaggccacag aggagcacca aggagaagat     120
ctgcctgtgg gtcttcattg cccagctcct gcccacactc ctgcctgctg ccctgacgag     180 agtcatc atg tct ctt gag cag agg agt ctg cac tgc aag cct gag gaa       229
        Met Ser Leu Glu Gln Arg Ser Leu His Cys Lys Pro Glu Glu
          1               5                  10 gcc ctt gag gcc caa caa gag gcc ctg ggc ctg gtg tgt gtg cag gct       277
Ala Leu Glu Ala Gln Gln Glu Ala Leu Gly Leu Val Cys Val Gln Ala
 15                  20                  25                  30 gcc gcc tcc tcc tcc tct cct ctg gtc ctg ggc acc ctg gag gag gtg       325
Ala Ala Ser Ser Ser Ser Pro Leu Val Leu Gly Thr Leu Glu Glu Val
                 35                  40                  45 ccc act gct ggg tca aca gat cct ccc cag agt cct cag gga gcc tcc       373
Pro Thr Ala Gly Ser Thr Asp Pro Pro Gln Ser Pro Gln Gly Ala Ser
         50                  55                  60 gcc ttt ccc act acc atc aac ttc act cga cag agg caa ccc agt gag       421
Ala Phe Pro Thr Thr Ile Asn Phe Thr Arg Gln Arg Gln Pro Ser Glu
 65                  70                  75 ggt tcc agc agc cgt gaa gag gag ggg cca agc acc tct tgt atc ctg       469
Gly Ser Ser Ser Arg Glu Glu Glu Gly Pro Ser Thr Ser Cys Ile Leu
         80                  85                  90 gag tcc ttg ttc cga gca gta atc act aag aag gtg gct gat ttg gtt       517
Glu Ser Leu Phe Arg Ala Val Ile Thr Lys Lys Val Ala Asp Leu Val
 95                 100                 105                 110 ggt ttt ctg ctc ctc aaa tat cga gcc agg gag cca gtc aca aag gca       565
Gly Phe Leu Leu Leu Lys Tyr Arg Ala Arg Glu Pro Val Thr Lys Ala
                115                 120                 125 gaa atg ctg gag agt gtc atc aaa aat tac aag cac tgt ttt cct gag       613
Glu Met Leu Glu Ser Val Ile Lys Asn Tyr Lys His Cys Phe Pro Glu
            130                 135                 140 atc ttc ggc aaa gcc tct gag tcc ttg cag ctg gtc ttt ggc att gac       661
Ile Phe Gly Lys Ala Ser Glu Ser Leu Gln Leu Val Phe Gly Ile Asp
        145                 150                 155
```

-continued

| | | |
|---|---|---|
| gtg aag gaa gca gac ccc acc ggc cac tcc tat gtc ctt gtc acc tgc<br>Val Lys Glu Ala Asp Pro Thr Gly His Ser Tyr Val Leu Val Thr Cys<br>    160                         165                  170 | 709 |
| cta ggt ctc tcc tat gat ggc ctg ctg ggt gat aat cag atc atg ccc<br>Leu Gly Leu Ser Tyr Asp Gly Leu Leu Gly Asp Asn Gln Ile Met Pro<br>175                        180                         185                  190 | 757 |
| aag aca ggc ttc ctg ata att gtc ctg gtc atg att gca atg gag ggc<br>Lys Thr Gly Phe Leu Ile Ile Val Leu Val Met Ile Ala Met Glu Gly<br>                      195                         200                      205 | 805 |
| ggc cat gct cct gag gag gaa atc tgg gag gag ctg agt gtg atg gag<br>Gly His Ala Pro Glu Glu Glu Ile Trp Glu Glu Leu Ser Val Met Glu<br>            210                        215                      220 | 853 |
| gtg tat gat ggg agg gag cac agt gcc tat ggg gag ccc agg aag ctg<br>Val Tyr Asp Gly Arg Glu His Ser Ala Tyr Gly Glu Pro Arg Lys Leu<br>              225                        230                      235 | 901 |
| ctc acc caa gat ttg gtg cag gaa aag tac ctg gag tac cgg cag gtg<br>Leu Thr Gln Asp Leu Val Gln Glu Lys Tyr Leu Glu Tyr Arg Gln Val<br>240                        245                        250 | 949 |
| ccg gac agt gat ccc gca cgc tat gag ttc ctg tgg ggt cca agg gcc<br>Pro Asp Ser Asp Pro Ala Arg Tyr Glu Phe Leu Trp Gly Pro Arg Ala<br>255                        260                        265                  270 | 997 |
| ctt gct gaa acc agc tat gtg aaa gtc ctt gag tat gtg atc aag gtc<br>Leu Ala Glu Thr Ser Tyr Val Lys Val Leu Glu Tyr Val Ile Lys Val<br>                      275                         280                      285 | 1045 |
| agt gca aga gtt cgc ttt ttc ttc cca tcc ctg cgt gaa gca gct ttg<br>Ser Ala Arg Val Arg Phe Phe Phe Pro Ser Leu Arg Glu Ala Ala Leu<br>            290                        295                      300 | 1093 |
| aga gag gag gaa gag gga gtc tgagcatgag ttgcagccag ggccagtggg<br>Arg Glu Glu Glu Glu Gly Val<br>        305 | 1144 |
| aggggggactg ggccagtgca ccttccaggg ccgcgtccag cagcttcccc tgcctcgtgt | 1204 |
| gacatgaggc ccattcttca ctctgaagag agcggtcagt gttctcagta gtaggttttct | 1264 |
| gttctattgg gtgacttgga gatttatctt tgttctcttt tggaattgtt caaatgtttt | 1324 |
| tttttaaggg atggttgaat gaacttcagc atccaagttt atgaatgaca gcagtcacac | 1384 |
| agttctgtgt atatagttta agggtaagag tcttgtgttt tattcagatt gggaaatcca | 1444 |
| ttctatttg tgaattggga taataacagc agtggaataa gtacttagaa atgtgaaaaa | 1504 |
| tgagcagtaa aatagatgag ataaagaact aaagaaatta agagatagtc aattcttgct | 1564 |
| ttatacctca gtctattctg taaaattttt aaagatatat gcatacctgg atttccttgg | 1624 |
| cttctttgag aatgtaagag aaattaaatc tgaataagaa attcttcctg ttaaaaaaaa | 1684 |
| aaaaaaaaaa aaaaaaaaaa aaaaaaaaaa aaaaaaa | 1722 |

<210> SEQ ID NO 18
<211> LENGTH: 309
<212> TYPE: PRT
<213> ORGANISM: Homo sapiens

<400> SEQUENCE: 18

Met Ser Leu Glu Gln Arg Ser Leu His Cys Lys Pro Glu Glu Ala Leu
 1               5                   10                  15

Glu Ala Gln Gln Glu Ala Leu Gly Leu Val Cys Val Gln Ala Ala Ala
            20                  25                  30

Ser Ser Ser Ser Pro Leu Val Leu Gly Thr Leu Glu Glu Val Pro Thr
        35                  40                  45

Ala Gly Ser Thr Asp Pro Pro Gln Ser Pro Gln Gly Ala Ser Ala Phe
    50                  55                  60

```
Pro Thr Thr Ile Asn Phe Thr Arg Gln Arg Gln Pro Ser Glu Gly Ser
 65                  70                  75                  80

Ser Ser Arg Glu Glu Glu Gly Pro Ser Thr Ser Cys Ile Leu Glu Ser
                 85                  90                  95

Leu Phe Arg Ala Val Ile Thr Lys Lys Val Ala Asp Leu Val Gly Phe
            100                 105                 110

Leu Leu Leu Lys Tyr Arg Ala Arg Glu Pro Val Thr Lys Ala Glu Met
        115                 120                 125

Leu Glu Ser Val Ile Lys Asn Tyr Lys His Cys Phe Pro Glu Ile Phe
    130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
            180                 185                 190

Gly Phe Leu Ile Ile Val Leu Val Met Ile Ala Met Glu Gly Gly His
        195                 200                 205

Ala Pro Glu Glu Glu Ile Trp Glu Leu Ser Val Met Glu Val Tyr
    210                 215                 220

Asp Gly Arg Glu His Ser Ala Tyr Gly Glu Pro Arg Lys Leu Leu Thr
225                 230                 235                 240

Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
            260                 265                 270

Glu Thr Ser Tyr Val Lys Val Leu Glu Tyr Val Ile Lys Val Ser Ala
        275                 280                 285

Arg Val Arg Phe Phe Phe Pro Ser Leu Arg Glu Ala Ala Leu Arg Glu
    290                 295                 300

Glu Glu Glu Gly Val
305

<210> SEQ ID NO 19
<211> LENGTH: 1753
<212> TYPE: DNA
<213> ORGANISM: Homo sapiens
<220> FEATURE:
<221> NAME/KEY: CDS
<222> LOCATION: (210)..(1151)

<400> SEQUENCE: 19
gagattctcg ccctgagcaa cgagcgacgg cctgacgtcg gcggagggaa gccggcccag      60
gctcggtgag gaggcaaggt tctgagggga caggctgacc tggaggacca gaggcccccg     120
gaggagcact gaaggagaag atctgccagt gggtctccat tgcccagctc ctgcccacac     180
tcccgcctgt tgccctgacc agagtcatc atg cct ctt gag cag agg agt cag      233
                                  Met Pro Leu Glu Gln Arg Ser Gln
                                    1               5 cac tgc aag cct gaa gaa ggc ctt gag gcc cga gga gag gcc ctg ggc      281
His Cys Lys Pro Glu Glu Gly Leu Glu Ala Arg Gly Glu Ala Leu Gly
         10                  15                  20 ctg gtg ggt gcg cag gct cct gct act gag gag cag gag gct gcc tcc      329
Leu Val Gly Ala Gln Ala Pro Ala Thr Glu Glu Gln Glu Ala Ala Ser
     25                  30                  35                  40 tcc tct tct act cta gtt gaa gtc acc ctg ggg gag gtg cct gct gcc      377
```

```
                                                                              -continued Ser Ser Ser Thr Leu Val Glu Val Thr Leu Gly Glu Val Pro Ala Ala
            45                  50                  55 gag tca cca gat cct ccc cag agt cct cag gga gcc tcc agc ctc ccc       425
Glu Ser Pro Asp Pro Pro Gln Ser Pro Gln Gly Ala Ser Ser Leu Pro
                60                  65                  70 act acc atg aac tac cct ctc tgg agc caa tcc tat gag gac tcc agc       473
Thr Thr Met Asn Tyr Pro Leu Trp Ser Gln Ser Tyr Glu Asp Ser Ser
            75                  80                  85 aac caa gaa gag gag ggg cca agc acc ttc cct gac ctg gag tcc gag       521
Asn Gln Glu Glu Glu Gly Pro Ser Thr Phe Pro Asp Leu Glu Ser Glu
        90                  95                 100 ttc caa gca gca ctc agt agg aag gtg gcc gag ttg gtt cat ttt ctg       569
Phe Gln Ala Ala Leu Ser Arg Lys Val Ala Glu Leu Val His Phe Leu
105                 110                 115                 120 ctc ctc aag tat cga gcc agg gag ccg gtc aca aag gca gaa atg ctg       617
Leu Leu Lys Tyr Arg Ala Arg Glu Pro Val Thr Lys Ala Glu Met Leu
                125                 130                 135 ggg agt gtc gtc gga aat tgg cag tat ttc ttt cct gtg atc ttc agc       665
Gly Ser Val Val Gly Asn Trp Gln Tyr Phe Phe Pro Val Ile Phe Ser
            140                 145                 150 aaa gct tcc agt tcc ttg cag ctg gtc ttt ggc atc gag ctg atg gaa       713
Lys Ala Ser Ser Ser Leu Gln Leu Val Phe Gly Ile Glu Leu Met Glu
        155                 160                 165 gtg gac ccc atc ggc cac ttg tac atc ttt gcc acc tgc ctg ggc ctc       761
Val Asp Pro Ile Gly His Leu Tyr Ile Phe Ala Thr Cys Leu Gly Leu
170                 175                 180 tcc tac gat ggc ctg ctg ggt gac aat cag atc atg ccc aag gca ggc       809
Ser Tyr Asp Gly Leu Leu Gly Asp Asn Gln Ile Met Pro Lys Ala Gly
185                 190                 195                 200 ctc ctg ata atc gtc ctg gcc ata atc gca aga gag ggc gac tgt gcc       857
Leu Leu Ile Ile Val Leu Ala Ile Ile Ala Arg Glu Gly Asp Cys Ala
                205                 210                 215 cct gag gag aaa atc tgg gag gag ctg agt gtg tta gag gtg ttt gag       905
Pro Glu Glu Lys Ile Trp Glu Glu Leu Ser Val Leu Glu Val Phe Glu
            220                 225                 230 ggg agg gaa gac agt atc ttg ggg gat ccc aag aag ctg ctc acc caa       953
Gly Arg Glu Asp Ser Ile Leu Gly Asp Pro Lys Lys Leu Leu Thr Gln
        235                 240                 245 cat ttc gtg cag gaa aac tac ctg gag tac cgg cag gtc ccc ggc agt      1001
His Phe Val Gln Glu Asn Tyr Leu Glu Tyr Arg Gln Val Pro Gly Ser
250                 255                 260 gat cct gca tgt tat gaa ttc ctg tgg ggt cca agg gcc ctc gtt gaa      1049
Asp Pro Ala Cys Tyr Glu Phe Leu Trp Gly Pro Arg Ala Leu Val Glu
265                 270                 275                 280 acc agc tat gtg aaa gtc ctg cac cat atg gta aag atc agt gga gga      1097
Thr Ser Tyr Val Lys Val Leu His His Met Val Lys Ile Ser Gly Gly
                285                 290                 295 cct cac att tcc tac cca ccc ctg cat gag tgg gtt ttg aga gag ggg      1145
Pro His Ile Ser Tyr Pro Pro Leu His Glu Trp Val Leu Arg Glu Gly
            300                 305                 310 gaa gag tgagtctgag cacgagttgc agccagggcc agtgggaggg ggtctgggcc       1201
Glu Glu agtgcacctt ccggggccgc atcccttagt ttccactgcc tcctgtgacg tgaggcccat      1261
tcttcactct ttgaagcgag cagtcagcat tcttagtagt gggtttctgt tctgttggat      1321
gactttgaga ttattctttg tttcctgttg gagttgttca aatgttcctt ttaacggatg      1381
gttgaatgag cgtcagcatc caggtttatg aatgacagta gtcacacata gtgctgttta      1441
tatagtttag gagtaagagt cttgtttttt actcaaattg ggaaatccat tccattttgt      1501
```

-continued

```
gaattgtgac ataataatag cagtggtaaa agtatttgct taaaattgtg agcgaattag    1561
caataacata catgagataa ctcaagaaat caaaagatag ttgattcttg ccttgtacct    1621
caatctattc tgtaaaatta aacaaatatg caaaccagga tttccttgac ttctttgaga    1681
atgcaagcga aattaaatct gaataaataa ttcttcctct ccaaaaaaaa aaaaaaaaa     1741 aaaaaaaaaa aa                                                        1753
```

<210> SEQ ID NO 20
<211> LENGTH: 314
<212> TYPE: PRT
<213> ORGANISM: Homo sapiens

<400> SEQUENCE: 20

```
Met Pro Leu Glu Gln Arg Ser Gln His Cys Lys Pro Glu Glu Gly Leu
  1               5                  10                  15

Glu Ala Arg Gly Glu Ala Leu Gly Leu Val Gly Ala Gln Ala Pro Ala
             20                  25                  30

Thr Glu Gln Glu Ala Ala Ser Ser Ser Thr Leu Val Glu Val
         35                  40                  45

Thr Leu Gly Glu Val Pro Ala Ala Glu Ser Pro Asp Pro Pro Gln Ser
     50                  55                  60

Pro Gln Gly Ala Ser Ser Leu Pro Thr Thr Met Asn Tyr Pro Leu Trp
 65                  70                  75                  80

Ser Gln Ser Tyr Glu Asp Ser Ser Asn Gln Glu Glu Glu Gly Pro Ser
                 85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
    290                 295                 300

His Glu Trp Val Leu Arg Glu Gly Glu Glu
305                 310
```

```
<210> SEQ ID NO 21
<211> LENGTH: 756
<212> TYPE: DNA
<213> ORGANISM: Homo sapiens
<220> FEATURE:
<221> NAME/KEY: CDS
<222> LOCATION: (87)..(422)

<400> SEQUENCE: 21
gctggaggat gtggctgcag agcctgctgc tcttgggcac tgtggcctgc agcatctctg      60
cacccgcccg ctcgcccagc ccagc acg cag ccc tgg gag cat gtg aat gcc     113
                             Thr Gln Pro Trp Glu His Val Asn Ala
                              1               5 atc cag gag gcc cgg cgt ctc ctg aac ctg agt aga gac act gct gct     161
Ile Gln Glu Ala Arg Arg Leu Leu Asn Leu Ser Arg Asp Thr Ala Ala
 10              15                  20                  25 gag atg aat gaa aca gta gaa gtc atc tca gaa atg ttt gac ctc cag     209
Glu Met Asn Glu Thr Val Glu Val Ile Ser Glu Met Phe Asp Leu Gln
             30                  35                  40 gag ccg acc tgc cta cag acc cgc ctg gag ctg tac aag cag ggc ctg     257
Glu Pro Thr Cys Leu Gln Thr Arg Leu Glu Leu Tyr Lys Gln Gly Leu
         45                  50                  55 cgg ggc agc ctc acc aag ctc aag ggc ccc ttg acc atg atg gcc agc     305
Arg Gly Ser Leu Thr Lys Leu Lys Gly Pro Leu Thr Met Met Ala Ser
     60                  65                  70 cac tac aag cag cac tgc cct cca acc ccg gaa act tcc tgt gca acc     353
His Tyr Lys Gln His Cys Pro Pro Thr Pro Glu Thr Ser Cys Ala Thr
 75                  80                  85 cag act atc acc ttt gaa agt ttc aaa gag aac ctg aag gac ttt ctg     401
Gln Thr Ile Thr Phe Glu Ser Phe Lys Glu Asn Leu Lys Asp Phe Leu
             90                  95                 100                 105 ctt gtc atc ccc ttt gac tgc tgggagccag tccaggagtg agaccggcca         452
Leu Val Ile Pro Phe Asp Cys
                110 gatgaggctg gccaagccgg ggagctgctc tctcatgaaa caagagctag aaactcagga    512 tggtcatctt ggagggacca aggggtgggc cacagccatg gtgggagtgg cctggacctg    572 ccctgggcca cactgaccct gatacaggca tggcagaaga atgggaatat ttatactga    632 cagaaatcag taatatttat atatttatat tttaaaata tttatttatt tatttattta     692 agttcatatt ccatatttat tcaagatgtt ttaccgtaat aattattatt aaaaatatgc    752 ttct                                                                 756

<210> SEQ ID NO 22
<211> LENGTH: 112
<212> TYPE: PRT
<213> ORGANISM: Homo sapiens

<400> SEQUENCE: 22

Thr Gln Pro Trp Glu His Val Asn Ala Ile Gln Glu Ala Arg Arg Leu
 1               5                  10                  15

Leu Asn Leu Ser Arg Asp Thr Ala Ala Glu Met Asn Glu Thr Val Glu
             20                  25                  30

Val Ile Ser Glu Met Phe Asp Leu Gln Glu Pro Thr Cys Leu Gln Thr
         35                  40                  45

Arg Leu Glu Leu Tyr Lys Gln Gly Leu Arg Gly Ser Leu Thr Lys Leu
     50                  55                  60

Lys Gly Pro Leu Thr Met Met Ala Ser His Tyr Lys Gln His Cys Pro
 65                  70                  75                  80
```

```
Pro Thr Pro Glu Thr Ser Cys Ala Thr Gln Thr Ile Thr Phe Glu Ser
                85                  90                  95

Phe Lys Glu Asn Leu Lys Asp Phe Leu Leu Val Ile Pro Phe Asp Cys
            100                 105                 110

<210> SEQ ID NO 23
<211> LENGTH: 825
<212> TYPE: DNA
<213> ORGANISM: Homo sapiens
<220> FEATURE:
<221> NAME/KEY: CDS
<222> LOCATION: (48)..(515)

<400> SEQUENCE: 23
atcactctct ttaatcacta ctcacattaa cctcaactcc tgccaca atg tac agg        56
                                                    Met Tyr Arg
                                                      1 atg caa ctc ctg tct tgc att gca cta att ctt gca ctt gtc aca aac      104
Met Gln Leu Leu Ser Cys Ile Ala Leu Ile Leu Ala Leu Val Thr Asn
    5                  10                  15 agt gca cct act tca agt tcg aca aag aaa aca aag aaa aca cag cta      152
Ser Ala Pro Thr Ser Ser Ser Thr Lys Lys Thr Lys Lys Thr Gln Leu
 20                  25                  30                  35 caa ctg gag cat tta ctg ctg gat tta cag atg att ttg aat gga att      200
Gln Leu Glu His Leu Leu Leu Asp Leu Gln Met Ile Leu Asn Gly Ile
                 40                  45                  50 aat aat tac aag aat ccc aaa ctc acc agg atg ctc aca ttt aag ttt      248
Asn Asn Tyr Lys Asn Pro Lys Leu Thr Arg Met Leu Thr Phe Lys Phe
             55                  60                  65 tac atg ccc aag aag gcc aca gaa ctg aaa cag ctt cag tgt cta gaa      296
Tyr Met Pro Lys Lys Ala Thr Glu Leu Lys Gln Leu Gln Cys Leu Glu
         70                  75                  80 gaa gaa ctc aaa cct ctg gag gaa gtg ctg aat tta gct caa agc aaa      344
Glu Glu Leu Lys Pro Leu Glu Glu Val Leu Asn Leu Ala Gln Ser Lys
     85                  90                  95 aac ttt cac tta aga ccc agg gac tta atc agc aat atc aac gta ata      392
Asn Phe His Leu Arg Pro Arg Asp Leu Ile Ser Asn Ile Asn Val Ile
100                 105                 110                 115 gtt ctg gaa cta aag gga tct gaa aca aca ttc atg tgt gaa tat gca      440
Val Leu Glu Leu Lys Gly Ser Glu Thr Thr Phe Met Cys Glu Tyr Ala
                120                 125                 130 gat gag aca gca acc att gta gaa ttt ctg aac aga tgg att acc ttt      488
Asp Glu Thr Ala Thr Ile Val Glu Phe Leu Asn Arg Trp Ile Thr Phe
            135                 140                 145 tgt caa agc atc atc tca aca cta act tgataattaa gtgcttccca            535
Cys Gln Ser Ile Ile Ser Thr Leu Thr
        150                 155 cttaaaacat atcaggcctt ctatttattt atttaaatat ttaaatttta tatttattgt    595
tgaatgtatg gttgctacct attgtaacta ttattcttaa tcttaaaact ataaatatgg    655
atcttttatg attcttttg taagccctag gggctctaaa atggtttacc ttatttatcc     715
caaaatatat tattattatg ttgaatgtta aatatagtat ctatgtagat tggttagtaa    775
aactatttaa taaatttgat aaatataaaa aaaaaaaaca aaaaaaaaa                 825

<210> SEQ ID NO 24
<211> LENGTH: 156
<212> TYPE: PRT
<213> ORGANISM: Homo sapiens

<400> SEQUENCE: 24
```

-continued

```
Met Tyr Arg Met Gln Leu Leu Ser Cys Ile Ala Leu Ile Leu Ala Leu
 1               5                   10                  15

Val Thr Asn Ser Ala Pro Thr Ser Ser Thr Lys Thr Lys Lys
             20                  25                  30

Thr Gln Leu Gln Leu Glu His Leu Leu Asp Leu Gln Met Ile Leu
             35                  40                  45

Asn Gly Ile Asn Asn Tyr Lys Asn Pro Lys Leu Thr Arg Met Leu Thr
 50                          55                  60

Phe Lys Phe Tyr Met Pro Lys Lys Ala Thr Glu Leu Lys Gln Leu Gln
 65                  70                  75                  80

Cys Leu Glu Glu Glu Leu Lys Pro Leu Glu Glu Val Leu Asn Leu Ala
                 85                  90                  95

Gln Ser Lys Asn Phe His Leu Arg Pro Arg Asp Leu Ile Ser Asn Ile
                100                 105                 110

Asn Val Ile Val Leu Glu Leu Lys Gly Ser Glu Thr Thr Phe Met Cys
            115                 120                 125

Glu Tyr Ala Asp Glu Thr Ala Thr Ile Val Glu Phe Leu Asn Arg Trp
 130                 135                 140

Ile Thr Phe Cys Gln Ser Ile Ile Ser Thr Leu Thr
145                 150                 155
```

<210> SEQ ID NO 25
<211> LENGTH: 975
<212> TYPE: DNA
<213> ORGANISM: Homo sapiens
<220> FEATURE:
<221> NAME/KEY: CDS
<222> LOCATION: (1)..(972)

<400> SEQUENCE: 25

```
atg ttc ccc agc cct gct ctc acg ccc acg ccc ttc tca gtc aaa gac      48
Met Phe Pro Ser Pro Ala Leu Thr Pro Thr Pro Phe Ser Val Lys Asp
 1               5                   10                  15 atc cta aac ctg gag cag cag cag cgc agc ctg gct gcc gcc gga gag      96
Ile Leu Asn Leu Glu Gln Gln Gln Arg Ser Leu Ala Ala Ala Gly Glu
             20                  25                  30 ctc tct gcc cgc ctg gag gcg acc ctg gcg ccc tcc tcc tgc atg ctg     144
Leu Ser Ala Arg Leu Glu Ala Thr Leu Ala Pro Ser Ser Cys Met Leu
         35                  40                  45 gcc gcc ttc aag cca gag gcc tac gct ggg ccc gag gcg gct gcg ccg     192
Ala Ala Phe Lys Pro Glu Ala Tyr Ala Gly Pro Glu Ala Ala Ala Pro
 50                  55                  60 ggc ctc cca gag ctg cgc gca gag ctg ggc cgc gcg cct tca ccg gcc     240
Gly Leu Pro Glu Leu Arg Ala Glu Leu Gly Arg Ala Pro Ser Pro Ala
 65                  70                  75                  80 aag tgt gcg tct gcc ttt ccc gcc gcc ccc gcc ttc tat cca cgt gcc     288
Lys Cys Ala Ser Ala Phe Pro Ala Ala Pro Ala Phe Tyr Pro Arg Ala
                 85                  90                  95 tac agc gac ccc gac cca gcc aag gac cct aga gcc gaa aag aaa gag     336
Tyr Ser Asp Pro Asp Pro Ala Lys Asp Pro Arg Ala Glu Lys Lys Glu
                100                 105                 110 ctg tgc gcg ctg cag aag gcg gtg gag ctg gag aag aca gag gcg gac     384
Leu Cys Ala Leu Gln Lys Ala Val Glu Leu Glu Lys Thr Glu Ala Asp
            115                 120                 125 aac gcg gag cgg ccc cgg gcg cga cgg cgg agg aag ccg cgc gtg ctc     432
Asn Ala Glu Arg Pro Arg Ala Arg Arg Arg Arg Lys Pro Arg Val Leu
130                 135                 140 ttc tcg cag gcg cag gtc tat gaa ctg gag cgg cgc ttc aag caa cag     480
```

-continued

```
            Phe Ser Gln Ala Gln Val Tyr Glu Leu Glu Arg Arg Phe Lys Gln Gln
            145                 150                 155                 160 cgg tac ctg tcg gcc ccc gaa cgc gac cag ctg gcc agc gtg ctg aaa        528
Arg Tyr Leu Ser Ala Pro Glu Arg Asp Gln Leu Ala Ser Val Leu Lys
                165                 170                 175 ctc acg tcc acg cag gtc aag atc tgg ttc cag aac cgg cgc tac aag        576
Leu Thr Ser Thr Gln Val Lys Ile Trp Phe Gln Asn Arg Arg Tyr Lys
            180                 185                 190 tgc aag cgg cag cgg cag gac cag act ctg gag ctg gtg ggg ctg ccc        624
Cys Lys Arg Gln Arg Gln Asp Gln Thr Leu Glu Leu Val Gly Leu Pro
        195                 200                 205 ccg ccg ccg ccg ccg cct gcc cgc agg atc gcg gtg cca gtg ctg gtg        672
Pro Pro Pro Pro Pro Ala Arg Arg Ile Ala Val Pro Val Leu Val
    210                 215                 220 cgc gat ggc aag cca tgc cta ggg gac tcg gcg ccc tac gcg cct gcc        720
Arg Asp Gly Lys Pro Cys Leu Gly Asp Ser Ala Pro Tyr Ala Pro Ala
225                 230                 235                 240 tac ggc gtg ggc ctc aat ccc tac ggt tat aac gcc tac ccc gcc tat        768
Tyr Gly Val Gly Leu Asn Pro Tyr Gly Tyr Asn Ala Tyr Pro Ala Tyr
                245                 250                 255 ccg ggt tac ggc ggc gcg gcc tgc agc cct ggc tac agc tgc act gcc        816
Pro Gly Tyr Gly Gly Ala Ala Cys Ser Pro Gly Tyr Ser Cys Thr Ala
            260                 265                 270 gct tac ccc gcc ggg cct tcc cca gcg cag ccg gcc act gcc gcc gcc        864
Ala Tyr Pro Ala Gly Pro Ser Pro Ala Gln Pro Ala Thr Ala Ala Ala
        275                 280                 285 aac aac aac ttc gtg aac ttc ggc gtc ggg gac ttg aat gcg gtt cag        912
Asn Asn Asn Phe Val Asn Phe Gly Val Gly Asp Leu Asn Ala Val Gln
    290                 295                 300 agc ccc ggg att ccg cag agc aac tcg gga gtg tcc acg ctg cat ggt        960
Ser Pro Gly Ile Pro Gln Ser Asn Ser Gly Val Ser Thr Leu His Gly
305                 310                 315                 320 atc cga gcc tgg tag                                                    975
Ile Arg Ala Trp <210> SEQ ID NO 26
<211> LENGTH: 324
<212> TYPE: PRT
<213> ORGANISM: Homo sapiens

<400> SEQUENCE: 26

Met Phe Pro Ser Pro Ala Leu Thr Pro Thr Pro Phe Ser Val Lys Asp
1               5                   10                  15

Ile Leu Asn Leu Glu Gln Gln Gln Arg Ser Leu Ala Ala Ala Gly Glu
            20                  25                  30

Leu Ser Ala Arg Leu Glu Ala Thr Leu Ala Pro Ser Ser Cys Met Leu
        35                  40                  45

Ala Ala Phe Lys Pro Glu Ala Tyr Ala Gly Pro Glu Ala Ala Ala Pro
    50                  55                  60

Gly Leu Pro Glu Leu Arg Ala Glu Leu Gly Arg Ala Pro Ser Pro Ala
65                  70                  75                  80

Lys Cys Ala Ser Ala Phe Pro Ala Ala Pro Ala Phe Tyr Pro Arg Ala
                85                  90                  95

Tyr Ser Asp Pro Asp Pro Ala Lys Asp Pro Arg Ala Glu Lys Lys Glu
            100                 105                 110

Leu Cys Ala Leu Gln Lys Ala Val Glu Leu Glu Lys Thr Glu Ala Asp
        115                 120                 125

Asn Ala Glu Arg Pro Arg Ala Arg Arg Arg Arg Lys Pro Arg Val Leu
```

-continued

```
           130                 135                 140
Phe Ser Gln Ala Gln Val Tyr Glu Leu Glu Arg Arg Phe Lys Gln Gln
145                 150                 155                 160

Arg Tyr Leu Ser Ala Pro Glu Arg Asp Gln Leu Ala Ser Val Leu Lys
                165                 170                 175

Leu Thr Ser Thr Gln Val Lys Ile Trp Phe Gln Asn Arg Arg Tyr Lys
            180                 185                 190

Cys Lys Arg Gln Arg Gln Asp Gln Thr Leu Glu Leu Val Gly Leu Pro
        195                 200                 205

Pro Pro Pro Pro Pro Ala Arg Arg Ile Ala Val Pro Val Leu Val
210                 215                 220

Arg Asp Gly Lys Pro Cys Leu Gly Asp Ser Ala Pro Tyr Ala Pro Ala
225                 230                 235                 240

Tyr Gly Val Gly Leu Asn Pro Tyr Gly Tyr Asn Ala Tyr Pro Ala Tyr
                245                 250                 255

Pro Gly Tyr Gly Gly Ala Ala Cys Ser Pro Gly Tyr Ser Cys Thr Ala
            260                 265                 270

Ala Tyr Pro Ala Gly Pro Ser Pro Ala Gln Pro Ala Thr Ala Ala Ala
        275                 280                 285

Asn Asn Asn Phe Val Asn Phe Gly Val Gly Asp Leu Asn Ala Val Gln
290                 295                 300

Ser Pro Gly Ile Pro Gln Ser Asn Ser Gly Val Ser Thr Leu His Gly
305                 310                 315                 320

Ile Arg Ala Trp
```

<210> SEQ ID NO 27
<211> LENGTH: 980
<212> TYPE: DNA
<213> ORGANISM: Homo sapiens
<220> FEATURE:
<221> NAME/KEY: CDS
<222> LOCATION: (221)..(727)

<400> SEQUENCE: 27

```
cagccagtgc aactcagccg gctgcctctt cgacggcttt gactgccagc gtgcggaagg      60
ccagtgcaac ccctgtacg accagtactg caaggaccac ttcagcgacg ggcactgcga     120
ccagggctgc aacagcgcgg agtgcgagtg ggacgggctg gactgtgcgg agcatgtacc     180
cgagaggctg gcggccggca cgctggtggt ggtggtgctg atg ccg ccg gag cag      235
                                              Met Pro Pro Glu Gln
                                               1               5 ctg cgc aac agc tcc ttc cac ttc ctg cgg gag ctc agc cgc gtg ctg      283
Leu Arg Asn Ser Ser Phe His Phe Leu Arg Glu Leu Ser Arg Val Leu
             10                  15                  20 cac acc aac gtg gtc ttc aag cgt gac gca cac ggc cag cag atg atc      331
His Thr Asn Val Val Phe Lys Arg Asp Ala His Gly Gln Gln Met Ile
         25                  30                  35 ttc ccc tac tac ggc cgc gag gag gag ctg cgc aag cac ccc atc aag      379
Phe Pro Tyr Tyr Gly Arg Glu Glu Glu Leu Arg Lys His Pro Ile Lys
     40                  45                  50 cgt gcc gcc gag ggc tgg gcc gca cct gac gcc ctg ctg ggc cag gtg      427
Arg Ala Ala Glu Gly Trp Ala Ala Pro Asp Ala Leu Leu Gly Gln Val
 55                  60                  65 aag gcc tcg ctg ctc cct ggt ggc agc gag ggt ggg cgg cgg cgg agg      475
Lys Ala Ser Leu Leu Pro Gly Gly Ser Glu Gly Gly Arg Arg Arg Arg
 70                  75                  80                  85 gag ctg gac ccc atg gac gtc cgc ggc tcc atc gtc tac ctg gag att      523
Glu Leu Asp Pro Met Asp Val Arg Gly Ser Ile Val Tyr Leu Glu Ile
```

```
                                            -continued

Glu Leu Asp Pro Met Asp Val Arg Gly Ser Ile Val Tyr Leu Glu Ile
             90                  95                 100 gac aac cgg cag tgt gtg cag gcc tcc tcg cag tgc ttc cag agt gcc        571
Asp Asn Arg Gln Cys Val Gln Ala Ser Ser Gln Cys Phe Gln Ser Ala
            105                 110                 115 acc gac gtg gcc gca ttc ctg gga gcg ctc gcc tcg ctg ggc agc ctc        619
Thr Asp Val Ala Ala Phe Leu Gly Ala Leu Ala Ser Leu Gly Ser Leu
        120                 125                 130 aac atc ccc tac aag atc gag gcc gtg cag act cag tgc gag tgc agc        667
Asn Ile Pro Tyr Lys Ile Glu Ala Val Gln Thr Gln Cys Glu Cys Ser
    135                 140                 145 gat ttg aag ttg act aat cct cct tcc tta aag gag aaa aaa gta aaa        715
Asp Leu Lys Leu Thr Asn Pro Pro Ser Leu Lys Glu Lys Lys Val Lys
150                 155                 160                 165 gcc gtc tcc aga tagagtcggc tggtgcagga gagaatttag cgatagtttg            767
Ala Val Ser Arg caattctgat taatcgcgta gaaaatgacc ttatttttgga gggcgggatg gaggagagtg     827
ggtgaggagg cgcccggacg cggagccagt ccgccgcccc ccggccacca gcctgctgcg     887
tagccgctgc ctgatgtccg ggcacctgcc cctggccccc gtgcccgcag gtgagaccgt     947
ggagccgccc ccgccggcgc agctgcactt cat                                  980

<210> SEQ ID NO 28
<211> LENGTH: 169
<212> TYPE: PRT
<213> ORGANISM: Homo sapiens

<400> SEQUENCE: 28

Met Pro Pro Glu Gln Leu Arg Asn Ser Ser Phe His Phe Leu Arg Glu
  1               5                  10                  15

Leu Ser Arg Val Leu His Thr Asn Val Val Phe Lys Arg Asp Ala His
             20                  25                  30

Gly Gln Gln Met Ile Phe Pro Tyr Tyr Gly Arg Glu Glu Leu Arg
         35                  40                  45

Lys His Pro Ile Lys Arg Ala Ala Glu Gly Trp Ala Ala Pro Asp Ala
     50                  55                  60

Leu Leu Gly Gln Val Lys Ala Ser Leu Leu Pro Gly Gly Ser Glu Gly
 65                  70                  75                  80

Gly Arg Arg Arg Arg Glu Leu Asp Pro Met Asp Val Arg Gly Ser Ile
                 85                  90                  95

Val Tyr Leu Glu Ile Asp Asn Arg Gln Cys Val Gln Ala Ser Ser Gln
            100                 105                 110

Cys Phe Gln Ser Ala Thr Asp Val Ala Ala Phe Leu Gly Ala Leu Ala
        115                 120                 125

Ser Leu Gly Ser Leu Asn Ile Pro Tyr Lys Ile Glu Ala Val Gln Thr
    130                 135                 140

Gln Cys Glu Cys Ser Asp Leu Lys Leu Thr Asn Pro Pro Ser Leu Lys
145                 150                 155                 160

Glu Lys Lys Val Lys Ala Val Ser Arg
                165

<210> SEQ ID NO 29
<211> LENGTH: 2826
<212> TYPE: DNA
<213> ORGANISM: Homo sapiens
<220> FEATURE:
<221> NAME/KEY: CDS
<222> LOCATION: (184)..(618)
```

<400> SEQUENCE: 29

```
gagagggccc ggactagggg cggcgggcac cgcaggagct ccgcgcggct gcagcgcggg      60
cgggagcggg gacgcgatgt cgccgccgcc gcctccttgc gggccggggc tgcgcctccg     120
gggctgagcc gccgccagag ccgacagccg agcagccgct gggcgctccc gcggcgcagg     180 agg atg ggc tgc ggc ggg agc cgg gcg gat gcc atc gag ccc cgc tac      228
    Met Gly Cys Gly Gly Ser Arg Ala Asp Ala Ile Glu Pro Arg Tyr
    1               5                   10                  15 tac gag agc tgg acc cgg gag aca gaa tcc acc tgg ctc acc tac acc      276
Tyr Glu Ser Trp Thr Arg Glu Thr Glu Ser Thr Trp Leu Thr Tyr Thr
                20                  25                  30 gac tcg gac gcg ccg ccc agc gcc gcc gcc ccg gac agc ggc ccc gaa      324
Asp Ser Asp Ala Pro Pro Ser Ala Ala Ala Pro Asp Ser Gly Pro Glu
            35                  40                  45 gcg ggc ggc ctg cac tcg ggc atg ctg gaa gat gga ctg ccc tcc aat      372
Ala Gly Gly Leu His Ser Gly Met Leu Glu Asp Gly Leu Pro Ser Asn
        50                  55                  60 ggt gtg ccc cga tct aca gcc cca ggt gga ata ccc aac cca gag aag      420
Gly Val Pro Arg Ser Thr Ala Pro Gly Gly Ile Pro Asn Pro Glu Lys
65                  70                  75 aag acg aac tgt gag acc cag tgc cca aat ccc cag agc ctc agc tca      468
Lys Thr Asn Cys Glu Thr Gln Cys Pro Asn Pro Gln Ser Leu Ser Ser
80                  85                  90                  95 ggc cct ctg acc cag aaa cag aat ggc ctt cag acc aca gag gct aaa      516
Gly Pro Leu Thr Gln Lys Gln Asn Gly Leu Gln Thr Thr Glu Ala Lys
                100                 105                 110 aga gat gct aag aga atg cct gca aaa gaa gtc acc att aat gta aca      564
Arg Asp Ala Lys Arg Met Pro Ala Lys Glu Val Thr Ile Asn Val Thr
            115                 120                 125 gat agc atc caa cag atg gac aga agt cga aga atc aca aag aac tgt      612
Asp Ser Ile Gln Gln Met Asp Arg Ser Arg Arg Ile Thr Lys Asn Cys
        130                 135                 140 gtc aac tagcagagag tccaagcaga agggcagatg gacttcttca gtgtccttca       668
Val Asn
    145 cggcactgga tcccatcaaa gaaccttgaa gaagtggctg ccccttgctg gacctgaatt     728 ctactgagtc cctggcaaga ccgtcttacc tggcagcaaa ctgctgcctg atttgttggg     788 accttctgag cctctactt atcatgtaaa tgtattggca cagtgcttac atatgttaat      848 aaactgcaaa tgtgcagttc agtttgtctc tttgcaactc ctgtaatacg gtctggtgta     908 aaagtagtga gttaaagcta caggtcagtt tatgaaacag aaaagtagga atgcattttc     968 tgggtgaaag agtcacacct tagtgctata actctcctgc ccatgatagt gtattctgtt    1028 tcaggcaagc ttattctttc cttccttcat tttaaatatt gtcattacaa atcttaccag    1088 gttcacttaa aagctggctt tcatccaact ctaaacccac atattgaaaa atcaaggta     1148 caggaaaact ccttgttatc cttgtttcct tagcttggta tgagacagat cggatccagt    1208 ttcccatgca ccaacccact gcccatggca tgtctttggg aggtgtctgt gaagcagtca    1268 tacctgctcc tcatctgcct ggaaagtcct cctattccag tgtccatgtt ggcctccagt    1328 ccttaatgtc accatgcttg tggccaatgc atccaaataa ggatacccct cagggctcag    1388 ctagacattg caattttgca tagctttcca gttcccttg cttgtcttct tgactgtctt     1448 ccctctctac cggggtcact tgcaattgtt aatcaaagat tgaacactgc gtaggagagg    1508 gagatgatcc agagacatgt ggcagcaggc atggcttccc cttggcctct ctgtacactg    1568
```

```
cccaggact gtcatttttgg catctgcaaa ggaatcactt tagaaagcca gcacctggtt    1628
gatgtgtatt catactgaca ttagattgat gtgcactgca ttagaaatga ggtagctgac    1688
acagaaaaag gatgttttga taggaataat tttctagtat gtcttgaaac atgttcatct    1748
ggaagtattt tcctccaaag taatgtagca tgatttttca aggattgtta acatgcctgg    1808
gattgggaaa gataggacta aagttgtgcc aaactatatc aataaattcc atgtttagca    1868
gaaataggca gcctattggt gttatgttta tgtaacatag tccagagaac tgacatgcag    1928
gtcaaaagtc agatacgcaa cctccttatc tgctaactct gttattcttc aaacacaagt    1988
gggtagtgtc attttttcctt ccttccttcc attggcagat tgtatattta ttcacaaaac    2048
attaaatgtc catcctgtgc caggtactat gcagatgttg agggatttgg ggtctggtta    2108
gtcgtgacta tctatcctga atctaacagt gacttcataa ctaggagact gaattagacc    2168
cttaaggtat agtgtgtgtt gcaaatcact ctgcaatgga aacttttata ttcagggtag    2228
gtttgtgtct taaactaggt gttctaatca atgtacaaga cttaccata cacgcaacta    2288 tagttttttct aaaccttcat cattttgtga ttctttgaga aagggctttt aggaacttta    2348
tgttctaaaa aatgttttta acaataataa gataaaagaa aaacctgtga ttcatatgtc    2408
cccactggca ttactcagca ggagccccca gctgccaaag gttggcagtg atcctgcaag    2468
ttcaagggct ctttctccct ggggatgtgc tttgtggctt ctctttacag ctttgtttct    2528
gcatcagttc actgctgcat gttgtttgga atttatcacc ttaagaaagt gtctctgttt    2588
tatatagaaa cactttctca cttacagggg agaaggaaat gcagggcaca tgatctggcc    2648
ctccccagaa caatctggat ttcacggaga cagcaaccag aagttaaacc atgtgactaa    2708
aaatgcatct ggctactttt tcatgtatgt atgagacaga aactaatcct tactatccta    2768
ttaggatacc acttttcatt gcaaagtttg tgtcaataaa gtcattaatt ttaaacat    2826
```

<210> SEQ ID NO 30
<211> LENGTH: 145
<212> TYPE: PRT
<213> ORGANISM: Homo sapiens

<400> SEQUENCE: 30

```
Met Gly Cys Gly Gly Ser Arg Ala Asp Ala Ile Glu Pro Arg Tyr Tyr
 1               5                  10                  15

Glu Ser Trp Thr Arg Glu Thr Glu Ser Thr Trp Leu Thr Tyr Thr Asp
            20                  25                  30

Ser Asp Ala Pro Pro Ser Ala Ala Pro Asp Ser Gly Pro Glu Ala
        35                  40                  45

Gly Gly Leu His Ser Gly Met Leu Glu Asp Gly Leu Pro Ser Asn Gly
    50                  55                  60

Val Pro Arg Ser Thr Ala Pro Gly Gly Ile Pro Asn Pro Glu Lys Lys
65                  70                  75                  80

Thr Asn Cys Glu Thr Gln Cys Pro Asn Pro Gln Ser Leu Ser Ser Gly
                85                  90                  95

Pro Leu Thr Gln Lys Gln Asn Gly Leu Gln Thr Thr Glu Ala Lys Arg
            100                 105                 110

Asp Ala Lys Arg Met Pro Ala Lys Glu Val Thr Ile Asn Val Thr Asp
        115                 120                 125

Ser Ile Gln Gln Met Asp Arg Ser Arg Arg Ile Thr Lys Asn Cys Val
    130                 135                 140

Asn
145
```

<210> SEQ ID NO 31
<211> LENGTH: 1027
<212> TYPE: DNA
<213> ORGANISM: Influenza virus

<400> SEQUENCE: 31

```
agcgaaagca ggtagatatt gaaagatgag tcttctaacc gaggtcgaaa cgtacgttct      60
ctctatcatc ccgtcaggcc ccctcaaagc cgagatcgca cagagacttg aagatgtctt     120
tgcagggaag aacaccgatc ttgaggttct catggaatgg ctaaagacaa gaccaatcct     180
gtcacctctg actaagggga ttttaggatt tgtgttcacg ctcaccgtgc ccagtgagcg     240
aggactgcag cgtagacgct ttgtccaaaa tgcccttaat gggacgggga tccaaataa      300
catggacaaa gcagttaaac tgtataggaa gctcaagagg gagataacat tccatggggc     360
caaagaaatc tcactcagtt attctgctgg tgcacttgcc agttgtatgg cctcatata     420
caacaggatg ggggctgtga ccactgaagt ggcatttggc ctggtatgtg caacctgtga     480
acagattgct gactcccagc atcggtctca taggcaaatg gtgacaacaa ccaacccact     540
aatcagacat gagaacagaa tggttttagc cagcactaca gctaaggcta tggagcaaat     600
ggctggatcg agtgagcaag cagcagaggc catggaggtt gctagtcagg ctaggcaaat     660
ggtgcaagcg atgagaacca ttgggactca tcctagctcc agtgctggtc tgaaaaatga     720
tcttcttgaa aatttgcagg cctatcagaa acgaatgggg gtgcagatgc aacggttcaa     780
gtgatcctct cgctattgcc gcaaatatca ttgggatctt gcacttgata ttgtggattc     840
ttgatcgtct tttttcaaa tgcatttacc gtcgctttaa atacggactg aaaggagggc     900
cttctacgga aggagtgcca agtctatga gggaagaata tcgaaggaa cagcagagtg     960
ctgtggatgc tgacgatggt catttttgtca gcatagagct ggagtaaaaa actaccttgt    1020
ttctact                                                                1027
```

<210> SEQ ID NO 32
<211> LENGTH: 9
<212> TYPE: PRT
<213> ORGANISM: Influenza virus

<400> SEQUENCE: 32

Gly Ile Leu Gly Phe Val Phe Thr Leu
 1               5

<210> SEQ ID NO 33
<211> LENGTH: 10
<212> TYPE: PRT
<213> ORGANISM: Influenza virus

<400> SEQUENCE: 33

Tyr Met Leu Asp Leu Gln Pro Glu Thr Thr
 1               5                  10

<210> SEQ ID NO 34
<211> LENGTH: 9
<212> TYPE: PRT
<213> ORGANISM: Homo sapiens

<400> SEQUENCE: 34

Ala Ala Gly Ile Gly Ile Leu Thr Val
 1               5

TRANSFECTION OF EUKARYONTIC CELLS WITH LINEAR POLYNUCLEOTIDES BY ELECTROPORATION

This application claims priority of U.S. Provisional Application No. 60/299,817, which was filed on Jun. 21, 2001.

The present invention provides an improved method for gene delivery in eukaryotic cells by electroporation, preferably in human hematopoietic cells, particular dendritic cells. The method of the invention is superior to lipofection and passive pulsing of mRNA and to electroporation of plasmid cDNA for gene delivery, including tumor antigen loading of dendritic cells.

BACKGROUND OF THE INVENTION

Dendritic cells (DC) are bone-marrow-derived leukocytes that function as professional antigen-capturing and -presenting cells for the initiation of a primary immune response in vitro and in vivo (Banchereau, J., Steinman, R. M., Nature, 392:245-252 (1998)). Given their central role in cell-mediated immunity in vivo, they represent highly attractive targets for molecular immunotherapy of acquired diseases, such as AIDS and cancer. Recent advances in the ex vivo generation of DC and the ability to modulate DC functions provide a rationale to design DC-based tumor vaccines (Avigan, D., Blood Rev., 13:51-64 (1999)). The outcome of such tumor vaccines will highly depend on the efficacy of the applied antigen-loading method for optimal stimulation of cytotoxic T lymphocytes (CTL)-mediated anti-tumor immune responses (Tarte, K., Klein, B., Leukemia, 13:653-663 (1999)). Although several reports have documented viral transfer of cDNA encoding tumor-associated antigens to load DC for induction of TAA-specific cytotoxic T lymphocytes (CTL) (Dietz, A. B., Vuk, P. S., Blood, 91:392-398 (1998); Brossart, P. et al., J. Immunol., 158:3270-3276 (1997); Specht, J. M. et al., J. Exp. Med., 186:1213-1221 (1997)) nonviral gene delivery systems for DC-based vaccines would provide a more attractive approach with clinical perspectives since safety issues and immunogenicity of the vector are reduced to a minimum.

Furthermore, it is generally known that nonviral DNA transfection methods are inefficient, particularly in nondividing cells, as there is only very limited DNA trafficking to the nucleus where transcription occurs (Luo, D., Saltzman, W. M., Nat. Biotechnol., 18:33-37 (2000)). Therefore, several groups demonstrated the feasibility of mRNA transfection as a valid alternative for nonviral gene delivery, since this strategy avoids the need for entry into the nucleus as well as the complex issues of transcriptional regulation associated with DNA vectors (Lu, D. et al., Cancer Gene Ther., 1:245-252 (1994); Kariko, K. et al., Biochim. Biophys. Acta, 1369:320-334 (1998); Sawai, K. et al., Mol. Genet. Metab., 64:44-51 (1998)). The RNA approach has several advantages that render it attractive in developing DC-based tumor vaccines. First, DC can be transfected to comparable levels as compared to transduction by recombinant viruses, such as poxviruses Kim, C. J. et al., J. Immunother., 20:276-286 (1997)) or adenoviruses (Dietz, A. B., Vuk, P. S., Blood, 91:392-398 (1998)), while circumventing the drawbacks of viral vectors (Jenne, L. et al., Gene Ther., 7:1575-1583 (2000); Jonuleit, H. et al., Gene Ther., 7:249-254 (2000)). Second, DC can be charged with the full antigenic spectrum using total mRNA instead of IVT mRNA as a source of tumor antigens without prior identification of tumor-associated antigens (Zhang, W. et al., Hum. Gene Ther., 10:1151-1161 (1999)). Moreover, RNA has a short cellular half-life and lacks the potential to integrate into the host genome, thereby obviating safety concerns, e.g. insertional mutagenesis, in the context of clinical gene therapy trials (Lu, D. et al., Cancer Gene Ther., 1:245-252 (1994); Ying, H. et al., Nat. med., 5:823-827 (1999)). On the other hand this short cellular half-life may be disadvantageous since it may result in a relatively short protein expression.

However, the problem of inefficient gene transfer and low level of expression by nonviral transfection remains (Arthur, J. F. et al., Cancer Gene Ther., 4:17-25 (1997)).

Previously, we reported high-level transgene expression in proliferating $CD34^+$ progenitor-derived DC (34-DC) and Langerhans cells (34-LC) using electroporation-mediated gene delivery (Van Tendeloo, V. F. I. et al., Gene Ther., 5:700-707 (1998)). In contrast, nondividing monocyte-derived DC (Mo-DC), which represent a highly accessible and widely used source of in vitro cultured DC, were relatively refractory to cDNA transfection techniques, either by electroporation or by lipofection.

Recently, it was shown that human DC could be transfected with RNA and were capable of inducing primary antigen-specific CTL (Nair, S. K. et al., Nat. Biotechnol., 16:364-369 (1998)). However, there are very few data on efficiency of mRNA transfer in Mo-DC using passive pulsing, lipofection or electroporation, if at all. Furthermore, the feasibility of mRNA transfection in 34-DC or 34-LC has not yet been established, let alone that the method has been adapted to Mo-DC.

Electroporation methods for the integration of cyclic polynucleic acids into "normal" cells (such as tumor cells) are generally use the following reaction conditions (Van Tendeloo V. F. I et al., Gene Ther. 5:700-707 (1998); Van Tendeloo, V. F. I. et al., Gene Ther. 7:1431-1437 (2000); Van Bockstaele, D., Berneman, Z. N., Cytometry 41:31-35 (2000); Lurquin, P. F., Mol. Biotechnol. 7:5-35 (1997); Matthews, K. E. et al., Mol. Biotechnol., vol 48, Chapter 22, Ed.Nickoloff); Spencer, S. C., Biochem. and Biotechnol. 42:75-82 (1993)):

a cell concentration in the range of 1 to $10 \times 10^6$ cell/ml a voltage in the range of 200-350 V a capacitance of greater than 300 µF a pulse length in the range of 15 to 40 µs However such "conventional" electroporation methods give only very poor RNA transfection yields if applied to primary cells (such as Mo-DC) and/or if linear polynucleotides are electroporated as it was e.g. shown in Strobel, I. et al., Gene Therapy 7:2028-2035 (2000) where we reported on the electroporation of monocyte-derived dendritic cells and tested various "conventional" parameter settings: i) the cell density was tested in the range from $2 \times 10^6$-$4 \times 10^7$ cells/ml while capacitance and voltage were kept constant at 300 µF and 250V, respectively, showing that an increased cell density resulted in a decreased mortality; ii) the impact of the voltage was investigated in the range from 250-350 V, while capacitance and cell density were kept constant at 300 µF and $4 \times 10^7$ cells/ml, respectively, demonstrating that an increasing voltage resulted in a higher mortality; iii) the capacitance was evaluated in the range from 300-1500 µF while cell density and voltage were kept constant at $4 \times 10^7$ cells/ml and 250 V, respectively. Increasing capacitance yielded in an increased mortality. Although pulse times below 22 ms increased the cell viability, only a very low heterologous gene expression was detectable. In contrast pulse times above 28 ms increased transient gene expression but resulted in a high cell loss. In conclusion, the optimal electroporation conditions for immature monocyte-derived DC were found in this previously published work as follows: i.) cell density of 4×10$^7$ cells/ml; ii.) voltage of 250 V; iii.) capacitance of 300-500 µF and iv.) pulse times between 22-28 ms. Using these optimised electroporation conditions up to 11% of DC were GFP$^+$ after 48 h, when GFP RNA was transfected. A similar transfection efficacy was obtained using GFP DNA.

Recently we also reported that effective electroporation of in vitro transcribed mRNA into monocyte-derived dendritic cells is possible, but did not mention how this electroporation can be achieved (Poster at the 6$^{th}$ Symposium on dendritic cells, Port Douglas, Australia, May 26-Jun. 1, 2000 and at the Keystone Symposia, Taos, N. Mex., USA., Mar. 12-18, 2001).

U.S. Pat. No. 5,766,902 discloses an electroporation method for nucleic acid molecules, wherein the nucleic acid molecules are applied in or together with a ligand which binds to the target cell. Said complex may comprise an endosomal disruption agent.

U.S. Pat. No. 5,554,528 describes the use of plasmids (i.e., cyclic DNA constructs) containing a toxin gene under the control of HIV elements for stable transformation of cell lines in order to block HIV replication when cells are infected. Said patent mentions DNA transfection by electroporation (column 15, example 2) using electrical settings (250 µF; 220 to 290 V; 100 µl volumes, BioRad cuvettes and Gene Pulser®) which are not typical for plasmid electroporation, it does, however, not mention RNA transfection, let alone RNA electroporation. Furthermore, only "normal" mammalian cell lines are electroporated, primary cells are not contemplated.

SUMMARY OF THE INVENTION

It was now surprisingly found that with a particular electroporation setting hematopoietic cells such as monocyte derived dendritic cells can effectively be transfected with DNA and RNA. In particular, it was found out that the mRNA transfection efficiency was improved using an optimized mRNA-based electroporation. Thus, the present invention describes a method for high-efficiency non-viral transfection of Mo-DC as well as other types of dendritic cells (including CD34$^+$ derived Langerhans cells and interstitial type DC) by mRNA electroporation correlated with effective loading of tumor antigens into different types of human DC. The efficiency of the method of the present invention was compared with other transfection methods, such as lipofection and passive pulsing of mRNA as well as cDNA electroporation, and found to be highly superior. Furthermore, the effect of DC maturation on loading efficiency was investigated. An electroporation-based mRNA transfection protocol was developed which is suitable for highly efficient antigen loading in Mo-DC, as well as in 34-DC and 34-LC. This technique proved to be superior to mRNA lipofection or passive mRNA pulsing in terms of loading efficiency and subsequent activation of an antigen-specific CD8$^+$ CTL clone. With such mRNA-based electroporation, the transfection efficiency in Mo-DC, 34-DC and 34-LC was at least 25, 6 and 3 times, respectively, more efficient as compared to plasmid DNA electroporation described in van Tendeloo, V. F. I. et al., Gene Ther., 5:700-707 (1998), and also superior to previously described mRNA electroporation. Also, such mRNA electroporation was superior to mRNA lipofection and passive pulsing. This increased transfection efficiency was translated in a superior biological effect in vitro, as confirmed by our CTL activation experiments, and could be used as a tool to investigate as to whether it results in a higher immunopotency in vivo (Porgador, A. et al., J. Exp. Med., 188:1075-1082 (1998)). Importantly, mRNA-transfected DC were able to efficiently process the introduced antigen and present antigenic epitopes in an MHC class I-restricted manner to a specific CD8$^+$ TIL clone (FIG. 4). Furthermore, in concordance with previous reports on the effect of maturation on the antigen-presenting capacity of DC (Cella, M. et al., Curr. Opin. Immunol., 9:10-16 (1997)), antigen loading by mRNA electroporation was preferably performed prior to DC maturation in order to achieve the most optimal antigen presentation (FIG. 5), indicating the importance of the sequence of loading and DC maturation for future DC-based vaccine design (Morse, M. A. et al., Cancer Res., 58:2965-2968 (1998)).

The present invention thus provides (1) a method for transfection of eukaryotic cells with one or more or a mixture of linear polynucleotides, which method comprises electroporation of a suspension containing the eukaryotic cells and the linear polynucleotides to be transfected at a capacitance of below 300 µF;

(2) a method for transfection of eukaryotic cells with one or more or a mixture of linear polynucleotides, preferably a method as defined in (1), which method comprises electroporation of a suspension containing the eukaryotic cells and the linear polynucleotides to be transfected with a soft pulse at 300 to 600 V for 100 µs to 1 ms.

(3) the transfected eukaryotic cells obtainable by the method as defined in (1) or (2) above;

(4) a pharmaceutical composition or vaccine comprising transfected eukaryotic cells obtainable by the method as defined in (1) or (2) above;

(5) the use of the transfected eukaryotic cells obtainable by the method as defined in (1) or (2) above for preparing an agent for immunotherapy, including induction of immunity or tolerance, tumour therapy, stem cell therapy, regenerative medicine, or tissue engineering;

(6) the use of the transfected eukaryotic cells obtainable by the method as defined in (1) or (2) above as expression system for gene products encoded by the linear polynucleotides, or as detection system; and (7) a method for immunotherapy or tumour therapy which comprises administering transfected eukaryotic cells obtainable by the method as defined in (1) or (2) above to the patient.

The method of embodiments (1) and (2) are applicable for loading human dendritic cells (DC) with antigens such as tumor antigens, which is a challenging approach for DC-based tumor vaccines. (This is quite important, since in preliminary experiments it was found that the plasmid DNA electroporation approach is not applicable for tumor antigen loading of DC, because the T cell stimulation it provokes is indistinguishable from non-specific T cell stimulation mediated by plasmid DNA, either directly or indirectly. This non-specific stimulation was not observed when using mRNA electroporation, establishing the superiority of that technique for specific DC-based T cell stimulation.) Also, the expression of other proteins (e.g., stimulatory or tolerogenic or apoptotic molecules) in DC by gene transfer might be desired, furthermore the introduction of antisense RNA by electroporation. In other words, the present invention describes a cytoplasmic expression system based on mRNA electroporation to efficiently introduce genetic information into DC. Preliminary experiments in K562 cells using an enhanced green fluorescent protein (EGFP) reporter gene revealed that mRNA electroporation as compared to plasmid DNA electroporation showed a markedly improved transfection efficiency (89% versus 40% EGFP$^+$ cells, respectively) and induced a strikingly lower cell toxicity (15% death rate with mRNA versus 51% with plasmid DNA). Applying mRNA electroporation for nonviral transfection of different types of human DC, including monocyte-derived DC (Mo-DC), CD34+ progenitor-derived DC (34-DC) and Langerhans cells (34-LC), high-level transgene expression by mRNA electroporation was obtained in more than 50% of all DC types. mRNA-electroporated DC retained their phenotype and maturational potential. Importantly, DC electroporated with mRNA encoding Melan-A strongly activated a Melan-A-specific cytotoxic T lymphocyte (CTL) clone in an HLA-restricted manner and were superior to mRNA-lipofected or -pulsed DC. Optimal stimulation of the CTL occurred when Mo-DC underwent maturation following mRNA transfection. Strikingly, a nonspecific stimulation of CTL was observed when DC were transfected with plasmid DNA. Our data clearly demonstrate that Mo-DC electroporated with mRNA efficiently present functional antigenic peptides to cytotoxic T cells. Therefore, electroporation of mRNA encoding tumor antigens is a powerful technique to charge human dendritic cells with tumor antigens and could serve applications in future DC-based tumor vaccines. Transfection of ready mature DC was less efficient when maturation stimuli such as TNFα+LPS were used. The use of a certain generation methanol for Mo-DC including an optimized maturation stimulus (see Example 4) allowed, however, also for efficient transfection such as tumor antigens of mature Mo-DC. The invention is hereinafter described in more detail by the appended figures and the examples which are, however, not to be construed to limit the invention.

Figure 1A:
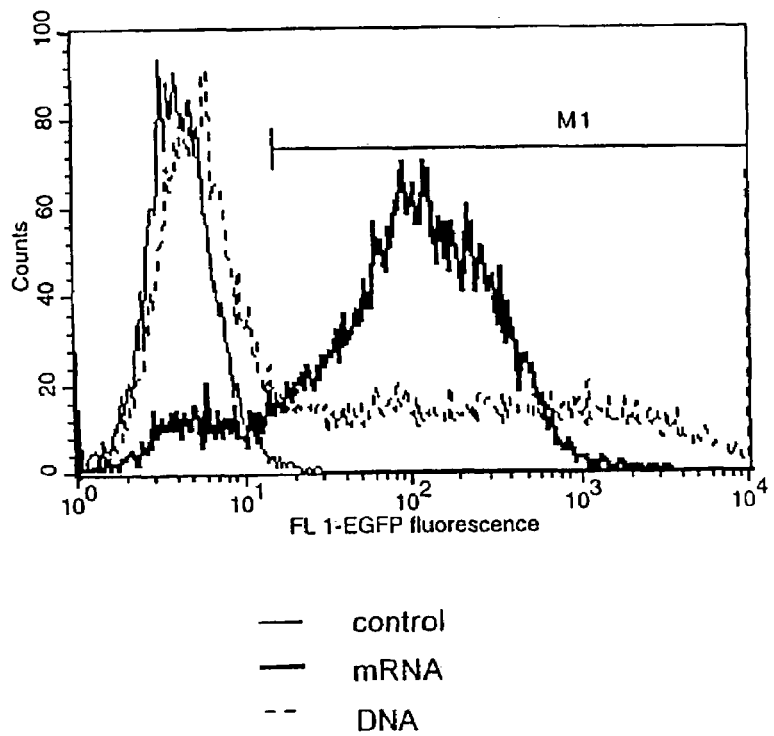
FIG. 1 shows the flow cytometric analysis of transgene expression in K562 cells following EGFP mRNA electroporation.

A: K562 cells were electroporated with EGFP mRNA at 300 V, 150 µF or with EGFP plasmid DNA at 260V, 1050 µF (dashed line) as described in the Examples. Twenty-four hours post-electroporation, flow cytometric (FCM) EGFP analysis was performed to estimate transfection efficiency of mRNA electroporation (bold line) and plasmid DNA electroporation (dashed line). An overlay histogram representative of five independent experiments is shown. Non-electroporated cells (thin line) were used to determine background fluorescence. The M1 region indicates the EGFP-positive cell fraction. The percentage of EGFP+ cells was 85% (bold line) and 50% (dashed line) following mRNA or plasmid DNA electroporation, respectively.

B: Kinetics of EGFP mRNA expression in K562 cells in function of time (n=3). Note the rapid induction of high-level EGFP expression already 3 hours following electroporation.

FIG. 2 shows the FCM analysis of transgene expression following EGFP mRNA transfection in different types of DC.

A: Immature Mo-DC were cultured with GM-CSF and IL-4 and transfected at day 6 of culture with control (Melan-A) or EGFP mRNA by lipofection (bottom) or electroporation (top) and analyzed by FCM one day after transfection. The dot plots show EGFP fluorescence on the x-axis and ethidium bromide staining on the y-axis. Gates were drawn based on control mRNA-lipofected or electroporated Mo-DC. Percentage of dead cells (upper left corner) and viable EGFP+ cells (lower right corner) is indicated. Results are representative of 8 independent experiments.

B: Monitoring of EGFP mRNA expression and cell viability in Mo-DC following mRNA electroporation in function of time (n=2).

C: 34-DC (bottom) and 34-LC (top) were cultured as described in Materials and Methods and transfected at day 12 and 25 of culture, respectively, with control (Melan-A) or EGFP mRNA by mRNA electroporation. FCM analysis was performed 24 h after mRNA electroporation. The dot plots show EGFP fluorescence on the x-axis and ethidium bromide staining on the y-axis. Gates were drawn based on control mRNA-electroporated Mo-DC (left). Percentage of dead cells (upper left corner) and viable EGFP+ cells (lower right corner) is indicated. Results are representative of 4 independent experiments.

FIG. 3 shows the phenotypical analysis and maturation potential of mRNA-electroporated DC.

A: Immature Mo-DC (iMo-CD) were transfected by electroporation with mRNA encoding EGFP and stained with phycoerythrin (PE)-labeled antibodies specific for CD1a, HLA-DR and CD86 one day after electroporation (bottom). Untransfected iMo-DC (top) served as controls and isotype-matched antibodies were used to set quadrants. Results are representative of 3 experiments.

B: iMo-DC were transfected by electroporation with mRNA encoding Melan-A and directly stained with a PE-labeled CD80 antibody (bottom) or indirectly stained with a CD83 antibody (top). A representative overlay histogram is shown in which the dashed line represents the control non-electroporated iMo-DC, the thin line the electroporated iMo-DC and the bold line represents electroporated iMo-DC that were allowed to mature for an additional 24 h following mRNA electroporation in the presence of TNF-α and LPS.

C: 12 day-cultured 34-DC were transfected by electroporation with mRNA encoding EGFP and stained with PE-labeled antibodies specific for CD1a, HLA-DR, CD86 and CD80 one day after electroporation (bottom). Untransfected 34-DC (top) served as controls and isotype-matched antibodies were used to set quadrants. Results are representative of 3 experiments.

Figure 4:
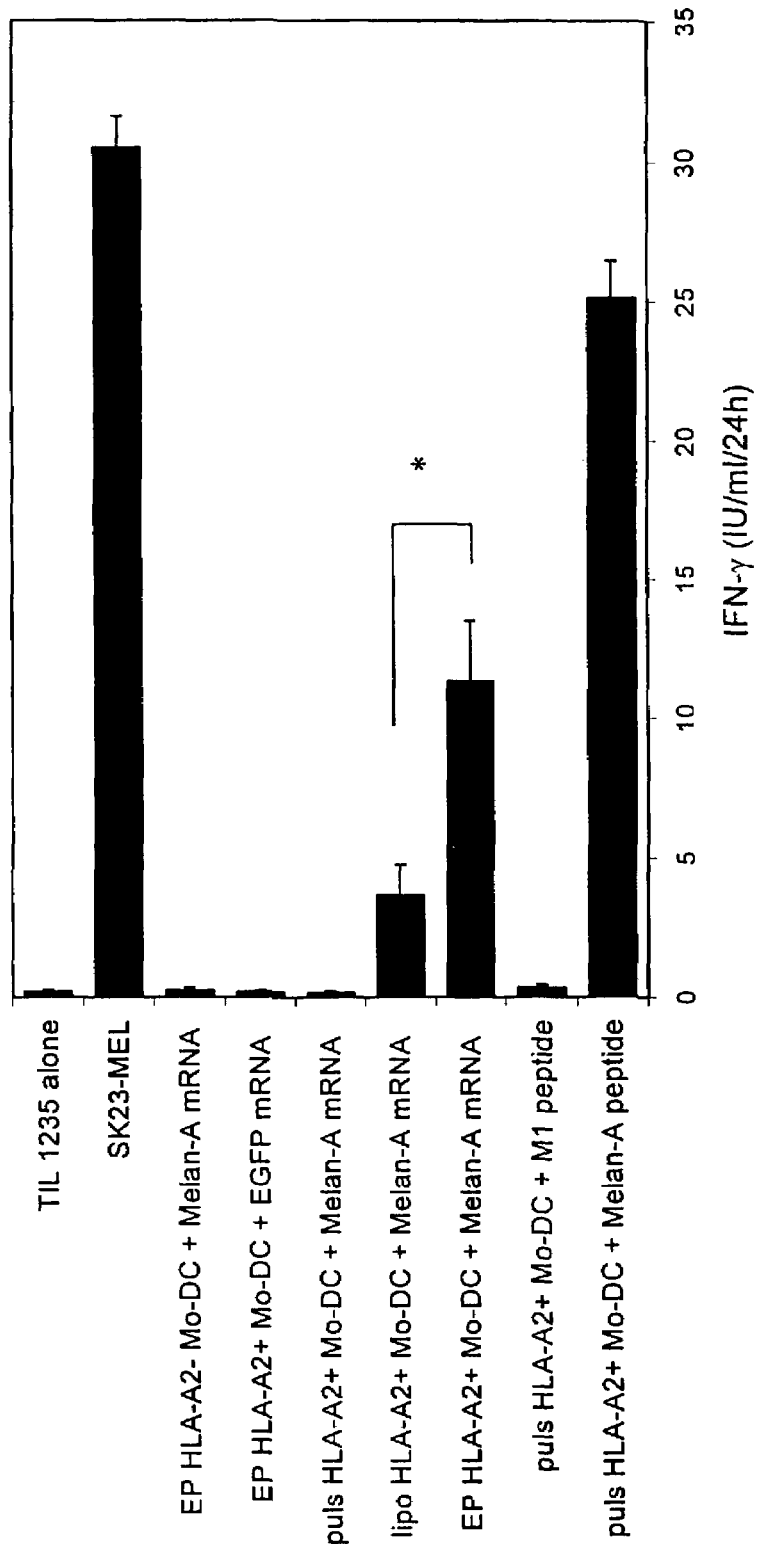

FIG. 4 shows the mRNA-based antigen loading of Mo-DC. Immature Mo-DC were cultured with GM-CSF and IL-4 and transfected at day 6 of culture with Melan-A mRNA by electroporation (n=11), lipofection (n=8) or passive pulsing (n=5) or with EGFP mRNA by electroporation (n=6). The SK23-MEL melanoma cell line, HLA-A2+ Mo-DC pulsed with a Melan-A or irrelevant influenza peptide and HLA-A2-negative Mo-DC electroporated with Melan-A mRNA served as controls. Antigen-presenting cells (indicated on the left of the graph) were co-incubated with a Melan-A specific CD8+ CTL clone to determine antigen loading efficiency, as reflected by IFN-γ production of the CTL clone. Results are shown as mean±SD. *P<0.05; EP=electroporation; lipo=lipofection; puls=passive pulsing.

Figure 5:
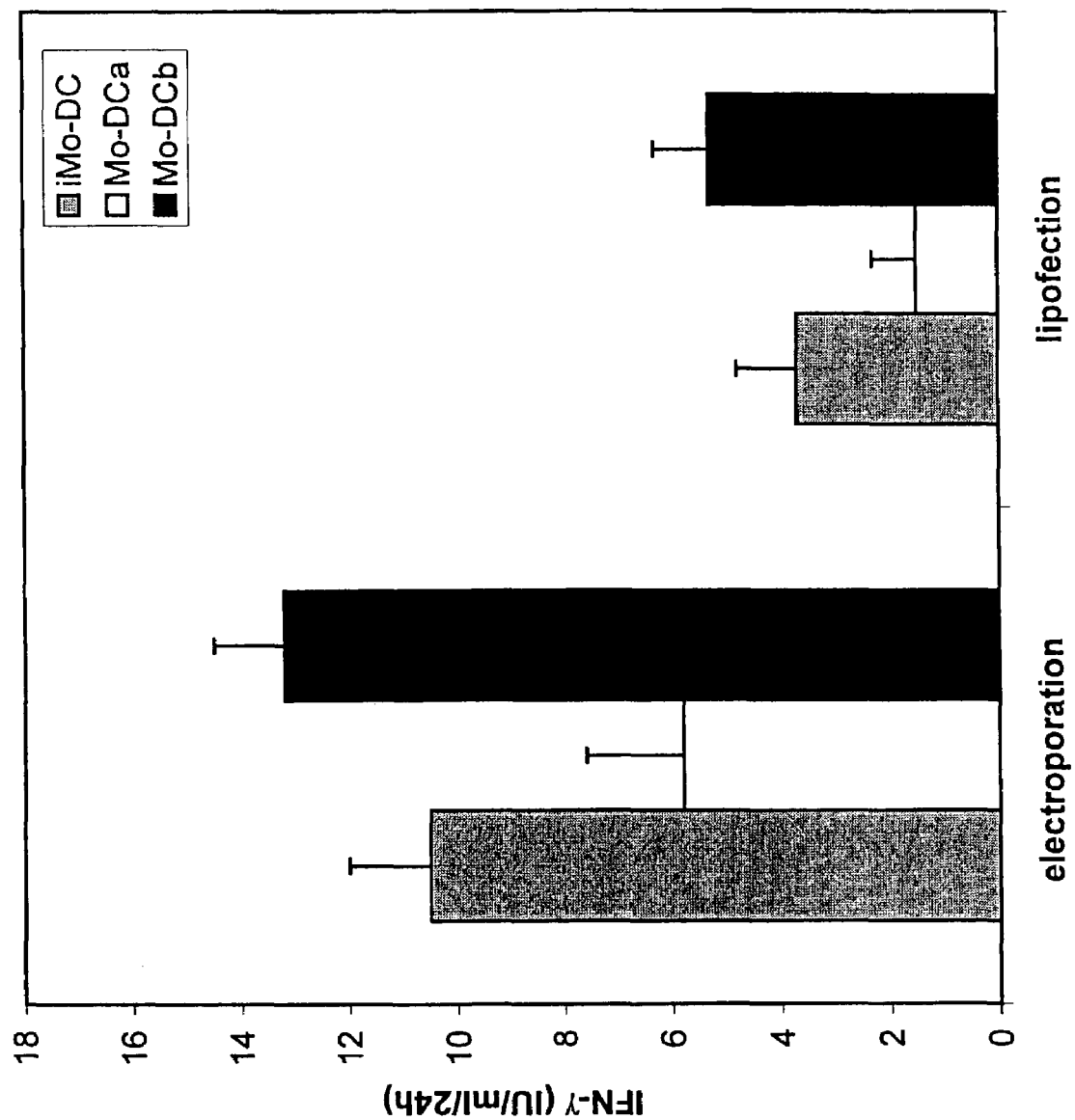

FIG. 5 shows the effect of DC maturation on tumor antigen presentation of mRNA-transfected Mo-DC. IFN-γ production by the CTL clone was measured after coculture with HLA-A2+ Mo-DC electroporated with Melan-A mRNA. iMo-DC, Mo-DC transfected at the immature stage and used as such; Mo-DCa, Mo-DC transfected at the mature stage after LPS+TNF-α stimulation; Mo-DCb, Mo-DC transfected at the immature stage, matured by LPS+TNF-α and then assayed for Melan-A-specific CTL clone stimulation. Results are shown as mean±SD (n=4). *P<0.05

Figure 6:
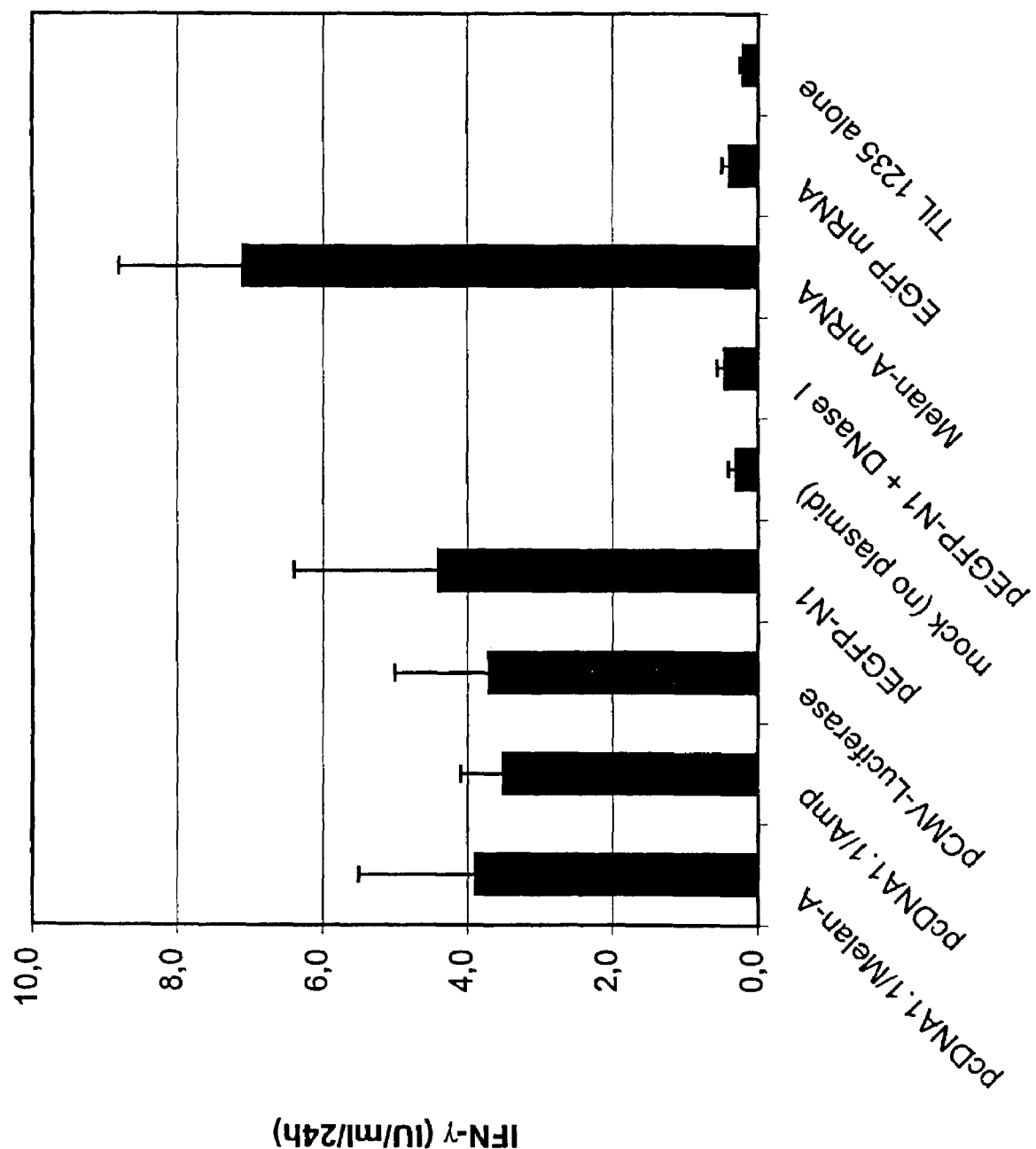

FIG. 6 shows the outcome of plasmid cDNA-based antigen loading of 34-LC. IFN-γ production by the CTL clone was measured after coculture with HLA-A2+ 34-LC electroporated with various plasmid DNA constructs encoding Melan-A (pcDNA1.1/Melan-A; n=12), EGFP (pEGFP-N1; n=12), luciferase (pCMV-Luc; n=3) or with a backbone vector (pcDNA1.1/Amp; n=6) lacking a eukaryotic cDNA sequence. Alternatively, 34-LC were electroporated with in vitro transcribed mRNA encoding EGFP or Melan-A (n=3). Results are shown as mean±SD. *P<0.05.

Figure 7:
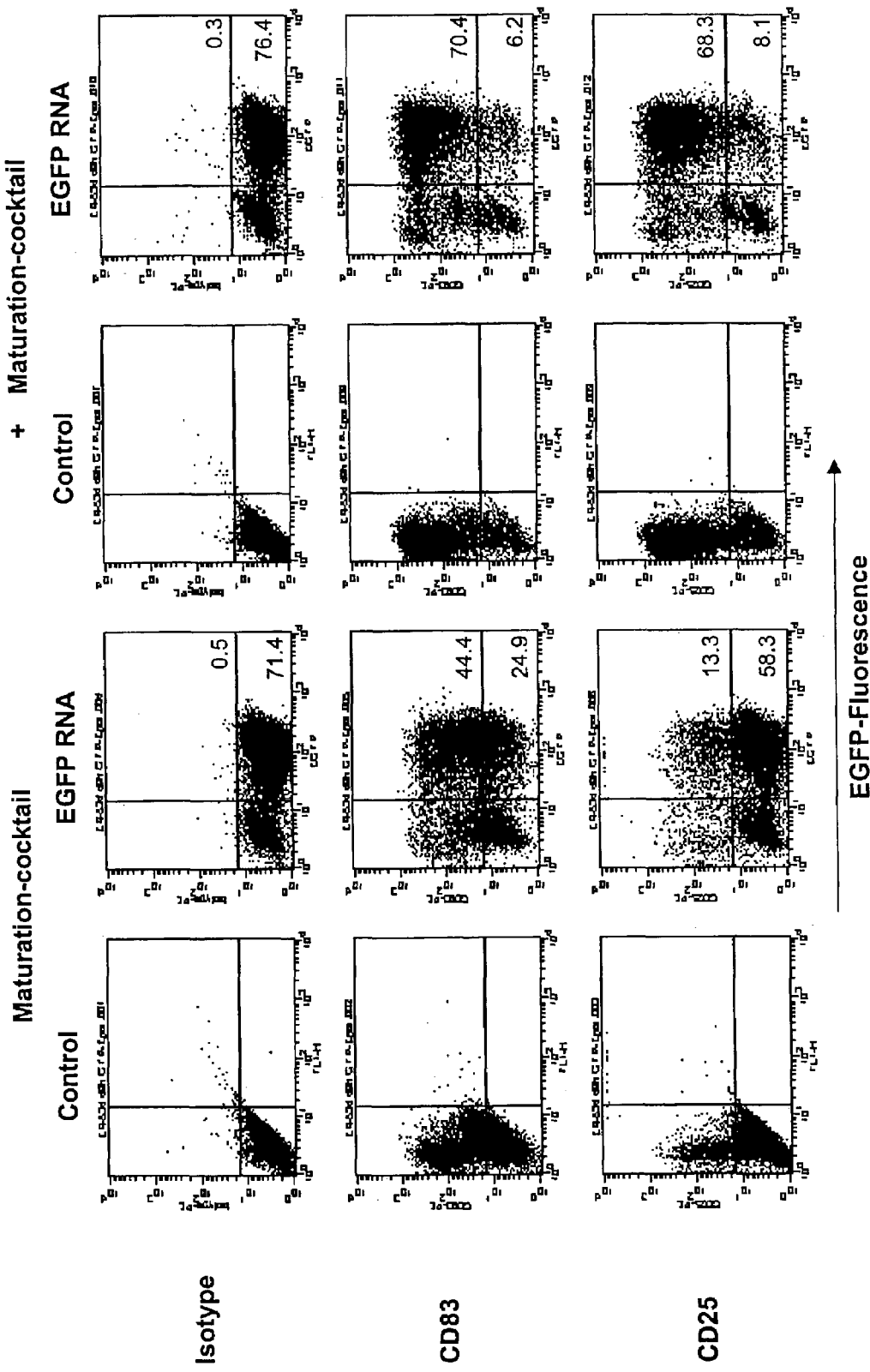

FIG. 7 shows the result of electroporation of immature monocyte-derived cells, in particular, the phenotype of dendritic cells 48 h after electroporation with GFP-RNA. The numbers in the lower right part of the quadrant indicate the EGFP-positive DC, the numbers in the upper right part show the EGFP+/CD83+ and EGFP+/CD25+ DC, respectively.

Figure 8:
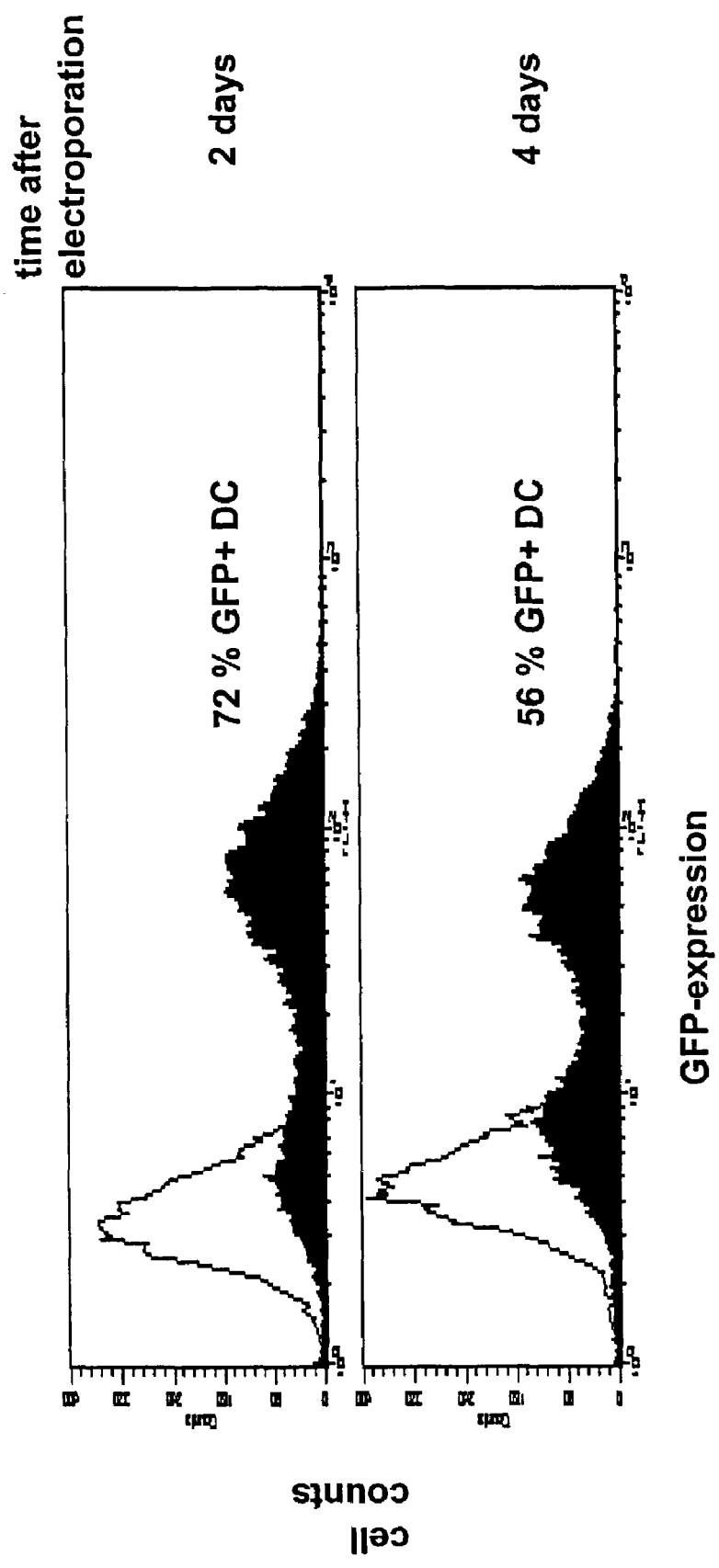

FIG. 8 shows the transfection efficiency of and kinetics of EGFP expression in dendritic cells following GFP-RNA-transfection using electroporation.

FIG. 9 shows the results of EGFP RNA-transfection of monocyte-derived dendritic cells by electroporation.

A: Contour plots showing the influence of voltage on cell size and granularity.

B: shows that the EGFP expression of CD83 and CD25 is influenced by the voltage.

FIG. 10: EGFP RNA-transfection of mature monocyte-derived dendritic cells by electroporation.

A and H show the transfection efficiency and kinetics of EGFP expression following GFP-RNA transfection of mature dendritic cells using electroporation.

B to G confirm that the phenotype of dendritic cells is maintained after electroporation with GFP-RNA.

Figure 11:
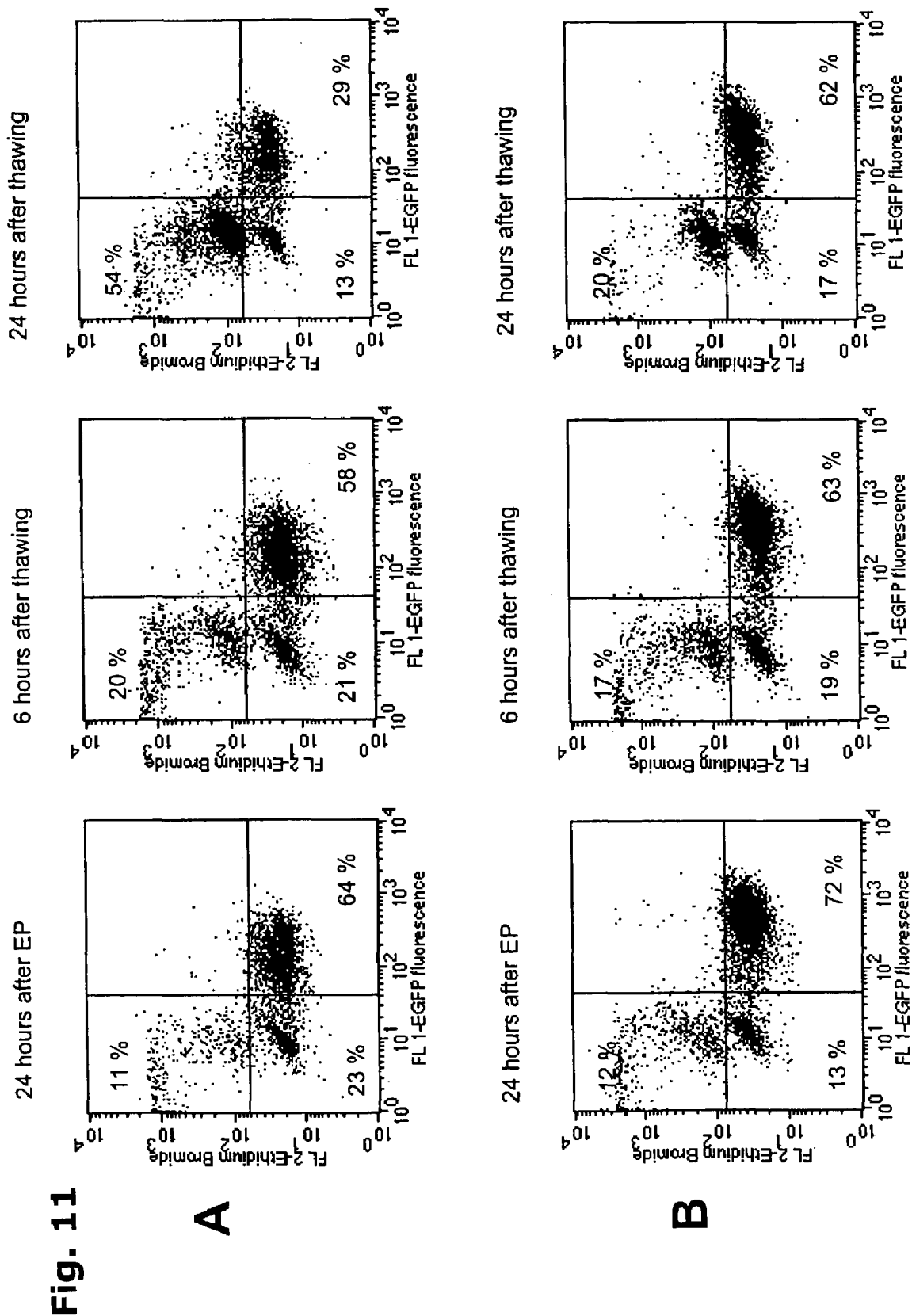

FIG. 11: FCM analysis of transgene expression in immature and mature DC after EGFP mRNA electroporation in non-frozen controls and after thawing of cryopreserved samples. The dot plots show EGFP fluorescence on the x-axis and ethidium bromide staining on the y-axis. Analysis was performed on cells exhibiting a large forward scatter and large side scatter profile, in order to allow exclusion of contaminating autologous lymphocytes. Percentage of dead cells (upper left corner), viable EGFP+ cells (lower right corner) and viable EGFP− cells (lower left corner) is indicated based on the number of dots in the quadrant analysis. (A) Dot plots show analysis of non-frozen iMo-DC 24 hours after mRNA electroporation (left), and of mRNA-electroporated iMo-DC 6 hours after thawing (middle) and 24 hours (right) after thawing. (B) Dot plots show analysis of non-frozen mMo-DC 24 hours after mRNA electroporation (left),and of mRNA-electroporated mMo-DC 6 hours after thawing (middle) and 24 hours (right) after thawing. EP=electroporation.

Figure 12A:
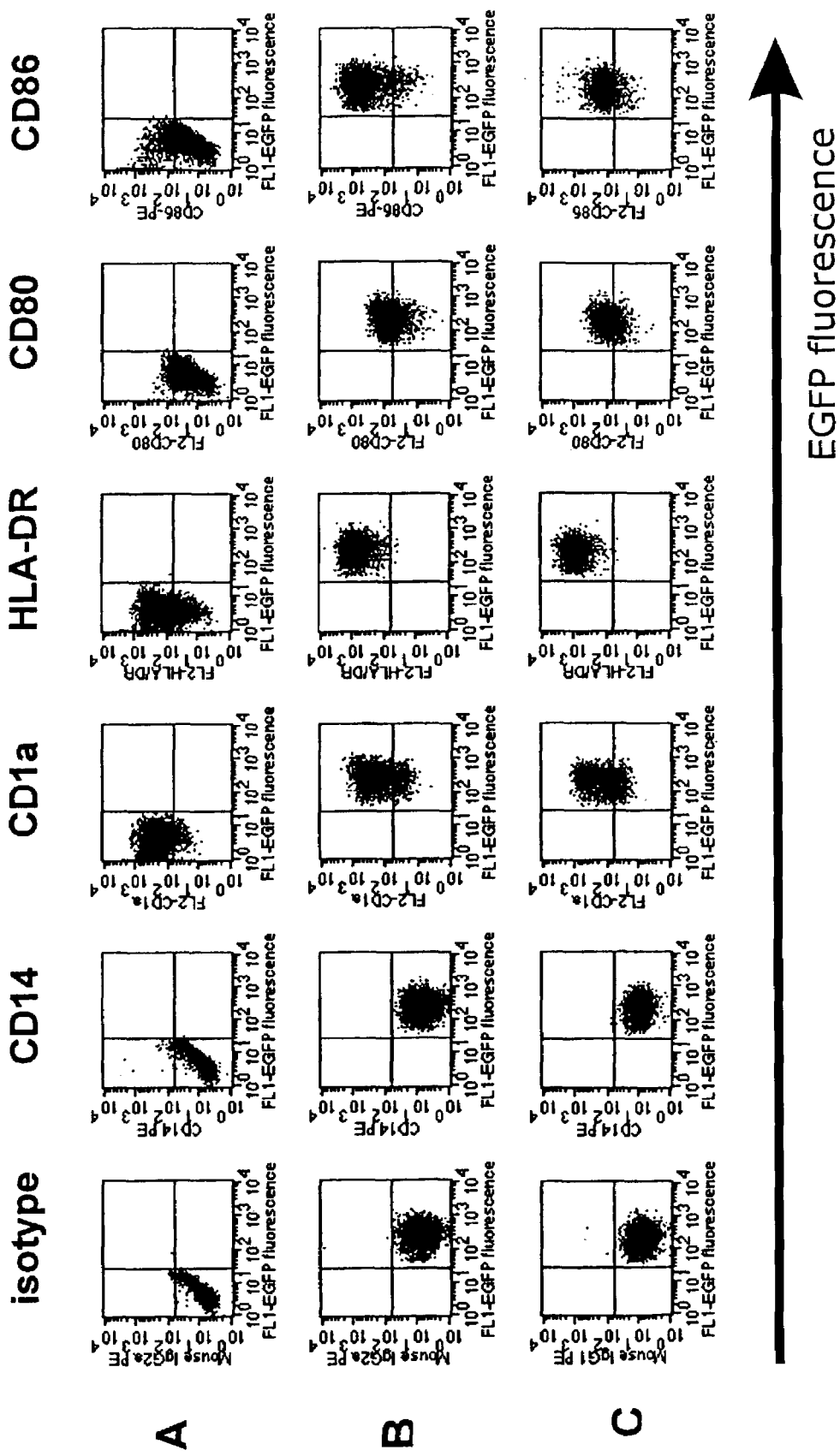
Figure 12B:
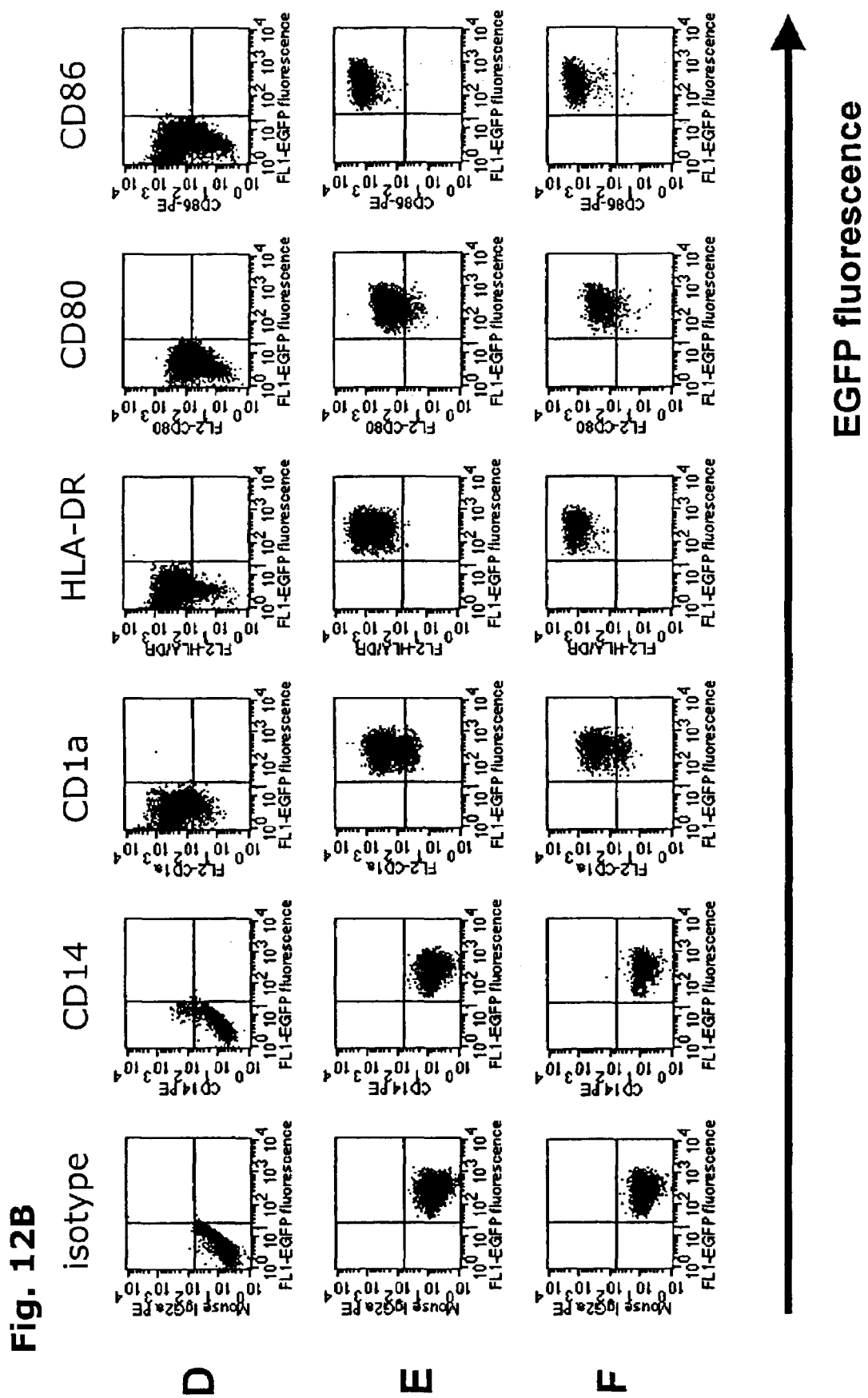

FIG. 12: Representative example of phenotypical analysis of non-frozen and frozen mRNA-electroporated immature and mature DC. Dot plots show FCM analysis of PE-labeled monoclonal antibodies directed against typical DC-markers including CD1a, HLA-DR, CD80 and CD86 (y-axis). As controls to set quadrants, isotype-matched antibodies and a PE-labeled monoclonal CD14 antibody was used. Analysis of DC markers was done on viable EGFP− cells in control samples and on viable EGFP+ cells in mRNA-electroporated DC as shown by the EGFP fluorescence on the x-axis. (A) iMo-DC on day 8 of culture, (B) EGFP+ iMo-DC after mRNA electroporation on day 6, followed by 48 hours of culture. (C) EGFP+ iMo-DC after mRNA electroporation on day 6, culture for 18 hours, cryopreservation, thawing and culture for 24 hours. (D) iMo-DC that have been stimulated for 48 hours with a maturation cocktail after day 6. (E) EGFP+ iMo-DC after mRNA electroporation on day 6 and stimulation for 48 hours with the maturation cocktail, (F) EGFP+ iMo-DC after mRNA electroporation on day 6 and culture for 24 hours with a maturation cocktail, cryopreservation, thawing and culture for 24 hours in presence of the maturation cocktail. In general, phenotyping was performed after 2 days of culture, with or without a frozen interval (that was not counted), following day 6 of the Mo-DC culture.

As shown by the dot plot analysis of FIG. 12, iMo-DC undergo maturation at 48 hours after mRNA electroporation as demonstrated by an upregulation of HLA-DR, CD80 and CD86 (FIGS. 12, A & B). Thawed DC have the same upregulation of HLA-DR and CD80, but have lower levels of CD86 (FIG. 12, C). This is probably caused by the fact that the frozen immature DC culture is dying 24 hours after thawing. Immature Mo-DC responded well to the maturation cocktail as seen by the upregulation of HLA-DR, CD80 and CD86 in mMo-DC as compared with the expression levels in iMo-DC (FIGS. 12A, & D). However, the combination of mRNA electroporation and a maturation stimulus seems to be very potent in maturing DC, as this combination results in high level of HLA-DR, CD80 and CD86 expression (FIG. 12, E). Frozen mature DC that were electroporated show high level maturation marker expression after thawing (FIG. 12, F).

Figure 13:
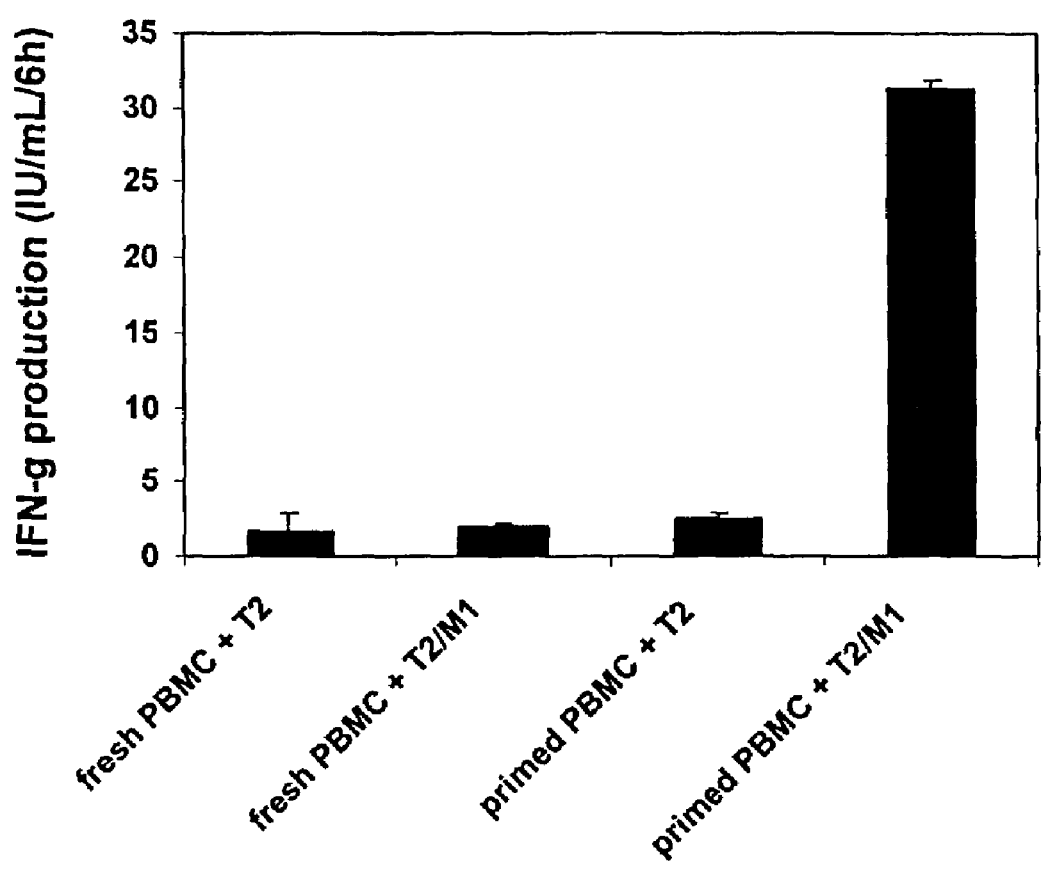

FIG. 13: Stimulatory capacity of cryopreserved mRNA-electroporated mature DC. Cryopreserved matrix protein M1 mRNA-electroporated mature DC were used as stimulators for PBMC during a 6 day coculture. Primed PBMC were then stimulated with T2 cells, pulsed with an MHC class I-restricted M1 immunodominant epitope, during a 6 hour coculture. Antigen specific T cells in the primed PBMC culture were detected as shown by positive IFN-γ production. As controls, unpulsed T2 cells were used as stimulators and fresh PBMC as responders. Results are shown as mean±standard error.

Upon restimulation with peptide-pulsed T2 cells, the activated T cells in the primed PBMC culture produced IFN-γ against the immunodominant matrix protein peptide. The specificity of this activation is shown by only background IFN-γ production of the primed PBMC culture against unpulsed T2 cells. To show that these cultured PBMC were stimulated during the 6 day culture, the same experiment was done with fresh PBMC. After coculture with either T2 cells or T2 cells pulsed with the peptide, no IFN-γ production was detected above background level (FIG. 13).

Figure 14:
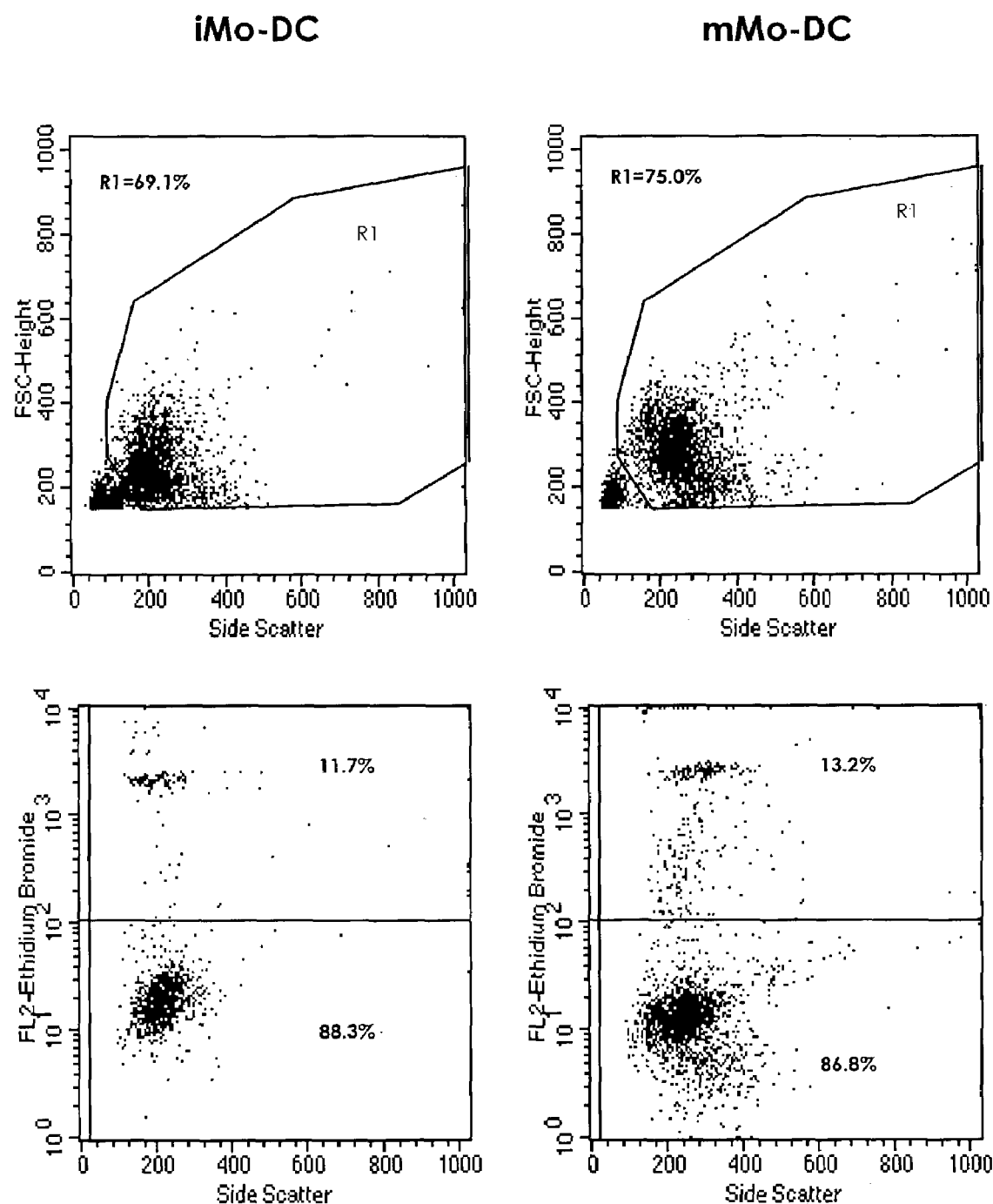

FIG. 14: Representative flow cytometric analysis of scatter profile and viability of short-term serum-free-cultured immature DC and poly-I:C-maturated DC of Example 6.

Left side, immature monocyte-derived DC (iMo-DC) cultured for 2 days in AIM-V medium+GM-CSF. Right side, poly-I:C-maturated monocyte-derived DC (mMo-DC). Upper dot plots show forward and side scatter profiles of all cells. The R1 gate shows the percentage of DC in the cultures. Lower dot plots show mortality by ethidium bromide staining within the cultured DC. (upper numbers, ethidium bromide-positive dead DC; lower numbers, ethidium bromide-negative living DC). The lower dot plots were gated on R1 (upper panel). The data shown are from PBMC donor A. The results are representative for PBMC from donors A, B, F for immature DC and A, B, C, D, E, F for mature DC.

Figure 15:
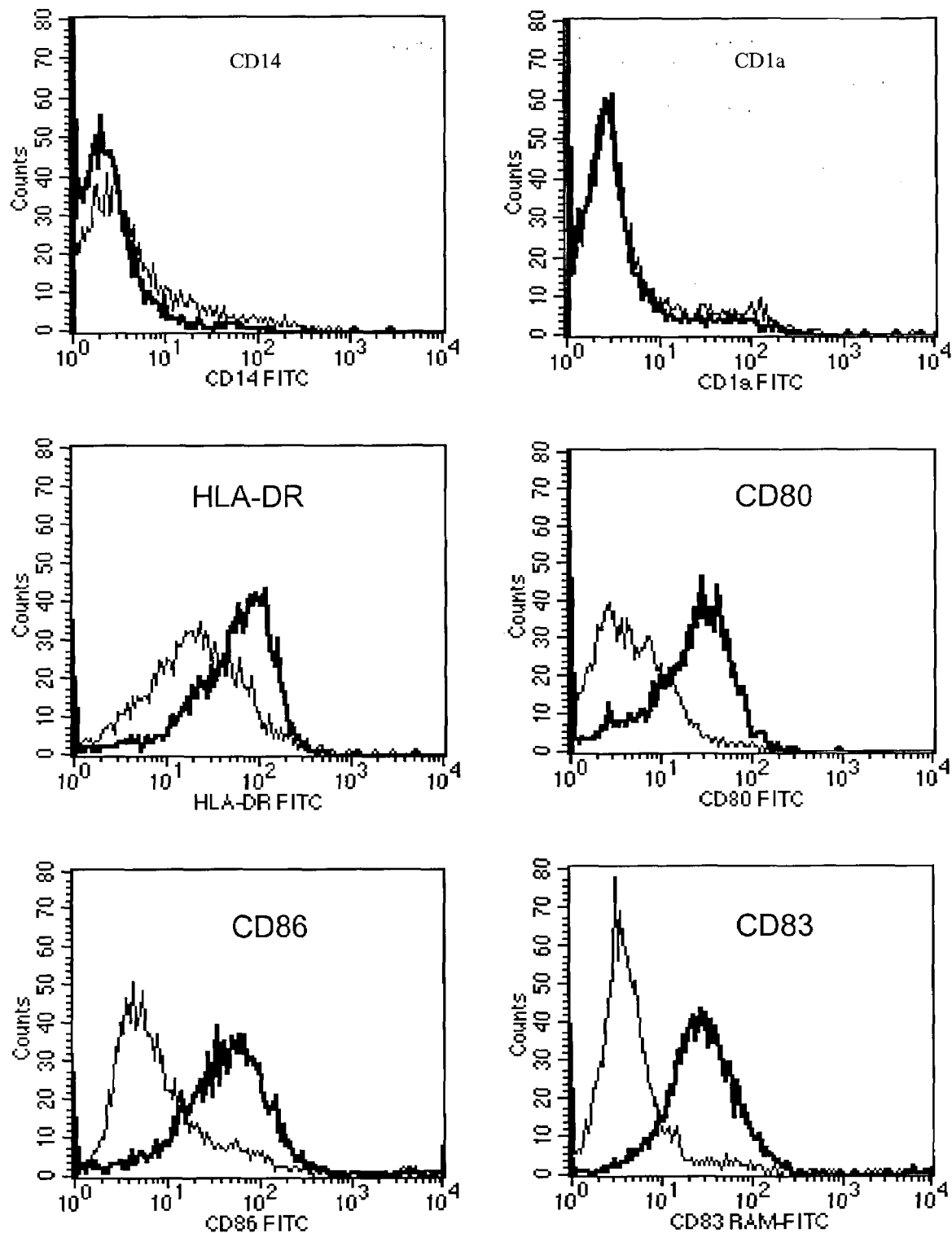

FIG. 15: Representative phenotypical analysis of short-term serum-free-cultured immature DC and serum-free-cultured poly-I:C-maturated DC of Example 6.

Flow cytometric analysis of FITC-labeled monoclonal antibodies directed against DC and monocyte markers: CD14, HLA-DR, CD86 (left side) and CD1a, CD80, CD83 (right side). After 2 days of culture in AIM-V medium supplemented with GM-CSF, with or without addition of poly-I:C after 1 day of culture, DC were analyzed by outgating remaining lymphocytes. Comparative data are shown in histograms for immature (thin line) and mature (thick line) DC. The data shown are from PBMC donor A. The results are representative for PBMC from donors A, B, F for immature DC and A, B, C, D, E, F for mature DC.

Figure 16:
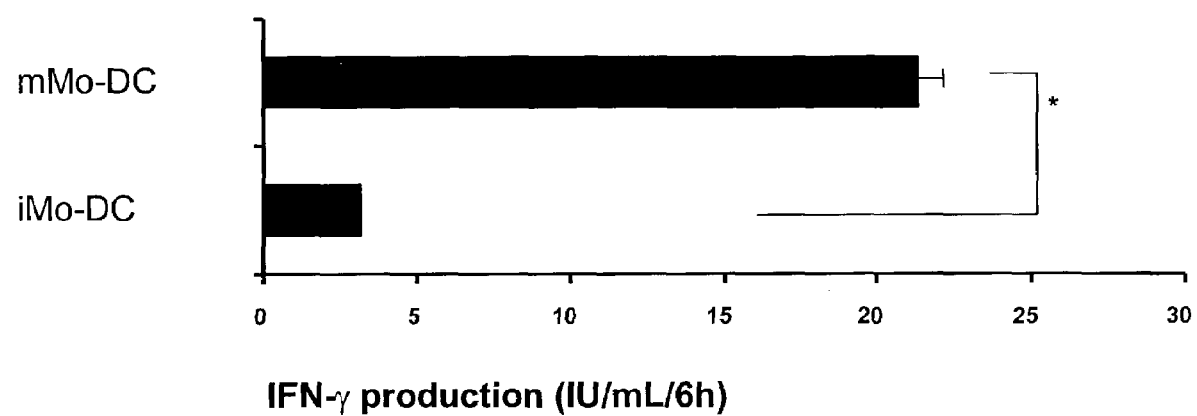

FIG. 16: Allogeneic stimulatory capacity of short-term serum-free-cultured immature DC versus serum-free-cultured poly-I:C-maturated DC of Example 6. Immature and mature short-term cultured DC (respectively iMo-DC and mMo-DC) were used as stimulators for allogeneic PBMC during a 7-day coculture. Afterwards, primed PBMC were restimulated with PBMC from the DC donor during a 6-hour coculture. Activated T-cells in the primed PBMC culture were detected as shown by IFN-γ production against the target PBMC. Results are shown as mean±standard deviation of two individual experiments for cultures initiated with immature DC (iMo-DC) and mature DC (mMo-DC). The significant difference is indicated with an asterisk. Results were obtained with PBMC from donors B and C.

Figure 17:
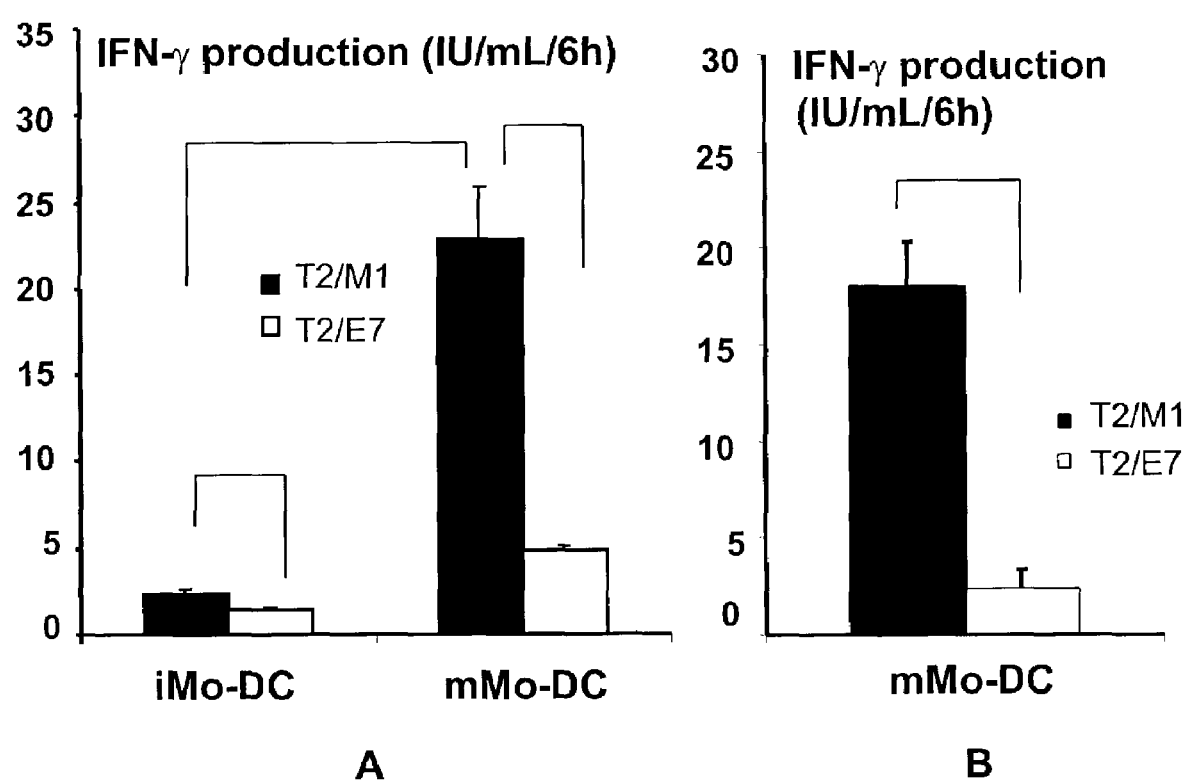

FIG. 17: Stimulatory capacity of short-term serum-free-cultured immature DC versus serum-free-cultured poly-I:C-maturated DC (Example 6).

Influenza matrix protein M1 peptide-pulsed immature and mature DC (respectively iMo-DC and mMo-DC) were used as stimulators for autologous PBMC during a 7-day coculture. Afterwards, primed PBMC were restimulated with T2 cells, pulsed with a MHC class I-restricted influenza matrix protein M1 peptide (T2/M1), during a 6-hour coculture. Antigen-specific T cells in the primed PBMC culture were detected as shown by increased IFN-γ production. As a control, irrelevant HPV E7 peptide-pulsed T2 cells (T2/E7) were used as stimulators. Significant differences are indicated with an asterisk. Results were obtained with PBMC from donor B (FIG. 17A, 3 experiments) and donor F (FIG. 17B, 2 experiments).

Figure 18:
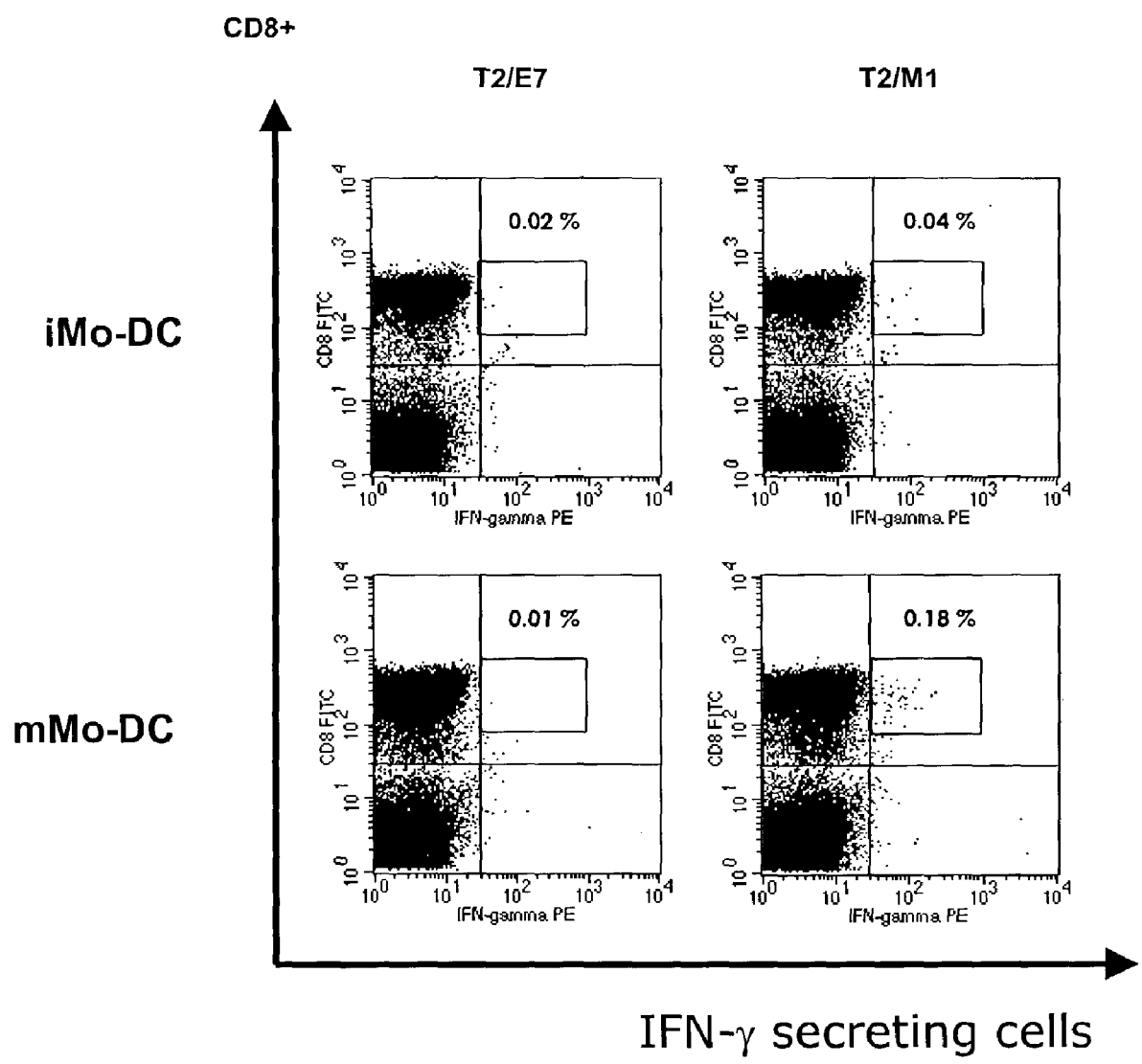

FIG. 18: Stimulatory capacity of serum-free-cultured immature DC versus serum-free cultured poly-I:C-maturated DC. Direct staining of IFN-γ-secreting CD8+ T cells after restimulation with an influenza target (Example 6).

Influenza matrix protein M1 peptide-pulsed immature and mature DC (respectively iMo-DC and mMo-DC) were used as stimulators for PBMC during a 7-day coculture. Primed PBMC were then restimulated for three hours with T2 cells pulsed with a MHC class I-restricted influenza M1 peptide or with an HPV E7 control peptide. Dot plots show IFN-γ-secreting cells within the CD8+ and CD8− lymphocyte population. The numbers of IFN-γ-secreting cells indicated on the dot plots are percentages of total lymphocytes. Results were obtained with PBMC from donor B.

Figure 19:
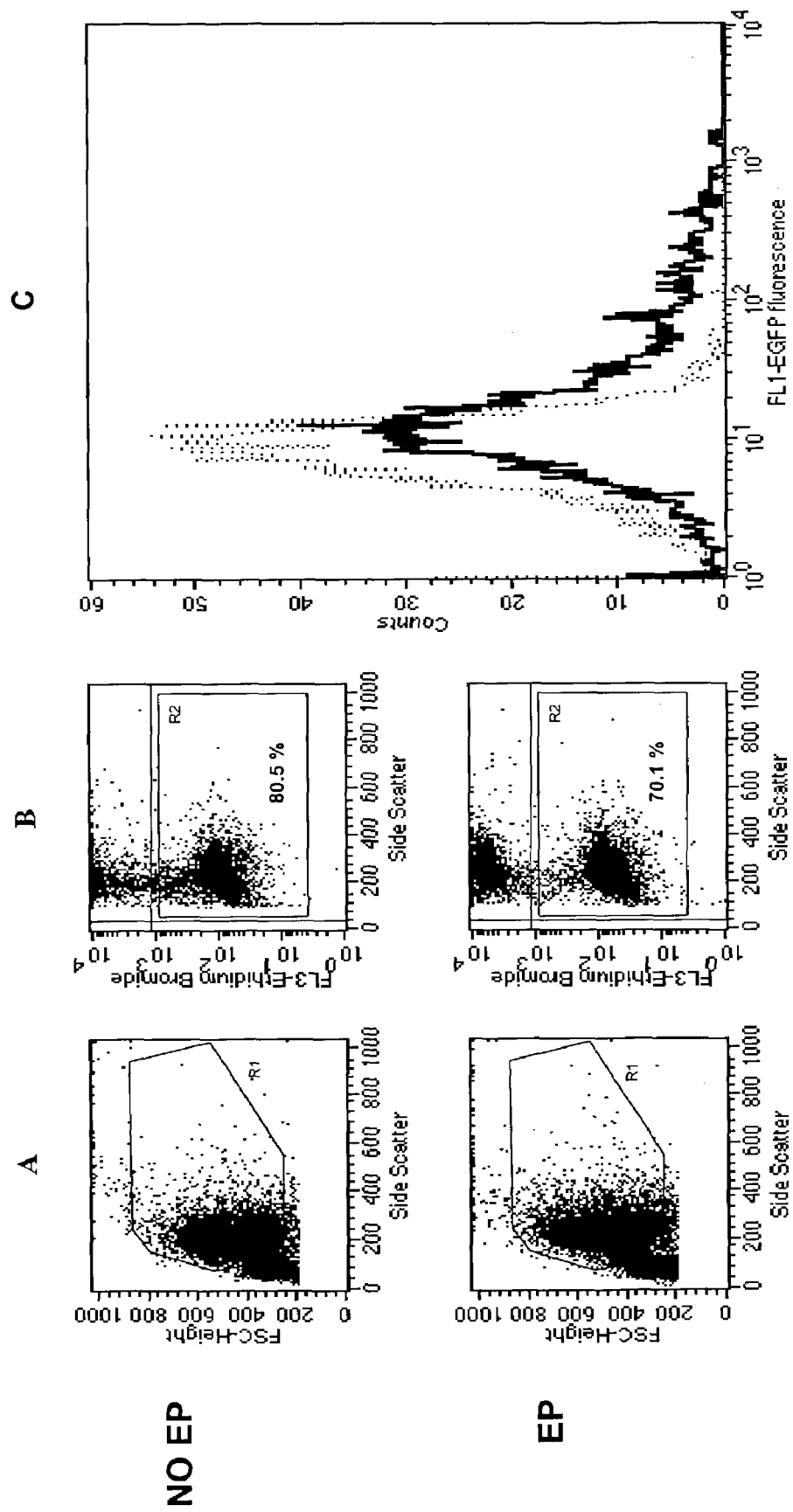

FIG. 19: Representative flow cytometric analysis of scatter profile, viability and EGFP expression of EGFP mRNA-electroporated monocytes short-term cultured to mature DC (Example 6).

Monocytes, electroporated (EP, lower dot plots), or not (EP, upper dot plots), with EGFP mRNA were cultured for 2 days in AIM-V medium+GM-CSF. Maturation was induced by poly-I:C after 24 hours of culture. (A) Scatter profile of the cultured mature DC. (B) Ethidium bromide staining of the cultured mature DC. The dot plots were gated on R1 (scatter profile). The indicated numbers show the percentage of ethidium bromide-negative living DC. (C) FL-1 EGFP fluorescence histogram overlay of non-electroporated mature DC (thin dotted line) and EGFP mRNA-electroporated mature DC (thick line). The data shown are from PBMC donor D. The results are representative for PBMC from donors C, D, E.

Figure 20:
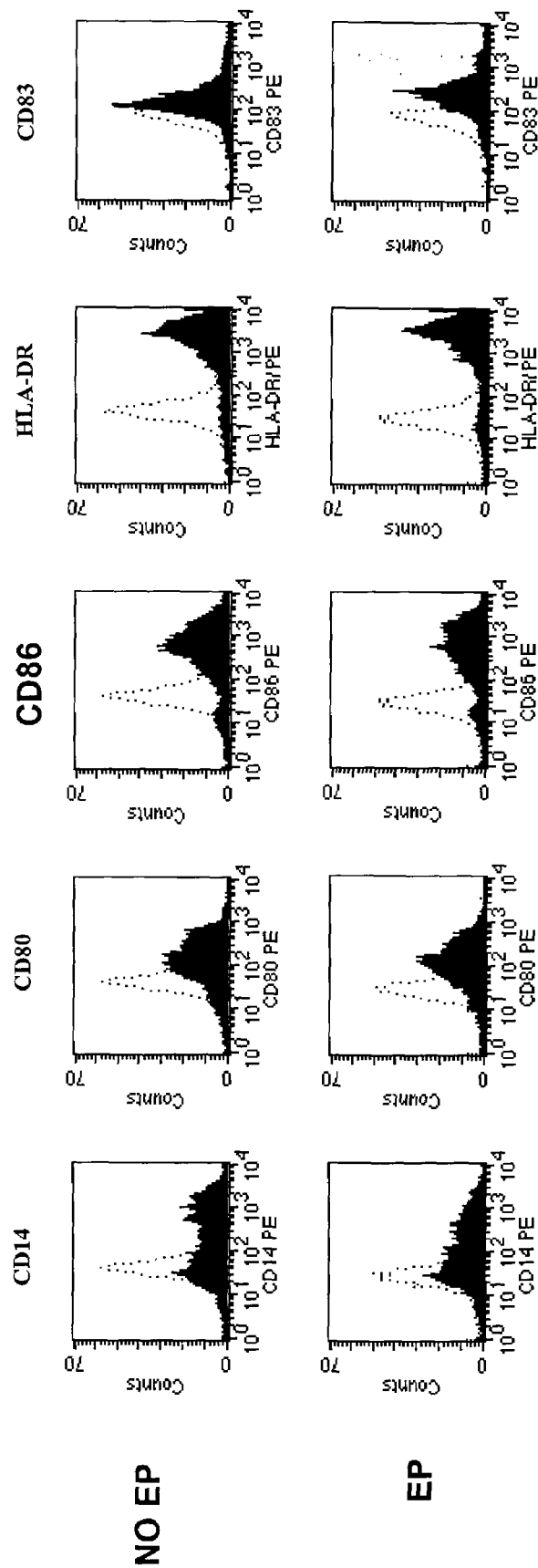

FIG. 20: Representative phenotypical analysis of monocytes electroporated with mRNA and short-term serum-free cultured to mature DC (Example 6).

Flow cytometric analysis of PE-labeled monoclonal antibodies directed against DC and monocyte markers: CD14, CD80, CD86, HLA-DR and CD83. Monocytes, electroporated (EP, lower dot plots), or not (EP, upper dot plots), with EGFP mRNA were cultured for 2 days in AIM-V medium+GM-CSF. Maturation was induced by poly-I:C after 24 hours of culture. Histograms show the level of marker expression (black overlay) against isotype control staining (dotted line). The data shown are from PBMC donor D. The results are representative for PBMC from donors C, D, E.

Figure 21:
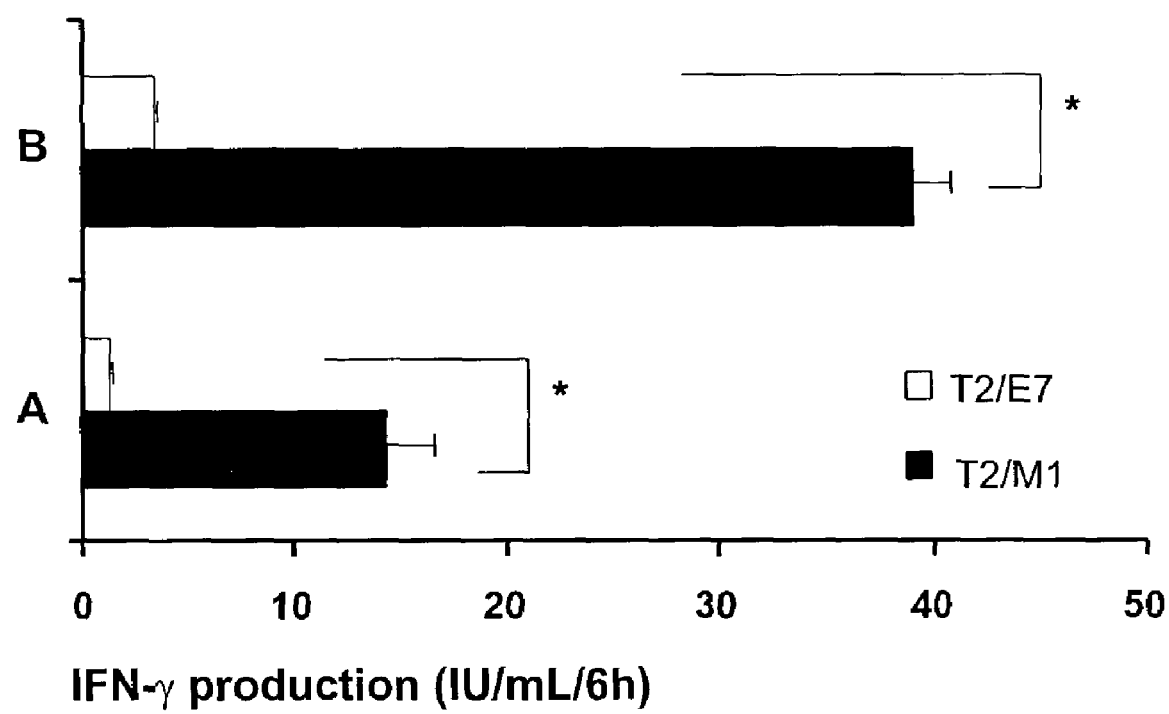
Figure 22A:
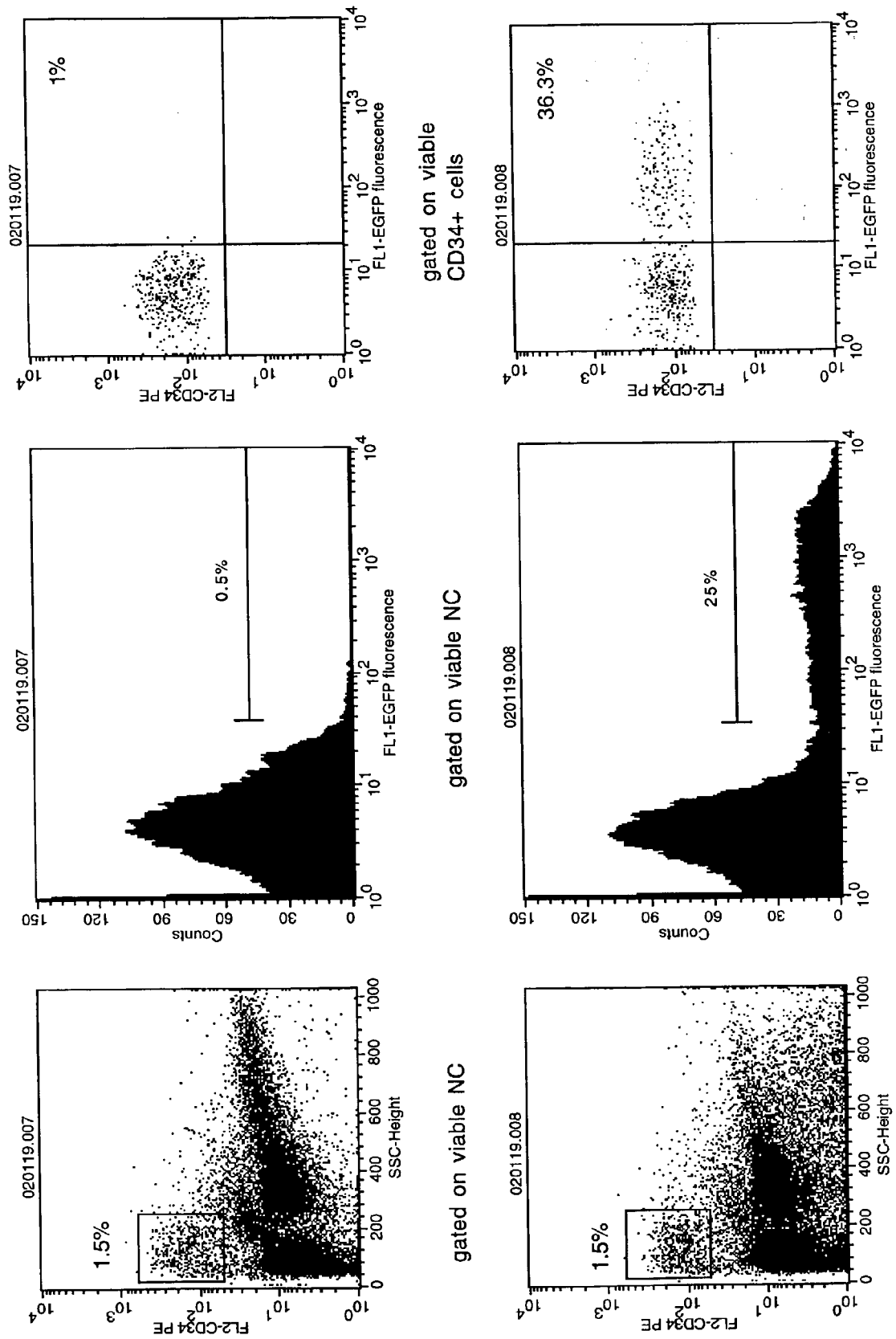
Figure 22B:
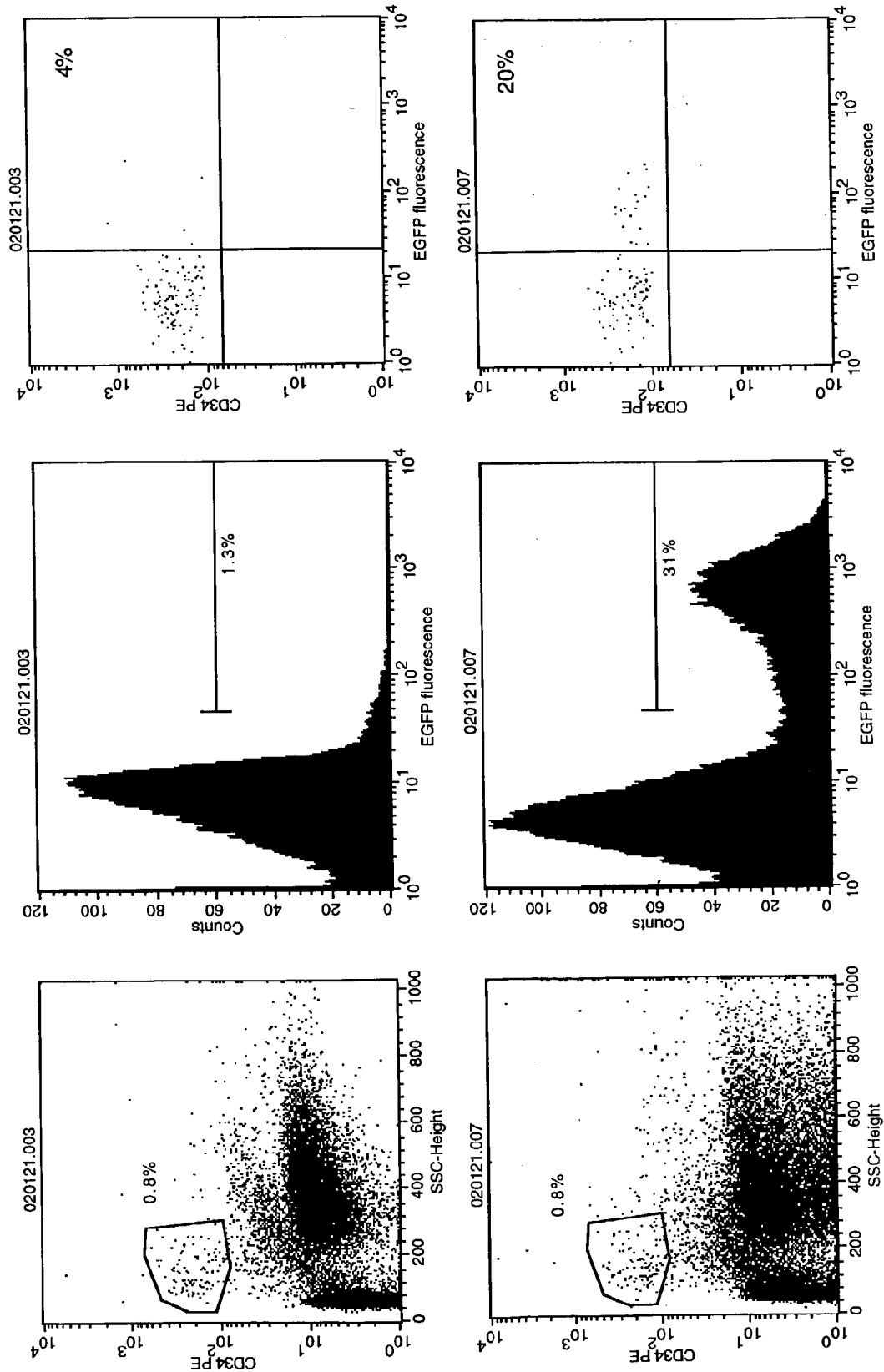
Figure 22C:
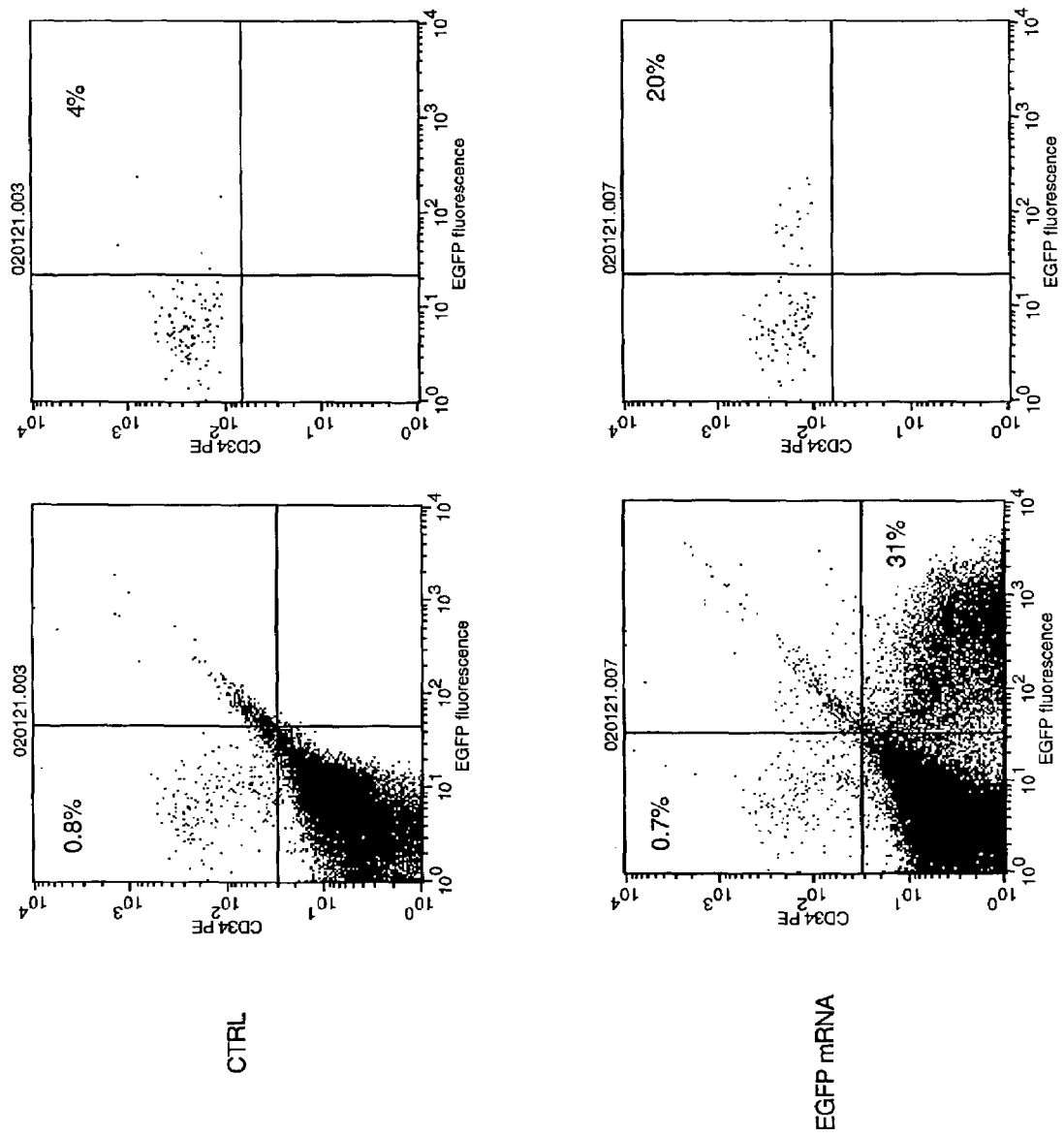
Figure 22D:
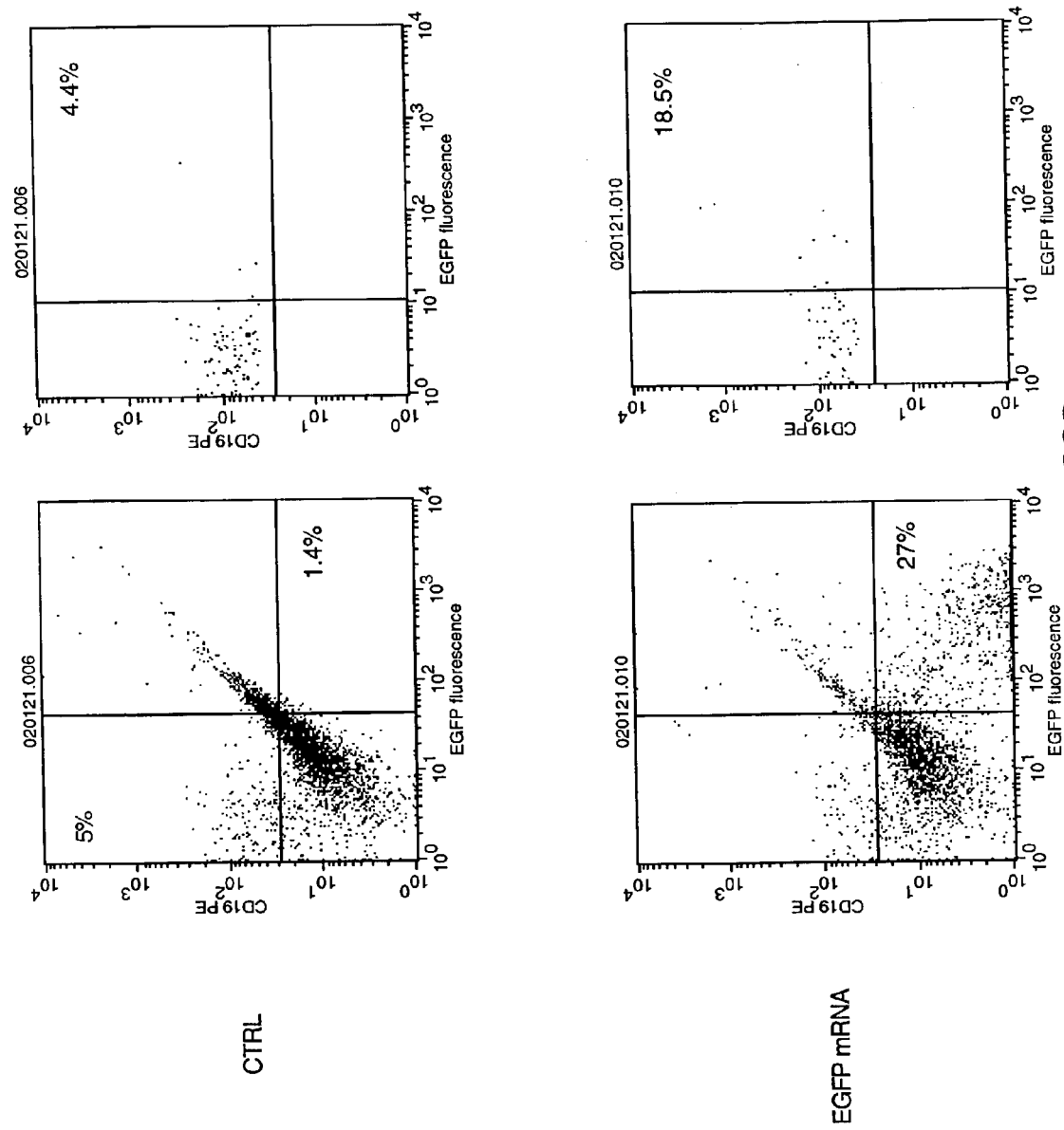
Figure 22E:
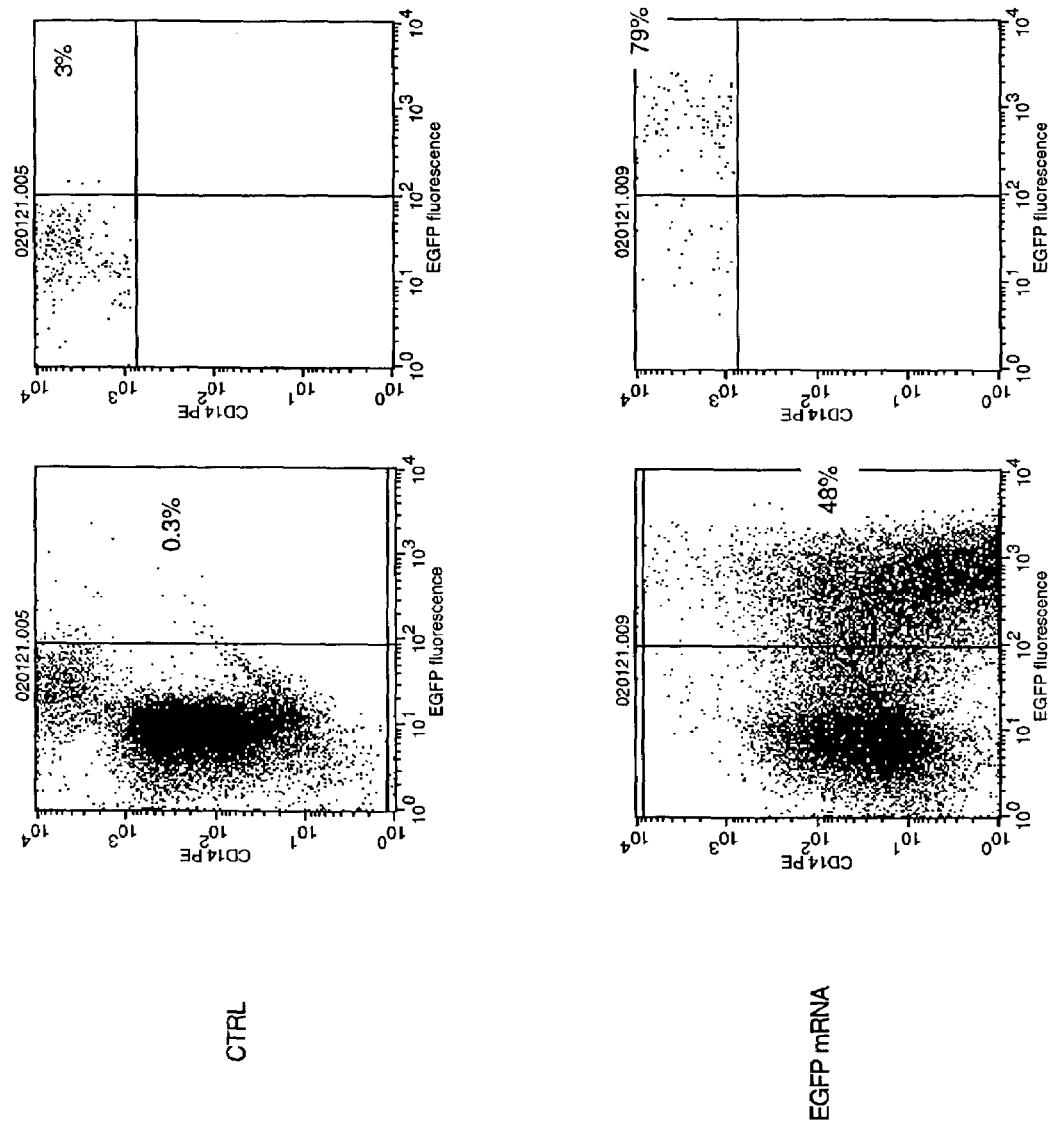
Figure 22F:
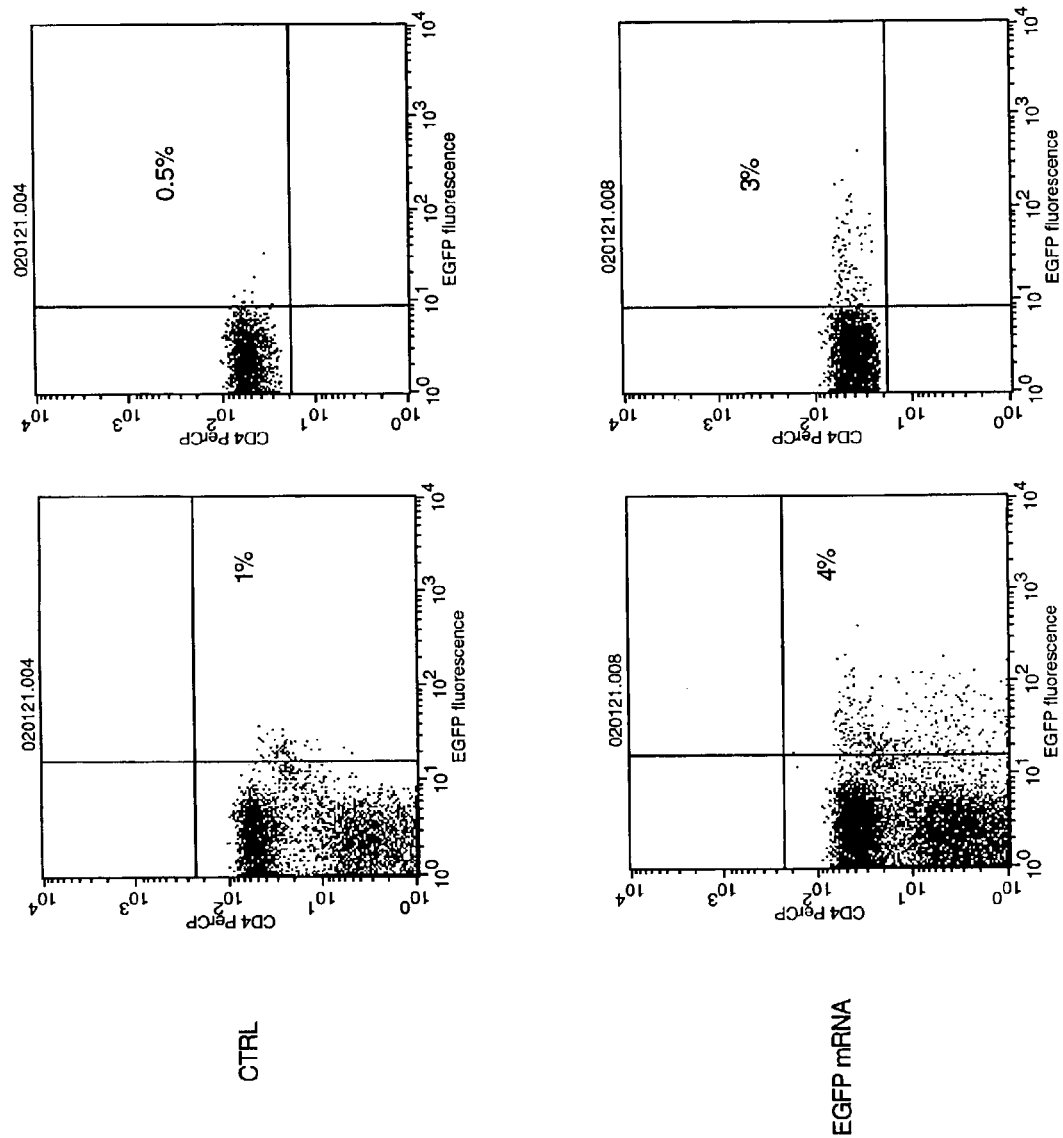

FIG. 21: Stimulatory capacity of mRNA-electroporated monocytes short-term serum-free cultured to mature DC (Example 6).

Monocytes, electroporated with influenza matrix protein mRNA, were cultured for 2 days in AIM-V medium+GM-CSF. Maturation was induced by poly-I:C after 24 hours of culture. These mature antigen-loaded DC were used as stimulators for autologous PBMC during a 7-day coculture. Afterwards, primed PBMC were restimulated during a 6-hour coculture with T2 cells, pulsed with a MHC class I-restricted influenza matrix protein M1 peptide (T2/M1). Antigen-specific T-cells in the primed PBMC culture were detected as shown by increased IFN-γ production. As a control, irrelevant HPV E7 peptide-pulsed T2 cells (T2/E7) were used as stimulators. Results are shown as mean±standard deviation of three individual experiments for PBMC from donor B (indicated as A) and PBMC from donor C (indicated as B). Significant differences are indicated with an asterisk.

FIG. 22: The results of the EGFP analysis of the transfected cells of Example 7 at 24 and 96 h is shown in FIGS. 22A and B, respectively. The phenotypic analysis of the transfected cells of Example 7 after 96 h (CD34/gated on CD45+ cells; CD 19/gated on DR+ cells; CD 14/gated on CD33+ cells; CD 4/gated on CD7+ cells) is shown in FIGS. 22C to F, respectively.

Figure 23A:
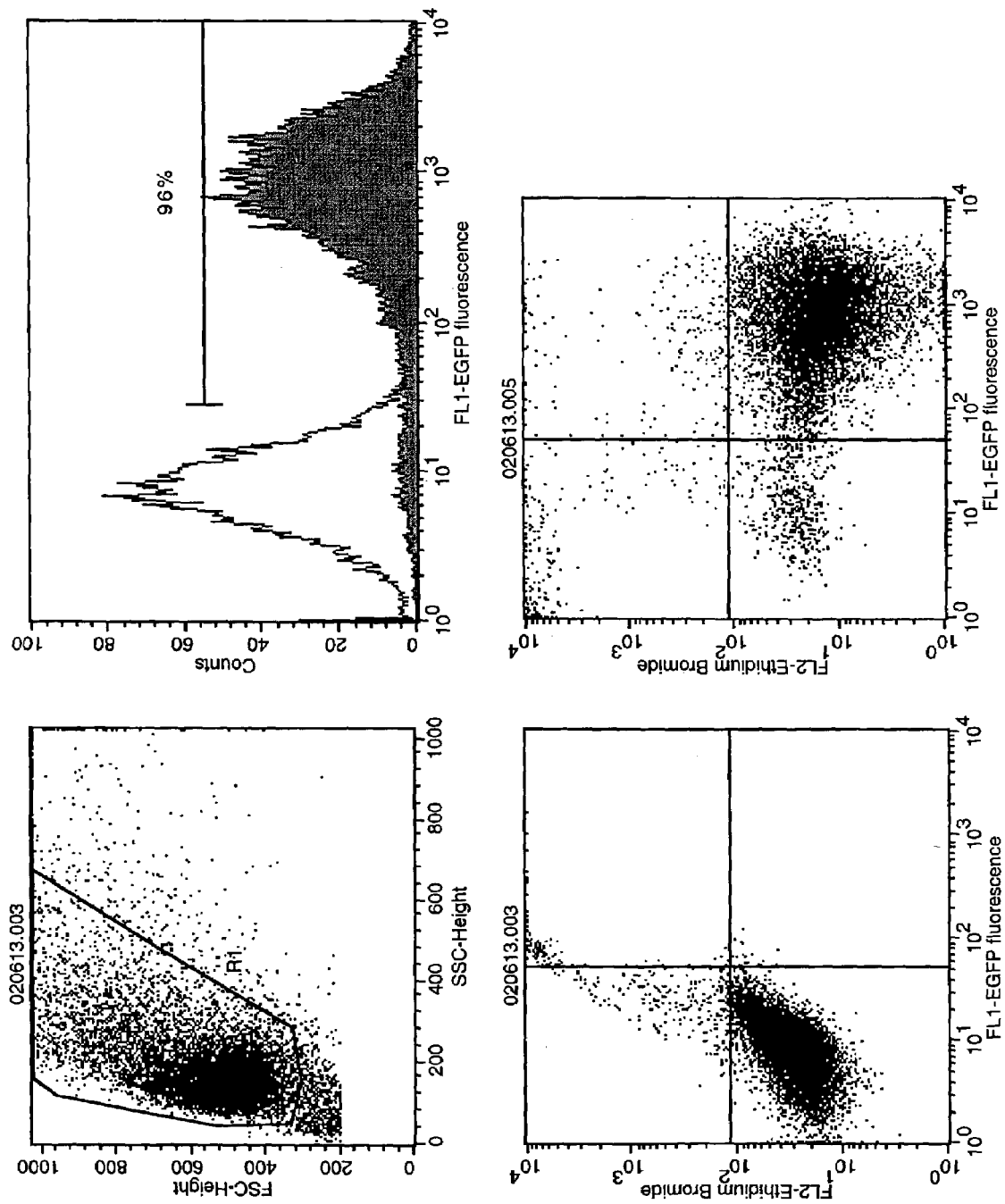
Figure 23B:
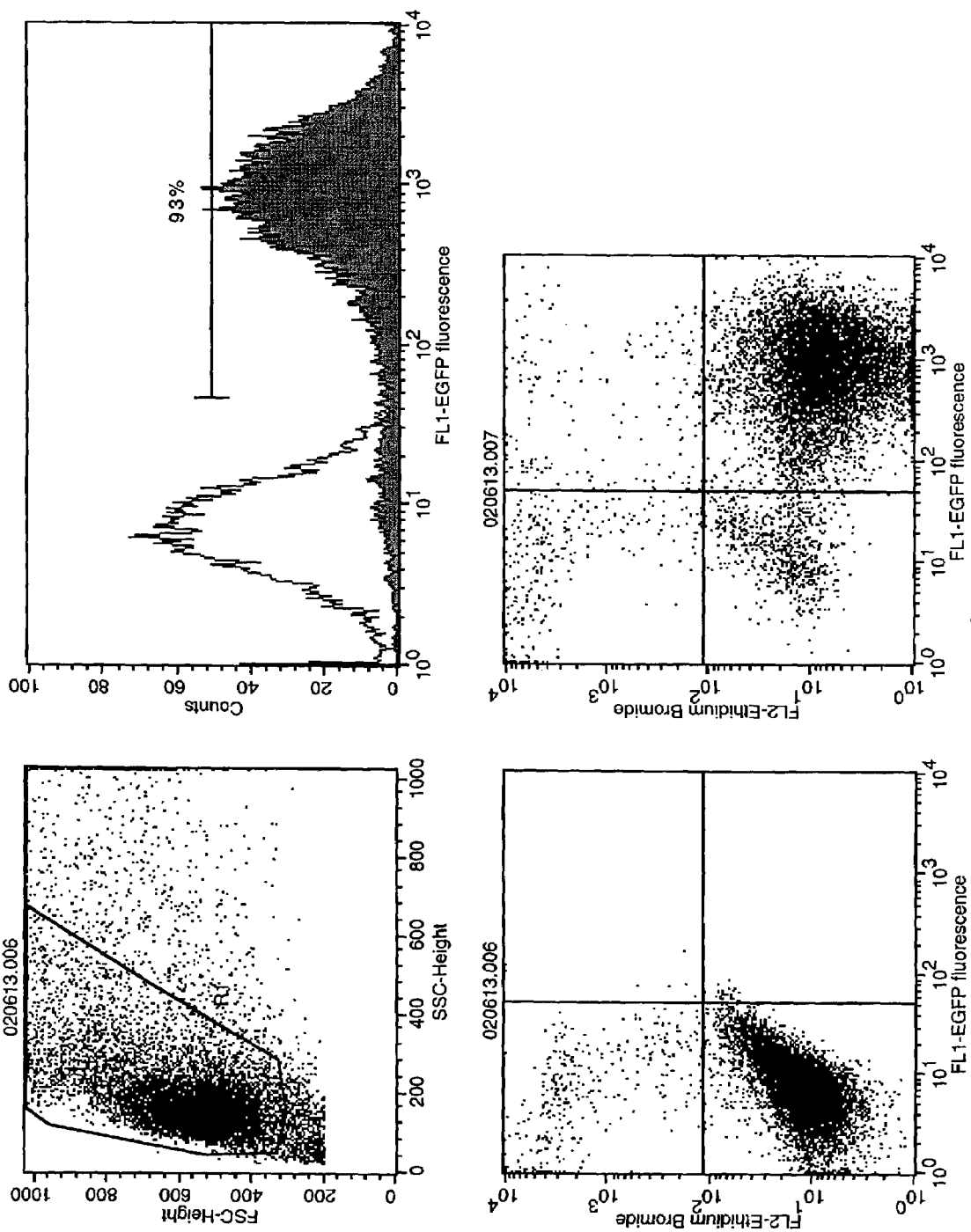
Figure 24A:
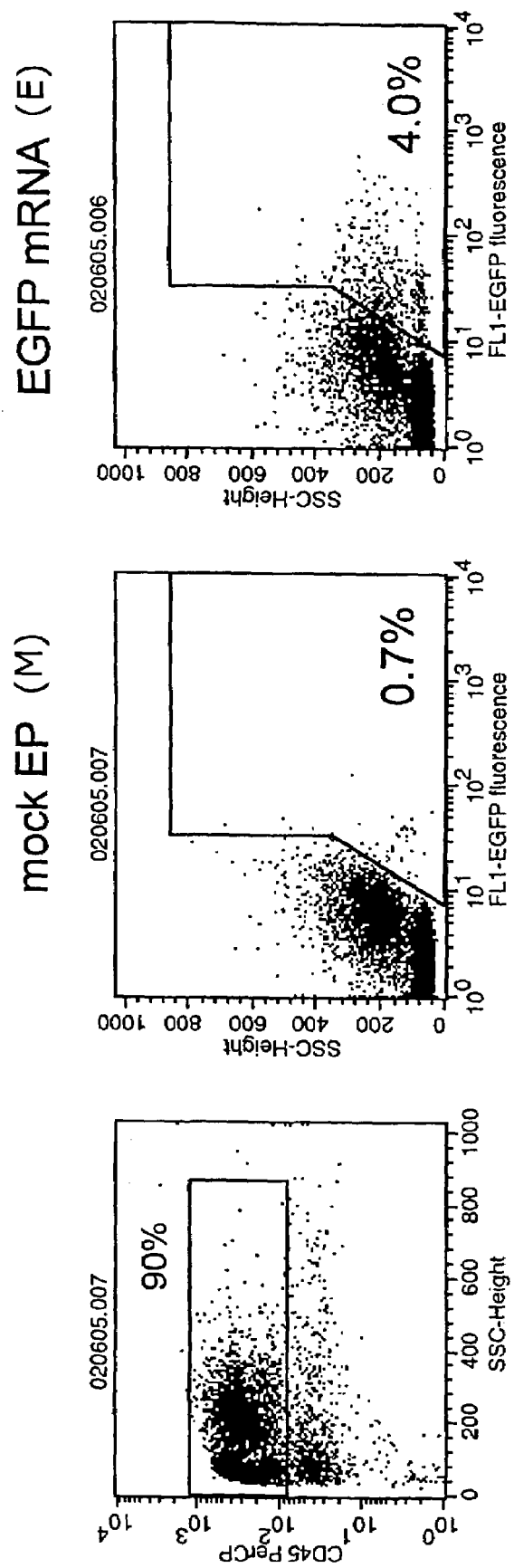
Figure 24B:
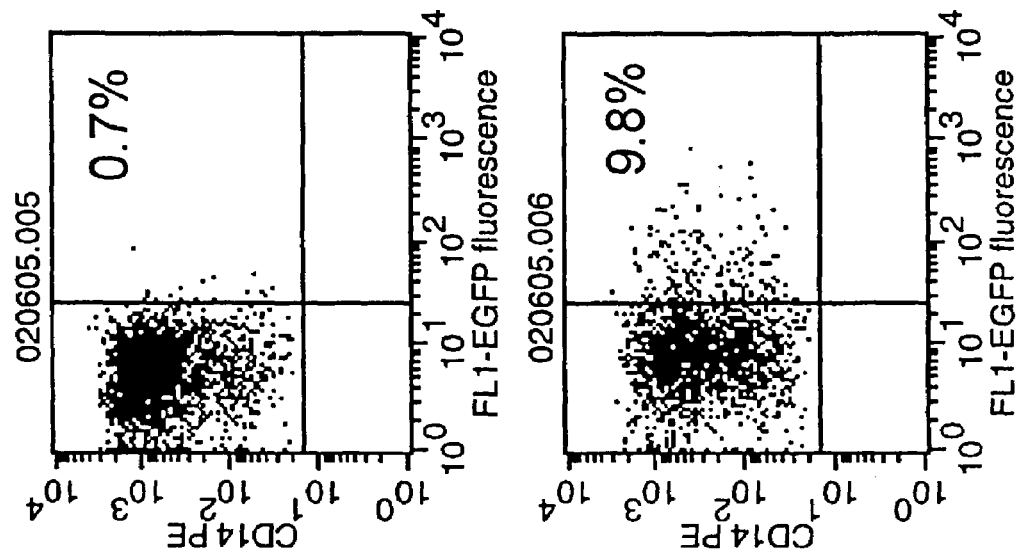
Figure 24B:
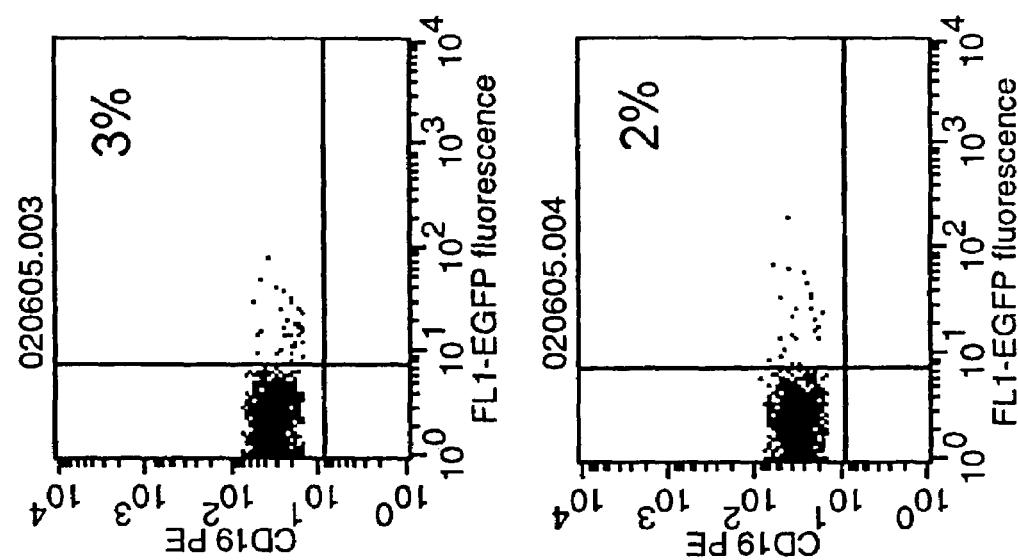
Figure 24C:
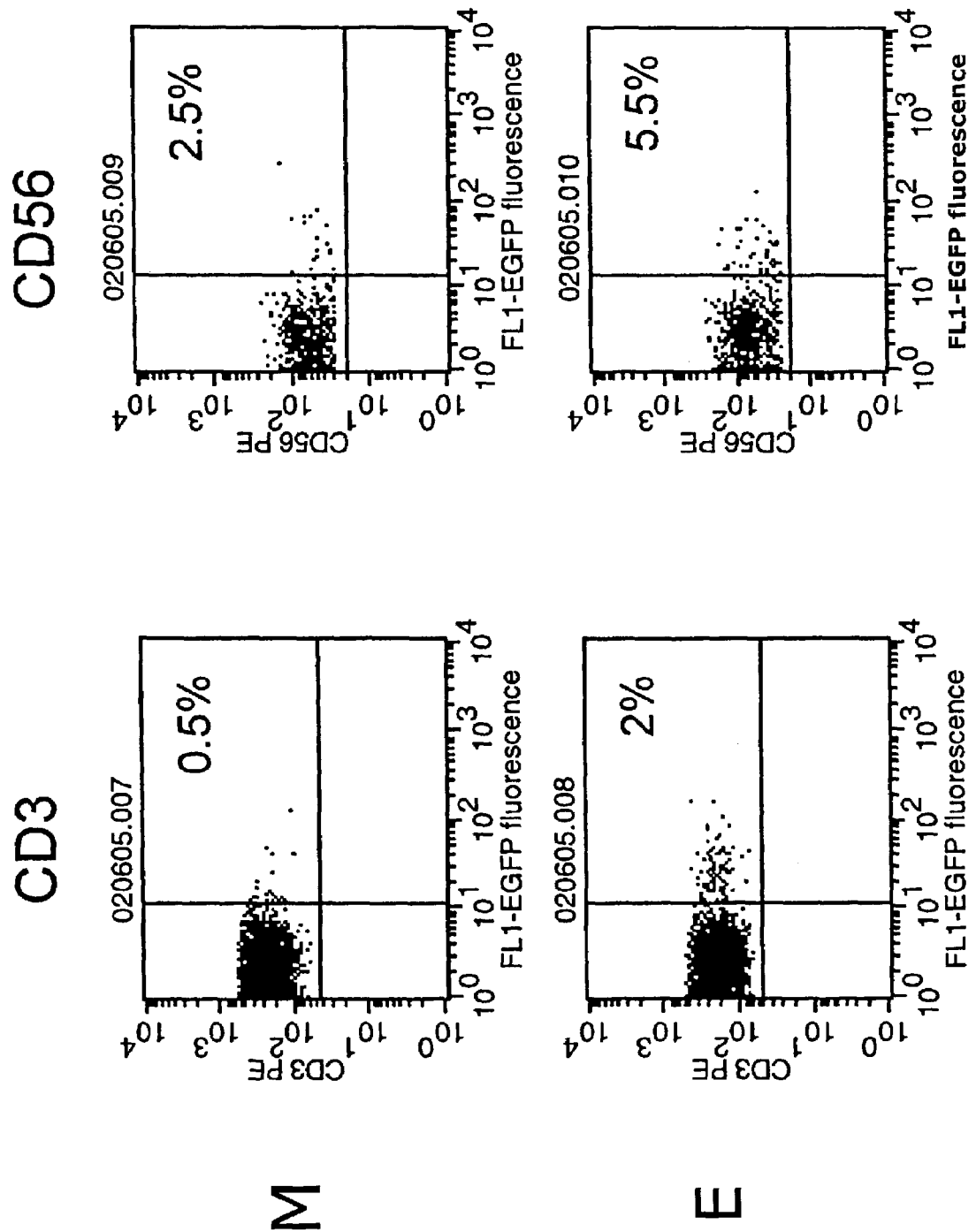

FIG. 23 shows the results of the EGFP analysis and phenotypic analysis of the transfected embryonic stem cells of Example 8, without feeder (A) and with feeder (B).

FIG. 24 shows the results of the EGFP analysis and phenotypic analysis of the PBMC electroporated according to the method of Example 9

Figure 25:
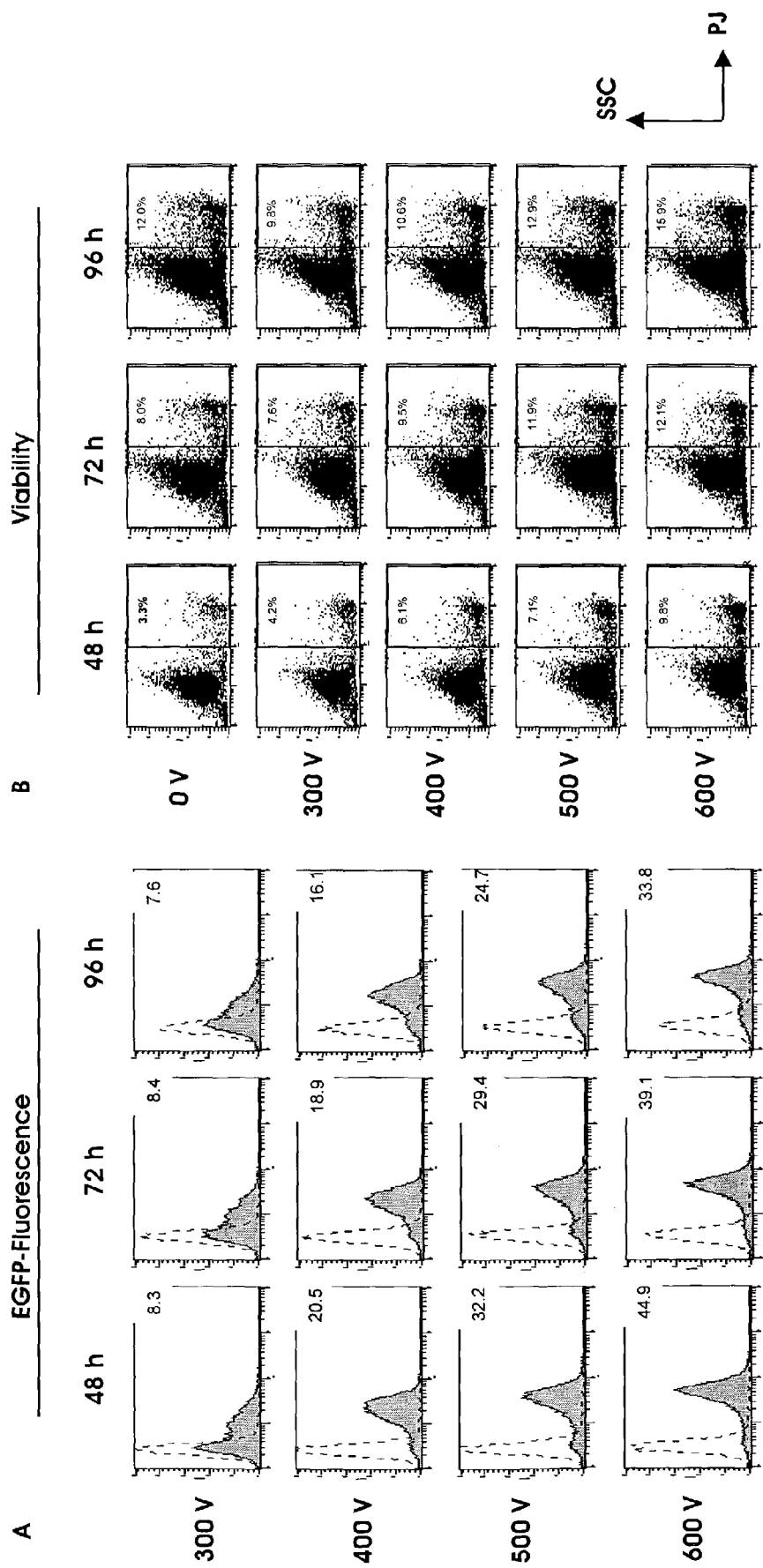

FIG. 25: mRNA-electroporation of Mo-DC at the μs-range (Example 10B)

A: Influence of voltage on transfection efficiency. Immature Mo-DC were electroporated for 500 μs at the indicated voltage using the machine MULTIPORATOR® (Eppendorf, Hamburg, Germany), which delivers exponential decay pulse. Immediately after that terminal maturation was induced by addition of IL-1β, IL-6, TNF-α and PGE$_2$. Transfection efficiency was determined at the indicated time by FCM analysis. The dashed line shows the fluorescence of Mo-DC transfected with EGFP mRNA. The dotted line represents negative control. The numbers in the figure indicate the mean fluorescence intensity (MFI).

B: Influence of voltage on viability. The figure shows the same Mo-DC as described above after staining with pro-pidium-jodide. The numbers in the figure indicate dead cells.

Figure 26:
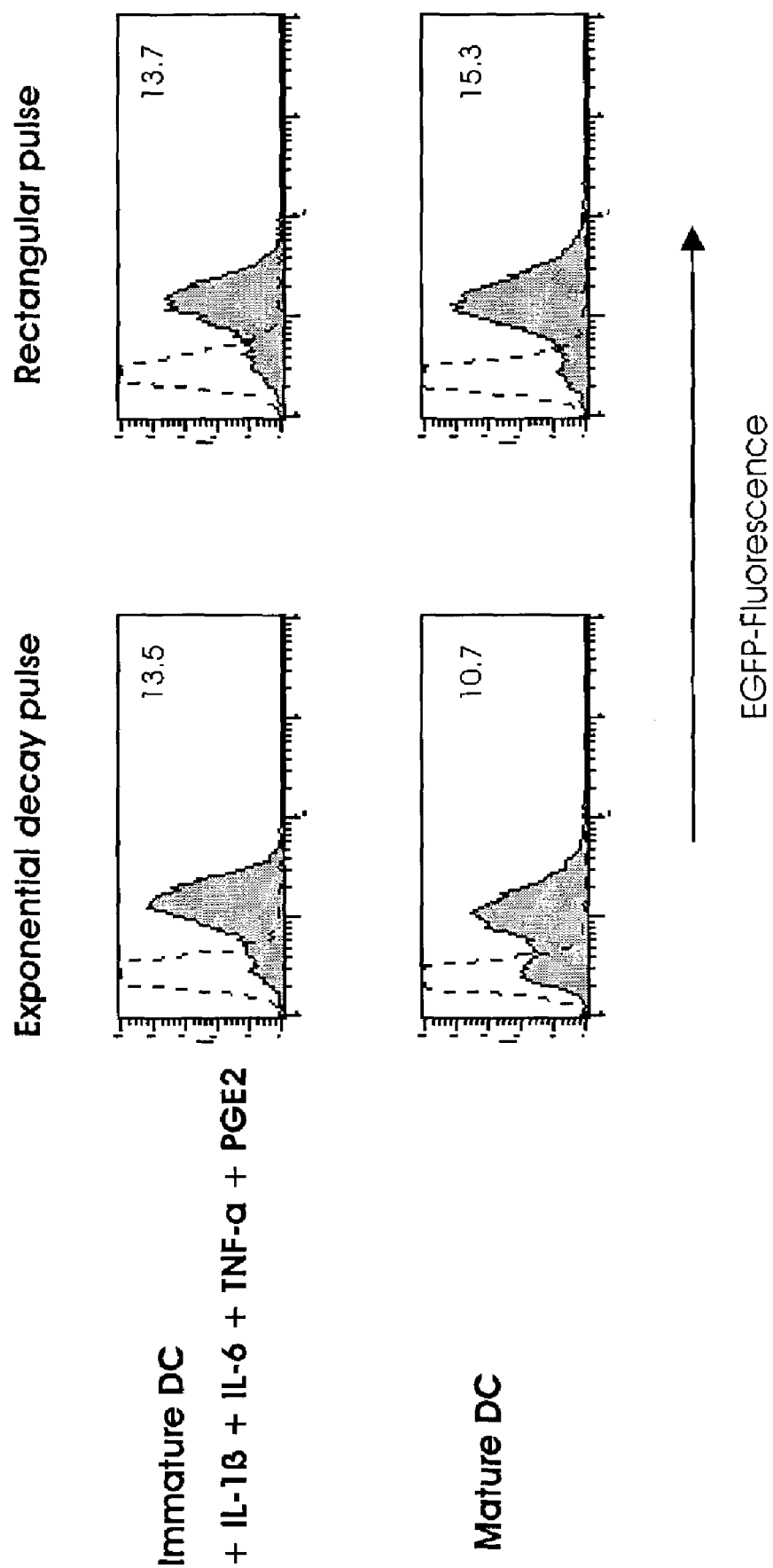

FIG. 26: Influence of pulse form on transfection efficiency (Example 10C) Immature Mo-DC were electroporated for 500 μs at 400 V using the machines MULTIPORATOR® (Eppendorf, Hamburg, Germany) and ECM830® (Genetronics BTX, San Diego, Calif., USA) delivering exponential decay or rectangular pulses, respectively. Immediately after that terminal maturation was induced by addition of IL-1β, IL-6, TNF-α and PGE$_2$. Mature DC were electroporated at the same settings. Transfection efficacy was determined by FCM analysis 2d post-electroporation. The dashed line shows the fluorescence of DC transfected with EGFP mRNA. The dotted line represents fluorescence of DC transfected with FluM1 mRNA. The numbers in the figure indicate the mean fluorescence intensity (MFI).

Figure 27:
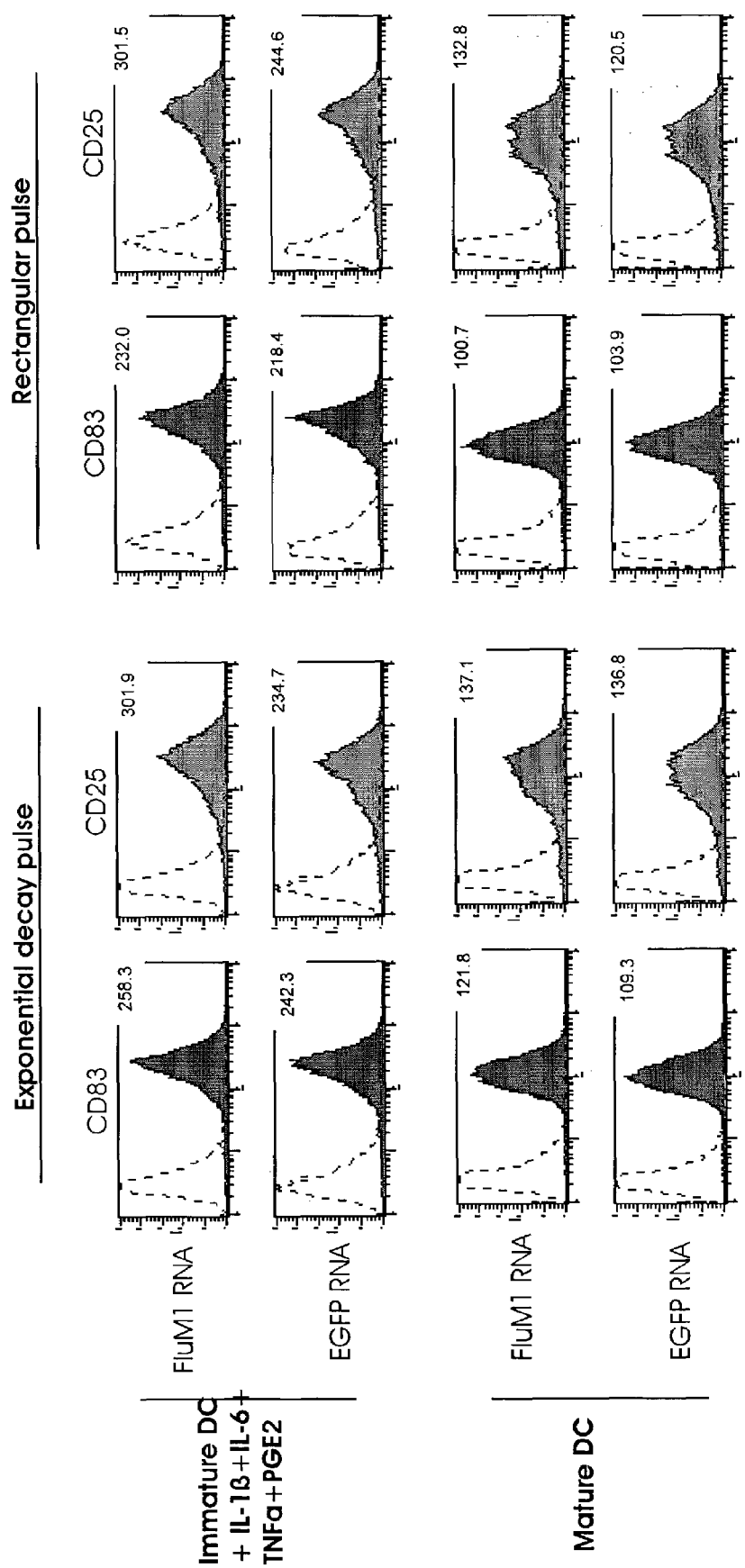

FIG. 27: Phenotypical analysis of Mo-DC 2d after mRNA-electroporation at the μs-range (Example 10C). Immature and mature Mo-DC were electroporated as described in FIG. 26/Example 10C. The dashed line shows the red-fluorescence of Mo-DC stained with the monoclonal antibodies specific for CD83 and CD25, respectively. The dotted line represents the isotype control. The number in the figure indicates the mean fluorescence intensity (MFI).

Figure 28:
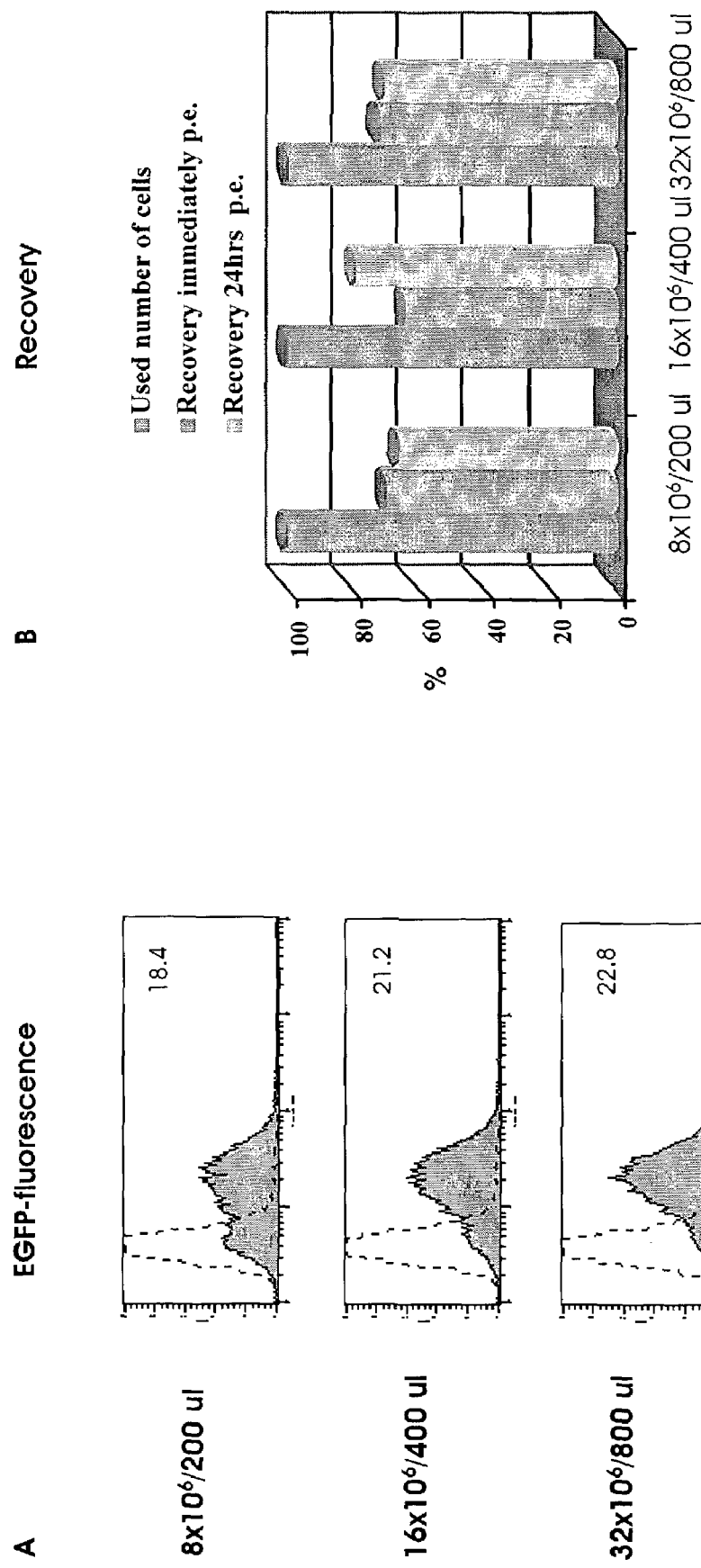

FIG. 28: Scale-up of the cell number per electroporation cuvette (Example 10D). Increasing numbers of mature Mo-DC were electroporated with EGFP mRNA in a 0.4 cm-gap-cuvette at 400 V for 500 μs using the machine MULTIPORATOR®. After 24 hrs transfection efficiency was determined by FCM-analysis of the EGFP-fluorescence.

A: The dashed line shows the fluorescence of Mo-DC transfected with EGFP mRNA. The dotted line represents negative control.

B: Recovery of cells (%) shown immediately post-electroporation (p.e.) and 24 h later.

Figure 29:
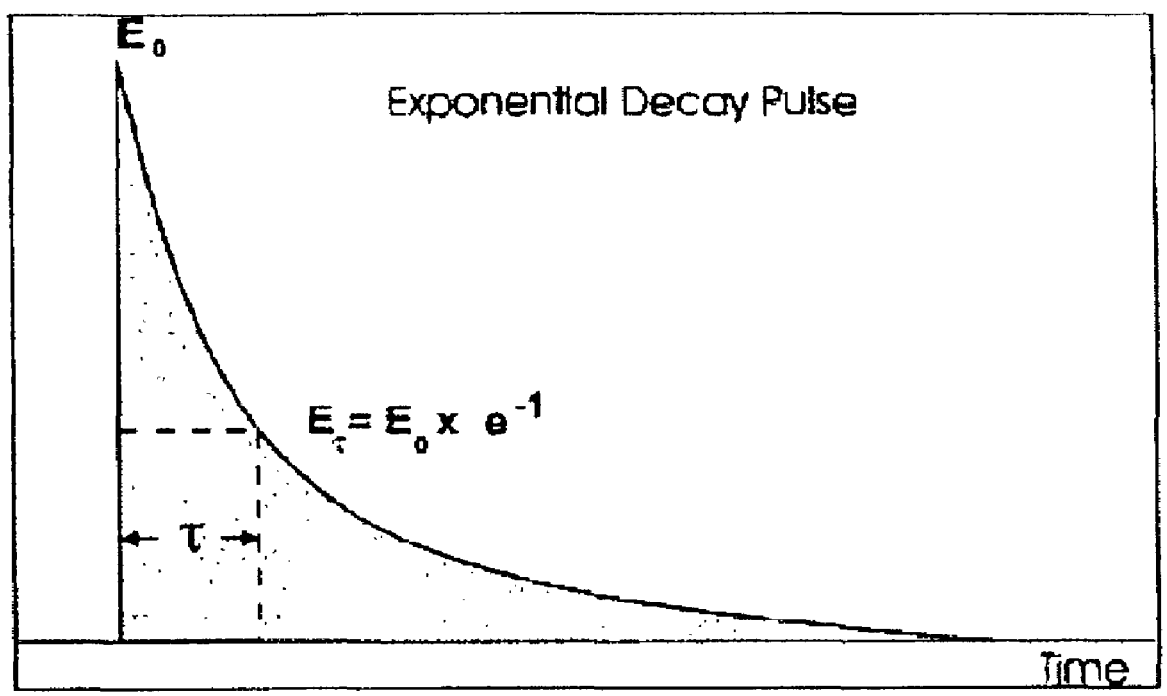

FIG. 29 Exponential decay pulse; relation with pulse time.

Figure 30:
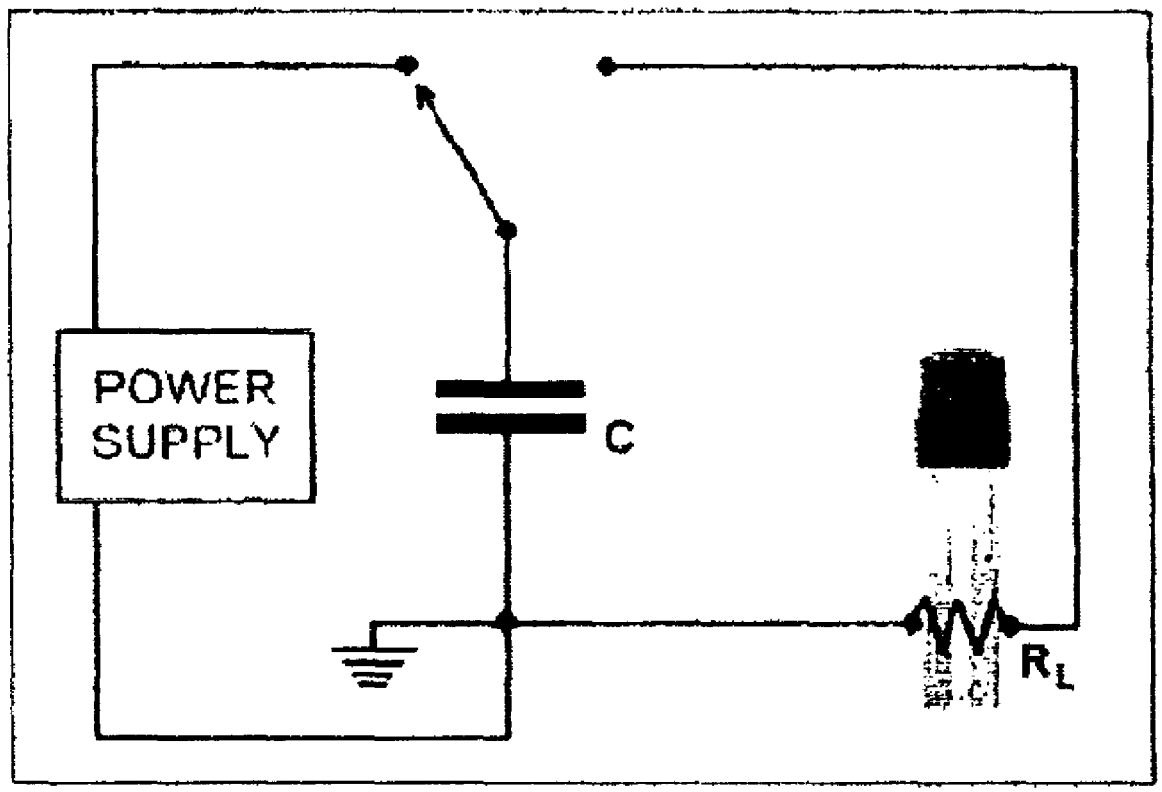

FIG. 30 Electroporation system; basic design for low voltage.

DETAILED DESCRIPTION OF THE INVENTION

In the method of embodiment (1) of the invention it is preferred that an conventional electroporation apparatus is utilized which provides for an exponential decay pulse. It is moreover preferred that the electroporation is performed at a voltage from 100 to 500 V, more preferably from 200 to 350 V, most preferably from 250 to 300 V. It is also preferred that the capacitance is 100 to below 300 μF, preferably 150 to 250 μF. The pulsing time is strongly dependent from the type of the tray (cuvette) and the amount of reaction mixture (cell suspension) in the cuvette and is generally below 50 ms, preferably below 40 ms. For a 4 mm cuvette and 200 μl reaction mixture the pulsing time is from 5 to 40 ms, preferably 1 to 25 ms, and most preferably 7 to 10 ms. For a different cuvette and/or different amount of reaction mixture volumes, different voltage and pulsing times can easily be determined by the skilled artisan.

In embodiment (2) of the invention so called "soft pulse" electroporation devices are utilized. With such devices the following settings a voltage of 300 to 600 V and a time of 100 μs to 1 ms are utilized which are believed to correspond to a capacitance of below 300 μF (although, due to the use of eukaryotic cell suspensions; a correct conversion is not possible). The pulse form provided by commercially available soft pulse electroporation devices may be a square wave pulse or an exponential decay pulse. Preferred settings for the soft pulse devices are 350 to 450 V for 300 to 600 μs.

In embodiments (1) and (2) of the invention the concentration of the cells in the suspension is $1\times10^3$ to $1\times10^9$ cells per ml, preferably $1\times10^5$ to $1\times10^9$ cells per ml. Even more preferred are $1\times10^5$ to $5\times10^7$ cells per ml, most preferably 1 to $4\times10^7$ cells per ml.

The linear polynucleotides to be transfected are preferably so-called "naked" polynucleodides, i.e. polynucleotides which are not complexed or stabilized by a ligand or the like. Linear polynucleotides to be utilized in the present invention include, but are not limited to, modified or unmodified, defined or undefined DNA, RNA or DNA-RNA hybrids and all kinds of modified variants thereof. The most preferred linear polynucleotides are mRNA. The above DNA-RNA hybrides are particularly suitable to repair or modify genes (Stepehnson, J., JAMA 281 (2), 119-122 (1999)). It is moreover preferred that the concentration of the polynucleotides to be transfected is $1\times10^{-7}$ to $1\times10^{-5}$ mmol/ml, preferably $4\times10^{-6}$ to $6\times10^{-6}$ mmol/ml.

All types of eukaryotic cells can be electroporated with the method of the invention, such as vertebrate cells including mammalian cells (such as human cells, rodent (mouse, rat) cells), non-vertebrate cells (such as cells of fish and worms), lower eukaryotes such as yeasts, filamentous fungi, ascomycetes, etc. The mammalian/human cells are preferably selected from non-hematopoietic cells including, but being not limited to, fibroblast and tumour cells, stem cells and derivatives thereof such as embryonic stem cells, hematopoietic stem cells and derivatives thereof, and hematopoietic cells including, but being not limited to, mononuclear cells, marrow $CD34^+$ progenitor derived dendritic cells, CD34+ progenitor derived Langerhans cell, monocycle-derived dendritic cells (Mo-DC), and most preferably are Mo-DC including, but being not limited to, immature Mo-DC and mature Mo-DC, but can also be applied to DC precursors or progenitors such as monocytes or CD34+ hematopoietic progenitor cells and also to embryonic stem cells. The method of the invention is also suitable to transduce primary bone marrow cells by RNA electroporation (it could be shown that mRNA electroporation of total bone marrow mononuclear cells is possible). The above mentioned precursor cells are electroporated with mRNA encoding the relevant antigen prior to (rapid) differentiation into dendritic cells. This strategy will be published in Ponsaerts et al. *Journal of Immunology* 2002, in press. This approach might also be of value for other types of precursor dendritic cells including CD123+ plasmacytoid dendritic cells or fresh CD11c+ blood dendritic cells that have a relative short halflife in vitro.

The linear polynucleotides used in embodiments (1) and (2) may be any functional nucleotide sequence exhibiting a certain effect in the eukaryotic cell, which includes polynucleotides encoding proteins or peptides to be expressed in the eukaryotic cells, polynucleotides being functional or regulatory sequences and the like. The proteins or peptides to be expressed in the eukaryotic cells may or may not have a direct function in the eukaryotic cells, i.e. the expressed protein or peptide changes the property of the transfected cell, or is merely expressed in the cell or secreted by the cell (e.g. is a reporter gene or a gene product in accordance with embodiment (6)). The above mentioned proteins or peptides encoded by the linear polynucleotides include, but are not limited to, tumor antigens, microbial antigens, viral antigens, immunostimulatory or tolerogenic molecules, anti-apoptotic molecules, adhesion and homing molecules and antigen processing molecules. The above mentioned functional or regulatory sequences include, but are not limited to, differentiation-regulating genes, differentiation-associated genes and tissue specific genes. Examples of the above proteins or peptides encoded by the linear polynucleotides are Reportergenes such as EGFP (Enhanced green fluorescent protein; SEQ ID NOs:1 and 2) etc.; Tumor/Viral Antigens such as WT1 (Wilms tumor 1 protein; SEQ ID NOs:3 and 4), E6 (Human Papilloma Virus E6 protein; SEQ ID NOs:5 and 6), E7 (Human Papilloma Virus E7 protein; SEQ ID NO:7 and 8), env (Human Immunodefficiency Virus env protein; SEQ ID NO:9), gag (Human Immunodefficiency Virus gag protein SEQ ID NO:10), tat(WT) (Human Immunodefficiency Virus tat(WT) proteins; SEQ ID NO: 11) tat(SLT) (Human Immunodefficiency Virus tat(SLT) protein SEQ ID NO:12), Nef (Human Immunodefficiency Virus Nef protein; SEQ ID NO:13), Ref (Human Immunodefficiency Virus Ref protein; SEQ ID NO:14); Melan-A/MART1 (Melanoma antigen Melan-A; SEQ ID NOs:15 and 16); MAGEAL1 (Melanoma antigen 1; SEQ ID NOs:17 and 18); MAGEA3 (Melanoma antigen 3; SEQ ID NOs:19 and 20) etc.; Cytokines such as GM-CSF (Granulocyte-macrophage colony stimulating factor; SEQ ID NOs:21 and 22), IL-2 (interleukin 2; SEQ ID NOs:23 and 24) etc; and Genes for Stem Cells such as Nkx2.5 (CSX: cardiac-specific homeo box; SEQ ID NOs:25 and 26), Notch (Notch homolog 1; SEQ ID NOs:27 and 28), BAALC (brain and acute leukemia, cytoplasmic Locus; SEQ ID NOs: 29 and 30), Wnt genes, GATA-4, GABA, desmine, cardiac troponine, etc.

For the electroporation, the following parameters were most preferred: a 4 mm cuvette with 200 μl of cell suspension and we shock the cells using 300 volts and a capacitance of 150 μF (pulse time 8-10 ms). These are optimal parameters for both leukemic K562 cells and different types of DC, both progenitor- and monocyte-derived DC. In the optimization process, other parameters were also checked, e.g., by ranging the voltage and the capacitance, as well as the volume in the cuvette, resulting in shorter or longer pulse times. In summary the following parameters for efficiency and toxicity of RNA electroporation were found:

300 V-150 μF-200 μl-8 ms
450 V-150 μF-200 μl-8 ms

The common denominator for RNA electroporation is the low voltage (range 100 V-450 V), combined with a low capacitance (150 to below 300 μF) (which is in contrast to DNA settings, for which a high capacitance is required) and a low electroporation volume (200 μl) to increase cell concentration.

Electroporation and incubations are all performed at room temperature and cells are resuspended in serumfree buffer (e.g. IMDM, RPMI, a serum reduced buffer (e.g. Opti-MEM®) or in optimized electroporation buffer Optimix® purchased from EquiBio, UK cat n# EKIT-E1). The electroporator type is Easyject Plus® (EquiBio) which only delivers exponential decay pulses. In Examples 2-4 a Gene Pulser II® (Biorad) was used. Moreover, in Example 10 so-called "soft pulse" electroporators (such as Multiporator of Eppendorf and ECM 830 of Genetronix BTX) are used.

The significant decrease in toxicity observed with mRNA electroporation could in part be explained by the less stringent electrical settings required for introduction of the RNA (Table 1). Nevertheless, mRNA electroporation performed at stringent DNA settings resulted in a lower cell toxicity as well, suggesting that cell toxicity is not solely due to the electroporation procedure itself, but can also be related to the nature of the introduced nucleic acids. Moreover, co-introduction of bacterial contaminants (e.g. LPS) often found in plasmid preparations, could affect cell viability (Gordillo, G. M., Transpl. Immunol., 7:83-94 (1999)).

In an attempt to compare DNA and mRNA loading of DC, it was unexpectedly observed that a nonspecific stimulation of the TIL clone with plasmid DNA- but not with mRNA-electroporated 34-DC and 34-LC (FIG. 6), which could be abolished by DNase I treatment of the plasmid DNA. Although this stimulatory effect of plasmid DNA confounded data interpretation, the impact of this phenomenon on DC loading with respect to antigen-presenting capacity needs further investigation. Possible involvement of immunostimulatory sequences present in plasmid DNA (i.e. unmethylated CpG motifs) should be considered (Klinman, D. M. et al., Proc. Natl. Acad. Sci. USA, 93:2879-2883 (1996); Klinman, D. M. et al., Vaccine, 17:19-25 (1999)).

Although mRNA lipofection was overall less efficient than mRNA electroporation for loading DC, especially 34-DC and 34-LC, these data were derived from experiments with only one cationic lipid, i.e. DMRIE-C. Therefore, we cannot exclude the possibility that other lipids would accomplish comparable, or even higher, efficiencies of transfection and/or of MHC class I-restricted antigen loading of Mo-DC, 34-LC or 34-DC as compared to mRNA electroporation. Using passive mRNA pulsing, we were not able to detect any EGFP expression nor CTL activation by any type of DC examined. Therefore, these results seem somewhat in contrast to the findings of Nair et al., Nat. Biotechnol., 16:364-369 (1998) who showed in pulsing experiments that immature Mo-DC can take up mRNA without the use of a transfection agent, and subsequently prime tumor-specific CTL in vitro. It is possible that in the Experiment of Nair et al. passive RNA pulsing of DC lead to effective RNA transfection in a substantial portion of DC as protein expression cannot be detected.

In conclusion, it is shown that IVT mRNA-based electroporation is a highly efficient and simple nonviral method to gene-modify human Mo-DC, 34-DC and 34-LC with tumor antigens. The technique described in this study can serve applications in DC-based tumor vaccine development and in other gene transfer protocols requiring high-level short-term transgene expression in hematopoietic cells.

EXAMPLES

Materials and Methods

Electroporation Devices:

Normal pulse: EasyjecT PLUS D2000 model SHV (220V; exponential decay pulses) was purchased from EquiBio Ltd. (cat # EJ-002, Action Court, Ashford Road, Ashford, Middlesex, TW15 1XB, U.K). The EasyjecT PLUS is fully microprocessor controlled via a bench top remote control unit, featuring an LCD display, membrane keypad and "Smart Card" reader/recorder. Hard copies of the parameters and initiated pulse values can be taken using the EasyjecT printer (included in the EasysyjecT PLUS). This information is invaluable in confirming your experimental procedure and giving results assured information. The EasyjecT PLUS includes a multitude of safety and operating detection features to enable safe operation without compromising the experimental procedure. Features includes:—Pre-Arc detection, open and short circuit detection, pre-pulse impedance measurement linked to a fully enclosed electroporation chamber. The programming gives visual and audible alarms if unsafe or incorrect information is measured or programmed. The EasyjecT is designed to deliver single or double exponential decay pulses. The EasyjecT PLUS has in addition the unique "double pulse" technology. This has been beneficial in certain cases where single pulse experiments have resulted in unsuccessful or disappointing transformations. Detailed specifications of the EasyjecT PLUS: Output Voltage: 100-3500 Volts (50V steps) in high voltage mode or 20-450 Volts (2V steps) in low voltage mode. Shunt resistor: 20 Ohms—Infinite (10 values). Capacitance range: 0.5 μF/25 μF in high voltage mode or 150-3000 μF in low voltage mode. Pulse time: 10 μs to 7 seconds. DOUBLE PULSE facility with inter pulse time 0 to 30 s. Program storage: 8 internal or 8 per smart card. Safety detection monitoring by visual and audible alarms for open and short circuit situations also if arcing should occur. Printer is included. Dimensions: Main unit (425×220×510 mm) Key Pad (100×270×35 mm) Chamber (260×67×92 mm) Power 190-250 Volts or 90-220 Volts Max 250 Watts. Wave Form: Decaying exponential waveform with RC time constant dependant upon capacitor, sample and shunt resistor selected. In Examples 2-4 Gene Pulser II (Biorad) was used.

Soft pulse: Multiporator® (Eppendorf, Hamburg, Germany), exponential decay pulse and ECM830® (Genetronics BTX, San Diego, Calif., USA), Rectangular pulse.

Electroporation cuvettes: Throughout the experiments with EasyjecT PLUS D2000, sterile 4 mm electroporation cuvettes with cap (EquiBio, UK cat # ECU-104) were used. Each cuvette is individually wrapped and gamma-irradiated. Specifically designed sterile pipettes were used to further improve aseptic procedures. Total capacity is 800 µl.

Electroporation medium: Just before electroporation, cells were resuspended in Optimix® medium (EquiBio, UK, cat #EKIT-E1). Optimix is a QC-tested fully optimised medium, designed for the electroporation of eukaryotic cells. Optimix improves both transfection efficiencies and survival rates over phosphate-buffered saline (PBS) or other standard culture medium. The composition of Optimix has been carefully formulated to help protect cells during the electroporation process, also providing additional salts and critical molecules that help in the regeneration process following the destabilisation caused by the electrical discharge through the cell. The Optimix kit is ready to use and contains enough material for approx. 24 experiments. The kit is shipped at ambient temperature, however, it is important that some of the components are stored at either 4° C. or −20° C. on arrival. Optimix comprises 1×200 ml of washing solution, 4×2.5 ml of Optimix, 4×ATP and 4×glutathione. Prior to use use, 5.5 mg ATP and 7.7 mg gltathione is mixed with 2.5 ml Optimix buffer and frozen in aliquots at −20° C.

Electrical parameters: Unless otherwise mentioned, typical mRNA electroporation settings were 300 V, 150 µF and an internal shunt resistance is put at infinity (+∞). Total volume in the cuvette is 200 µl containing 2-5 million cells resuspended in Optimix medium.

Electroporation mathematics: The electric field E is expressed in Volts per centimeter using the following formula:

$$E = V.d^{-1}$$

For which V is the output voltage of the electroporation apparatus and d is the distance between the electrodes of the cuvette.

Pulse time ($\tau$) is by definition the elapsed time, in seconds, from the beginning of the pulse, when the electric field is maximum ($E_0$) until the electric field has decreased to $e^{-1}$ (0.368) of the initial value $E_0$. Practically, this value is measured by the microprocessor of the electroporation unit. The pulse time for an ideal system can be calculated as follows:

$$\tau = R.C$$

in which C is the capacitance (expressed in Farads) and R is the resistance of the electrical circuit. The pulse time gives an estimation of the duration of the membrane pore formation process and is inversely correlated by the volume of electroporation medium in the cuvette and the directly correlated with the cell concentration in the cuvette and the resistance of the medium.

Cell lines: T2 cells (TAP-deficient, HLA-A2$^+$, TxB hybrid), EBV-LG2 (HLA-A2$^-$ EBV-transformed B lymphocytes), and SK23-MEL (Melan-A$^+$ HLA-A2$^+$ melanoma cell line) were kindly provided by Dr. Pierre Van der Bruggen (Ludwig institute for Cancer Research, Brussels, Belgium). K562 cells were obtained from the American Type Culture Collection (ATCC n° CCL-243, Rockville, Md., USA). Cell lines were cultured in complete medium consisting of Iscove's medium (IMDM) supplemented with L-glutamine (2 mM), penicillin (100 U/ml), streptomycin (100 µg/ml), amphotericin B (1.25 µg/ml Fungizone) and 10% fetal calf serum (FCS; Sera Lab, Sussex, UK). Cells were maintained in logarithmic phase growth at 37° C. in a humidified atmosphere supplemented with 5% $CO_2$. All cell culture reagents were purchased from Gibco BRL (Paisley, UK).

Melan-A-specific CTL clone: The CD8$^+$ TIL 1235 clone recognizing the immunodominant HLA-A0201-restricted Melan-$A_{27-35}$ epitope (AAGIGILTV; SEQ ID NO:34) was a kind gift of Dr. J. Wunderlich (NIH, Bethesda, USA) and was cultured as described earlier with minor modifications (Reeves, M. E. et al., Cancer Res., 56:5672-5677 (1996)). Briefly, the TIL clone was maintained in AIM-V medium (Gibco BRL) supplemented with 5% pooled human AB serum (Sigma, Bornem, Belgium) and 500 IU/ml interleukin (IL)-2 (R&D Systems, Minneapolis, Minn., USA) and used as responder population in DC coculture experiments.

Source of primary cells: Bone marrow (BM) samples were aspirated by sternal puncture from hematologically normal patients undergoing cardiac surgery, after informed consent. Peripheral blood mononuclear cells (PBMC) were obtained from healthy volunteers or hemochromatosis patients. The 6 PBMC donors used in this study are designated by letters A to F. Mononuclear cells were isolated by Ficoll-Hypaque gradient separation (LSM, ICN Biomedicals Inc., Costa Mesa, Calif., USA). Monocytes were directly isolated and used for DC culture, as described below. PBMC for DC/T-cell cocultures were cryopreserved in a solution consisting of 90% FCS and 10% DMSO and stored at −80° C. until use. CD34$^+$ cell sorting: After Ficoll-Hypaque separation, mononuclear BM cells were indirectly stained using supernatant of the 43A1 hybridoma (anti-CD34) kindly donated by Dr. H-J. Bühring, University of Tübingen, Germany (Buhring, H. J. et al., Leukemia, 5:854-860 (1991)), followed by fluorescein isothiocyanate (FITC)-conjugated rabbit anti-mouse immunoglobulins (DAKO, Glostrup, Denmark). The CD34 labeled cells were then sorted on a FACStar$^{PLUS}$ cell sorter (Becton Dickinson, Erembodegem, Belgium) equipped with an air-cooled argon ion laser ILT model 5500-A (Ion Laser Technology, Salt Lake City, Utah, USA). Sort windows were set to include cells with low side scatter and with positive green fluorescence (CD34$^+$). Purities of >95% were routinely obtained.

Figure 3B:
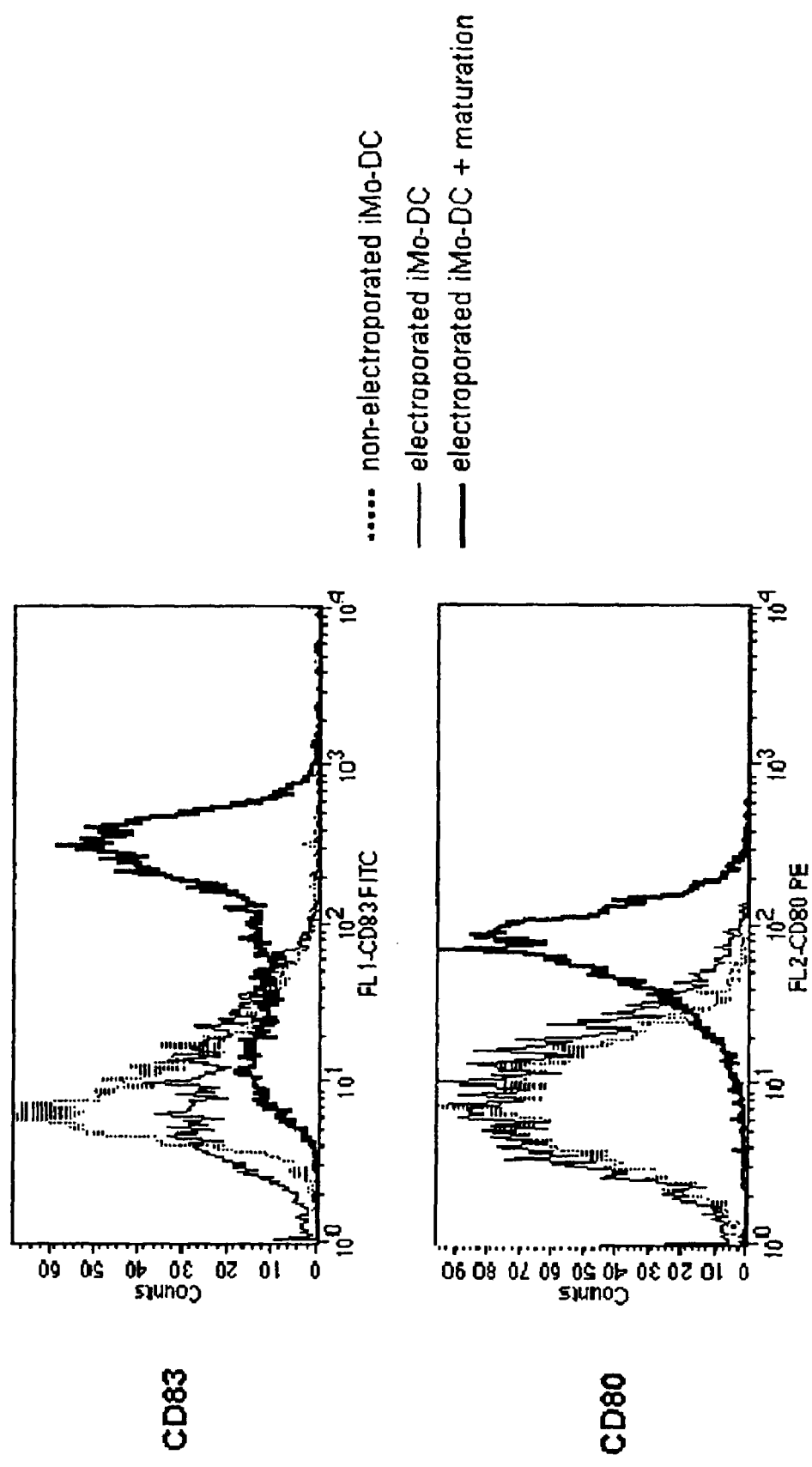
Figure 3C:
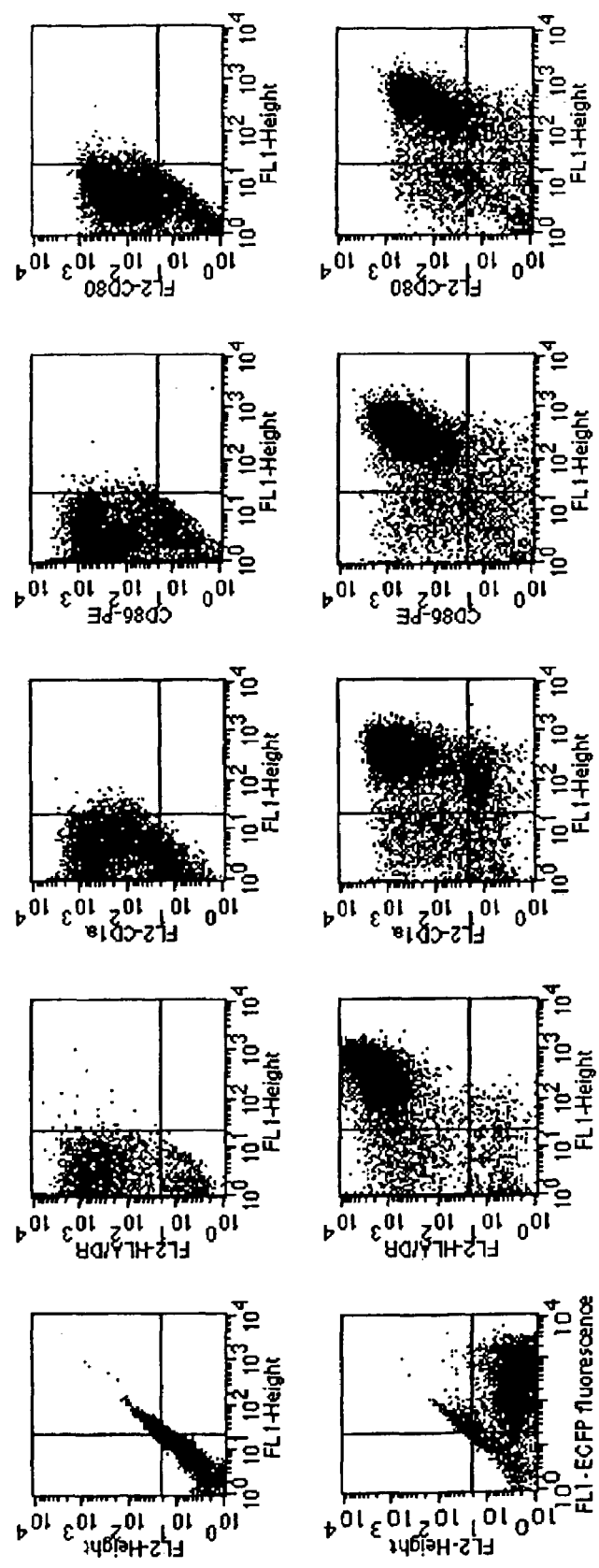

In vitro culture of DC: 34-DC cultures were cultured as described previously (Lardon, F. et al., Immunology, 91:553-559 (1997)). Briefly, 1-2.10$^5$ CD34$^+$ cells were cultured in 2 ml of complete medium supplemented with 100 ng/ml granulocyte-macrophage colony-stimulating factor (GM-CSF; Leucomax, Novartis Pharma, Basel, Switzerland), 2.5 ng/ml tumor necrosis factor (TNF)-α (Roche Molecular Biochemicals, Mannheim, Germany) and 50 ng/ml stem cell factor (SCF; Biosource, Nivelle, Belgium) until day 5; afterwards, SCF was replaced by 1000 U/ml IL-4 (R&D Systems), which was added for the next 5-9 days. After 12 days of culture, a 15-20 fold total cell expansion was observed and cells exhibited typical markers of mature DC including CD1a, CD80, CD86 and HLA-DR (FIG. 3C).

For 34-LC, we used the protocol described by Herbst, B. et al., Blood, 88:2541-2548 (1996). Briefly, sorted CD34$^+$ cells were first cultured for 8 days in complete medium containing 100 ng/ml IL-3, 100 ng/ml IL-6 and 50 ng/ml SCF (all from Biosource), followed by LC differentiation in GM-CSF (100 ng/ml) and IL-4 (1000 U/ml) for the next 4 weeks. After 25 days of culture, a 75-100-fold increase in the total number of nucleated cells was observed and cells expressed high levels of CD1a and CD40, intermediate levels of HLA-DR and low levels of CD80 and CD86 and were able to efficiently take up FITC-dextran at 37° C. (data not shown).

Immature monocyte-derived DC (iMo-DC) were generated from PBMC as described by Romani, N. et al., J. Exp. Med., 180:83-93 (1996). Briefly, PBMC were allowed to adhere in AIM-V medium for 2 h at 37° C. The non-adherent fraction was removed, and adherent cells were further cultured for 5-7 days in IMDM supplemented with 2.5% autologous heat-inactivated plasma. GM-CSF (100 ng/ml) and IL-4 (1000 U/ml) were added to the cultures every 2-3 days starting from day 0. Maturation of iMo-DC was induced by adding 2.5 ng/ml TNF-α and 100 ng/ml lipopolysaccharide (LPS; Sigma) for 24 h starting from day 6 of the Mo-DC culture.

Alternatively, monocytes derived from PBMCs were allowed to adhere in AIM-V medium (Gibco BRL, Paisly, UK) for 2 h at 37° C. in 6-well culture plates ($20 \times 10^6$ PBMC/well). After careful removal of the non-adherent fraction, cells were cultured in serum-free AIM-V medium supplemented with 100 ng/ml GM-CSF (Leucomax, Novartis Pharma, Basel, Switzerland) for 2 days. To obtain mature DC, poly-I:C (Sigma, Cambridge, UK) was added 24 hours after starting the culture at a concentration of 25 µg/ml. The typical yield and purity of the DC culture was $1-2 \times 10^6$ cells/well containing 60-70% of DC. For electroporation experiments, monocytes were isolated from PBMC by magnetic isolation using CD14 microbeads (Miltenyi Biotec, Bergisch Gladbach, Germany) according to manufacturer's instructions. Routinely, $4-8 \times 10^6$ monocytes were obtained starting from $100 \times 10^6$ PBMC with purity levels ≧85%.

HLA-A typing of DC: HLA-A2 subtyping was determined on BM-derived mononuclear cells and PBMC by indirect staining with the supernatant of the BB7-2 hybridoma (anti-HLA-A2; ATCC), followed by FITC-conjugated rabbit anti-mouse immunoglobulins (DAKO). HLA-A2 staining was analyzed by flow cytometry using a FACScan analytical flow cytometer (Becton Dickinson, Erembodegem, Belgium).

Synthetic peptides: An influenza virus-specific HLA-A*0201-restricted matrix protein M1 peptide (M1; amino acids (aa) 58-66, GILGFVFTL; SEQ ID NO:32) was used for activation or for detection of matrix protein M1 peptide specific T-cells when pulsed on respectively DC and T2 cells. A human papillomavirus (HPV) HLA-A2-restricted E7 protein-specific peptide (E7; amino acids (aa) 11-20, YMLDLQPETT; SEQ ID NO:33) was used in control experiments when pulsed on T2 cells. Melan-A peptide (MA; aa 27-35, AAGIGILTV; SEQ ID NO:34) was also used. Peptides (>95% pure) were purchased from Sigma-Genosys (Cambridge, UK). Both peptides were dissolved in 100% DMSO to 10 mg/ml, further diluted to 1 mg/ml in serum-free IMDM and stored in aliquots at −70° C. Peptides were used at a final concentration of 20 mM. The peptides (>95% pure) were purchased from Sigma-Genosys (Cambridge, UK). The peptides were dissolved in 100% DMSO to 10 mg/ml, further diluted to 1 mg/ml in serum-free IMDM and stored in aliquots at −80° C. The peptides were used at a final concentration of 20 µM.

Peptide-pulsing of DC: T2 cells, HLA-A2⁺ iMo-DC or DC were washed twice with IMDM and subsequently incubated ($2 \times 10^6$ cells/ml) for 1 to 2 h at room temperature in 5 ml conical polystyrene tubes or 15 ml conical tubes with 20 µg/ml peptide in serum-free IMDM medium supplemented with 2.5 µg/ml β2-microglobulin (Sigma). Afterwards, the cells were washed and used respectively as stimulators for PBMC or as restimulators in cytokine release assays.

Plasmids: For plasmid cDNA transfection, a pEGFP-N1 plasmid (CLONTECH Laboratories, Palo Alto, Calif., USA) was used encoding an enhanced green fluorescent protein (EGFP) gene under the control of a CMV promoter plasmid pGEM4Z/EGFP/A64 (kindly provided by Dr. E. Gilboa, Duke University Medical Center, Durham, N.C., USA) contained the EGFP gene under the control of T7 promoter. Plasmid pcDNA1.1/Melan-A contained the Melan-A/MART-1 gene driven by a CMV promoter was kindly provided by Dr. Pierre Van der Bruggen. pcDNA1.1/Amp (Invitrogen, Carlsbad, Calif., USA) was used as a backbone control vector. Plasmid pCMV-Luciferase (CLONTECH Laboratories, Palo Alto, Calif., USA) carried a luciferase gene under the control of a CMV promoter and was used as a control plasmid. Plasmid pGEM4Z/M1/A64 (kindly provided by Dr. A. Steinkasserer, University of Erlangen, Erlangen, Germany) encoding an influenza M1 gene under the control of a T7 promoter (SEQ ID NO:31). Plasmids were propagated in E. Coli strain DH5α (Gibco BRL) or supercompetent cells (Stratagene, La Jolla, Calif., USA) and purified on endotoxin-free QIAGEN®-tip 500 columns (Qiagen, Chatsworth, Calif., USA).

Production of in vitro transcribed (IVT) mRNA: For in vitro transcriptions, plasmids were linearized, purified using a Genieprep kit (Ambion, Austin, Tex., USA) or a PCR purification Kit (Qiagen) and used as DNA templates for the in vitro transcription reaction. pcDNA1.1/Melan-A was used as such for in vitro transcription under the control of a T7 promoter. EGFP cDNA, isolated as a 0.8 kb HindIII-NotI fragment from pEGFP-H1, was first subcloned into pcDNA1.1/Amp and subsequently cloned as a BamHI-XbaI fragment into pSP64 (Promega, Madison, Wis., USA) that allows in vitro transcription under the control of an SP6 promoter. Transcription was carried out in a final 20-100 µl reaction mix at 37° C. for 3-4 h using the SP6 MessageMachine kit (Ambion) to generate 5' m⁷GpppG-capped IVT mRNA. Transcription reactions with Spe I (MBI Fermentas, St. Leon Rot, Germany) linearized plasmids pGEM4Z/EGFP/A64 or pGEM4Z/M1/A64 as templates were carried out in a final 20 µl reaction mix at 37° C. using the T7 MessageMachine Kit (Ambion, Austin, Tex., USA) to generate 5' capped in vitro transcribed (IVT) mRNA. Purification of IVT mRNA was performed by DNase I digestion followed by LiCl precipitation and 70% ethanol wash, according to manufacturer's instructions. For each experiment, at least three different batches of mRNA were used. mRNA quality was checked by agarose-formaldehyde gel electrophoresis. RNA concentration was assayed by spectrophotometrical analysis at $OD_{260}$. RNA was stored at −80° C. in small aliquots (1 µg/µl).

Cell transfections: Prior to electroporation, K562 cells were washed twice with serum-free IMDM and resuspended to a final concentration of $5-10 \times 10^6$ cells/ml in Opti-MEM (Gibco BRL). After phenotypic analysis (performed in order to confirm the presence of CD1a⁺HLA-DR⁺ DC in the cultures), 34-DC, 34-LC and Mo-DC were routinely harvested after respectively 12, 25 and 6 days of culture (unless stated otherwise), washed twice with serum-free IMDM, and resuspended to a final concentration of $10-40 \times 10^6$ cells/ml in Opti-MEM. Subsequently, 0.5 ml of the cell suspension was mixed with 20 µg of IVT mRNA, and electroporated in a 0.4 cm cuvette using an Easyject Plus device (EquiBio, Kent, UK). In K562 cells, various voltages, capacitances and electroporation volumes were compared in order to assess their effect on mRNA transfection efficiency (see Results section). Electroporation of mRNA into CD14 microbead-isolated monocytes was done as described in Van Tenderloo, V. P. et al., Blood, 98:49 (2001), with minor modifications. Briefly, prior to electroporation, CD14 microbead-isolated monocytes were washed twice with Optimix Washing Solution (EquiBio, Ashford, Middlesex, UK) and resuspended to a final concentration of $50 \times 10^6$ cells/ml in Optimix electroporation buffer (EquiBio). Subsequently 0.2 ml of the cell suspension was mixed with 20 µg of IVT mRNA and electroporated in a 0.4 cm cuvette at 300 V and 150 µF using an Easyject Plus device (EquiBio). Plasmid DNA electroporation was performed as previously described (Van Tendeloo, V. F. I. et al., Gene Ther., 5:700-707 (1998)). After electroporation, fresh complete medium (including cytokines for DC) was added to the cell suspension and cells were further incubated at 37° C. in a humidified atmosphere supplemented with 5% $CO_2$.

Lipofection of mRNA was performed using the cationic lipid DMRIE-C (Gibco BRL) according to manufacturer's instructions with minor modifications (Van Tendeloo, V. F. I. et al., Gene Ther., 5:700-707 (1998)). Briefly, K562 cells were washed twice with serum-free IMDM and resuspended to a final concentration of $1-2.10^6$ cells/ml in Opti-MEM. 34-DC, 34-LC and Mo-DC were harvested after respectively 12, 25 and 6 days of culture, washed twice with serum-free IMDM, and resuspended to a final concentration of $1-2.10^6$ cells/ml in Opti-MEM. Five µg of IVT mRNA, diluted in 250 µl Opti-MEM, was mixed with DMRIE-C, also diluted in 250 µl Opti-MEM, at a lipid:RNA ratio of 4:1. After 5-15 min of incubation at room temperature in order to allow RNA-lipid complexation, lipoplexes were added to the cells and allowed to incubate for 2 hours at 37° C. Alternatively, 5-20 µg of IVT mRNA was pulsed to the cells in the absence of DMRIE-C for 3-4 h at 37° C. Plasmid DNA lipofection was performed as described previously (Van Tendeloo, V. F. I. et al., Gene Ther., 5:700-707 (1998)). After lipofection or passive pulsing, fresh complete medium (including cytokines for DC) was added to each well.

EGFP analysis: EGFP-transfected cells were checked for EGFP expression 24-48 h after transfection by flow cytometric (FCM) analysis. Briefly, cells ($1-5 \times 10^5$) were washed once in phosphate-buffered saline (PBS) supplemented with 1% FCS and resuspended in 0.5 ml of PBS supplemented with 1% BSA and 0.1% sodium azide. Ethidium bromide (EB) at a final concentration of 10 µg/ml was added directly prior to FCM analysis on a FACScan analytical flow cytometer (Becton Dickinson) to assess cell viability. For EGFP analysis in DC cultures, gating was performed on cells exhibiting a large forward scatter (FSC) and side scatter (SSC) profile, i.e. DC, in order to allow exclusion of contaminating autologous lymphocytes. Gated DC were then evaluated for EGFP expression.

Immunophenotyping of DC: Immunophenotyping was performed as described previously (Van Tendeloo, V. F. I. et al., Gene Ther., 5:700-707 (1998)). The following monoclonal antibodies were used: CD1a-fluorescein isothiocyanate (FITC) (Ortho Diagnostic Systems, Beerse, Belgium), CD1a-phycoerythrin (PE) (Caltag Laboratories, San Francisco, Calif., USA), CD14-PE, HLA-DR-PE, HLA-DR-FITC (PharMingen, San Diego, Calif., USA), CD4-PE, CD80-PE (Becton Dickinson), CD80-FITC (PharMingen, San Diego, Calif., USA), CD40-FITC (BioSource, Zoersel, Belgium), CD86-PE (PharMingen, San Diego, Calif., USA), CD86-FITC (Serotec, Oxford, UK), CD13-FITC (DAKO), CD14-FITC (Becton Dickinson, Erembodegem, Belgium) and the non-conjugated CD83 (HB-15 clone; Immunotech, Marseille, France). Immunophenotyping with CD83 was followed by staining with a secondary rabbit anti-mouse (RAM)-FITC antibody (Dako, Glostrup, Denmark). Nonreactive isotype-matched antibodies (Becton Dickinson) were used as controls. Ethidium bromide was added prior to FCM analysis on a FACScan analytical flow cytometer (Beckton Dickinson) to assess cell viability and to exclude dead cells from the analysis. Gating was also performed to exclude remaining lymphocytes in the DC cultures. In particular, for immunophenotyping of enhanced green fluorescent protein (EGFP) mRNA-electroporated DC, the following phycoerythrin (PE)-labeled monoclonal antibodies were used: CD1a-PE, HLA-DR-PE, CD80-PE, CD14-PE, CD86-PE, and the secondary RAM-PE antibody (Dako, Glostrup, Denmark) for CD83 staining.

Interferon (IFN)-γ release assay: 34-DC, 34-LC and iMo-DC were used as stimulator cells 24 h after transfection. To study the effect of maturation, 6-day-cultured iMo-DC were allowed to mature for 24 h in the presence of TNF-α and LPS prior to transfection and used as stimulators 24 h after transfection. Alternatively, iMo-DC were transfected with mRNA on day 6 of culture and, after 12-16 h to allow protein expression, TNF-α and LPS were added to induce final DC maturation. After an additional 24 h, mature transfected Mo-DC were used as stimulators. In some experiments, iMo-DC pulsed with the Melan-A, an irrelevant influenza M1 peptide or an irrelevant human papilloma virus E7 peptide were used as stimulators. Stimulators were either washed twice and resuspended in AIM-V medium supplemented with 10% pooled human AB serum and 40 IU/ml IL-2. Responder CTL were washed vigorously 3-4 times and resuspended in AIM-V medium. Then, CTL ($1 \times 10^5$ cells) were coincubated with stimulator cells ($1 \times 10^5$ cells) in 96-round bottom plates for 24 h at 37° C. in a total volume of 200 µl. Alternatively, stimulators and responder PBMC were washed and resuspended in IMDM+5% hAB serum. Then, responder PBMC ($1 \times 10^5$ cells) were coincubated with stimulator cells ($1 \times 10^4$ cells) in 96-well round-bottom plates for 6 hours at 37° C. in a total volume of 100 µl. Triplicate supernatant samples from these cocultures were tested for specific IFN-γ secretion by an IFN-γ ELISA (Biosource, Nivelle, Belgium). To normalize data, the background IFN-γ secretion (defined as IFN-γ released by the CTL exposed to unmodified DC) was subtracted from each of the observed measurements. Measurements are presented as IU/ml released by $10^5$ responder cells/24 h.

IFN-γ secreting cell assay: PBMC primed and cultured as described above ($1 \times 10^6$) were restimulated for 3 hours in 24-well plates with T2 cells ($1 \times 10^5$) pulsed with M1 peptide or E7 peptide as control. Next, IFN-γ-secreting cells were analyzed by a flow cytometric IFN-γ Secretion Assay Detection Kit (Miltenyi Biotec, Bergisch Gladbach, Germany) according to manufacturer's instructions. Cells were also stained with CD8-FITC (Becton Dickinson) and $5 \times 10^5$ cells were analyzed per sample by flow cytometry. Analysis was done by gating on the lymphocyte population.

Allogeneic mixed leukocyte reaction (MLR): Immature and mature DC were used for stimulation of allogeneic PBMC. Briefly, immature or mature DC were cocultured with $20 \times 10^6$ allogeneic PBMC (ratio 1:10) in 10 ml IMDM supplemented with 5% human (h) AB serum (Sigma) in T25 culture flasks. On day 4 of culture, 5 ml fresh medium (IMDM+5% hAB serum) was added to the cultures. On day 7 of culture, cells were analyzed for reactivity. For this, stimulated PBMC ($1 \times 10^5$ cells) were restimulated with PBMC from the DC donor ($1 \times 10^4$ cells) in 96-well round bottom plates for 6 hours at 37° C. in a total volume of 100 µl. Supernatant samples from these cocultures were tested for IFN-γ secretion by IFN-γ ELISA (Biosource, Nivelle, Belgium).

Induction of MHC class I-restricted influenza-specific T cells: M1 peptide-pulsed immature, M1 peptide-pulsed mature DC and matrix protein mRNA-electroporated mature DC were used for antigen-specific stimulation of PBMC.

Briefly, $2 \times 10^6$ antigen-loaded DC were cocultured with $20 \times 10^6$ autologous PBMC (ratio 1:10) in 10 ml IMDM supplemented with 5% hAB serum in T25 culture flasks. On day 4 of culture, 5 ml fresh medium (IMDM +5% hAB serum) was added to the cultures. On day 7 of culture, cells were analyzed for antigen specificity.

Example 1

A. Optimization of IVT mRNA transfection in K562 cell: In preliminary experiments to optimize mRNA electroporation, we used leukemic K562 cells, as these cells were readily transfectable by plasmid electroporation (Baum, C. et al., Biotechniques, 17:1058-1062 (1994)). The EGFP reporter gene was used to assess mRNA transfection efficiency. Various electroporation settings were tested and transfection efficiency was determined by FCM analysis of EGFP expression (FIG. 1A). Of all tested electrical settings, a voltage of 300 V combined with a capacitance of 150 µF in a total cuvette volume of 200 µl resulted in the highest EGFP expression (Table 1).

TABLE 1

Optimization of mRNA electroporation parameters in K562 cells

| | Electroporation | | | | |
|---|---|---|---|---|---|
| | voltage (V) | capacitance (µF) | cell volume (µl) | efficiency (%) | viability (%) |
| DNA | 260 | 1050 | 500 | 40 | 49 |
| | 300 | 150 | 200 | 28 | 85 |
| RNA | 300 | 150 | 200 | 89 | 85 |
| | 300 | 300 | 200 | 83 | 59 |
| | 260 | 1050 | 500 | 81 | 73 |
| | 250 | 1500 | 500 | 80 | 69 |

| | Lipofection | | | | |
|---|---|---|---|---|---|
| | lipid | lipid:DNA ratio | incubation time (h) | efficiency (%) | viability (%) |
| DNA | DMRIE-C | 3:1 | 6 | 26 | 88 |
| RNA | DMRIE-C | 4:1 | 2 | 22 | 80 |

K562 cells were transfected as described in the Materials and Methods section by electroporation or lipofection. Cells were analyzed 24 h after electroporation by FCM for EGFP expression to estimate transfection efficiency (=% EGFP$^+$ cells) as well as by ethidium bromide exclusion for cell viability. Results are the mean of four independent experiments each with a different IVT mRNA batch (standard error of the mean <2.5%).

The vast majority of the viable cell fraction expressed EGFP to a significant extent. The percentage of EGFP-expressing K562 cells was markedly higher following mRNA electroporation than following plasmid cDNA transfection, even when cDNA electroporation was performed at optimal DNA electroporation settings, i.e. 260 V and 1050 µF (FIG. 1A). Furthermore, mRNA electroporation at optimal settings showed a significantly reduced cell mortality rate as compared to cDNA electroporation at optimal settings (15% versus 51%, respectively). DMRIE-C-mediated RNA and DNA lipofection showed a somewhat similar outcome in terms of efficiency and viability although optimal lipid:nucleic acid ratio (4:1 versus 3:1) as well as incubation time (2 h versus 6 h) varied for RNA and DNA lipofection, respectively (Table 1).

Figure 1B:
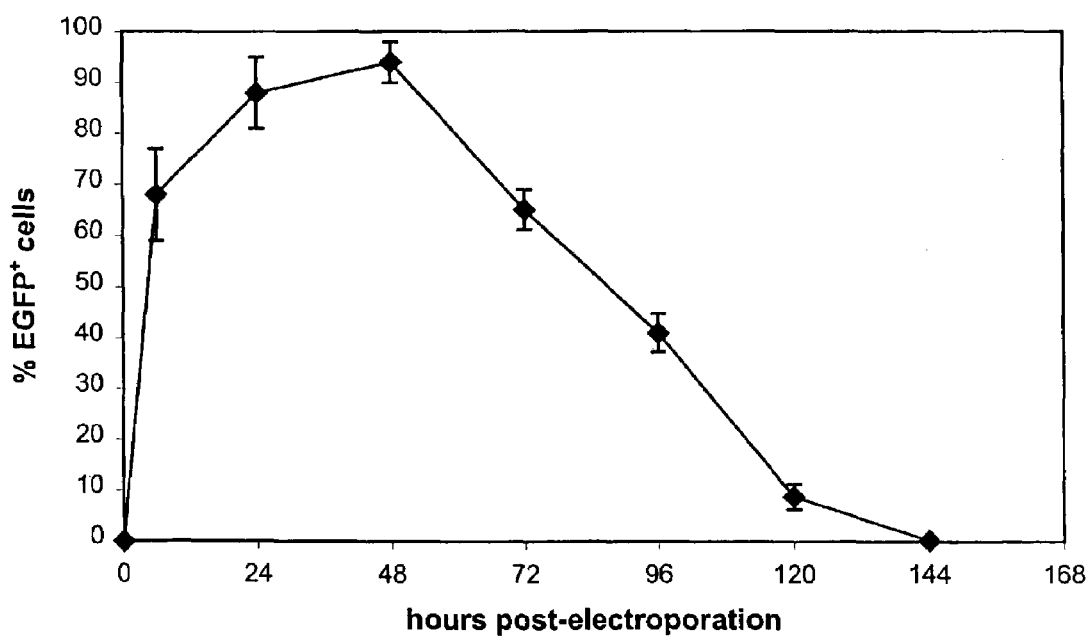

As RNA is extremely labile and has a short half-life time compared to DNA, we also studied kinetics of EGFP expression following mRNA electroporation (FIG. 1B). Transgene expression in K562 cells peaked at 24-48 h and rapidly declined to background levels after 6 days.

Figure 2A:
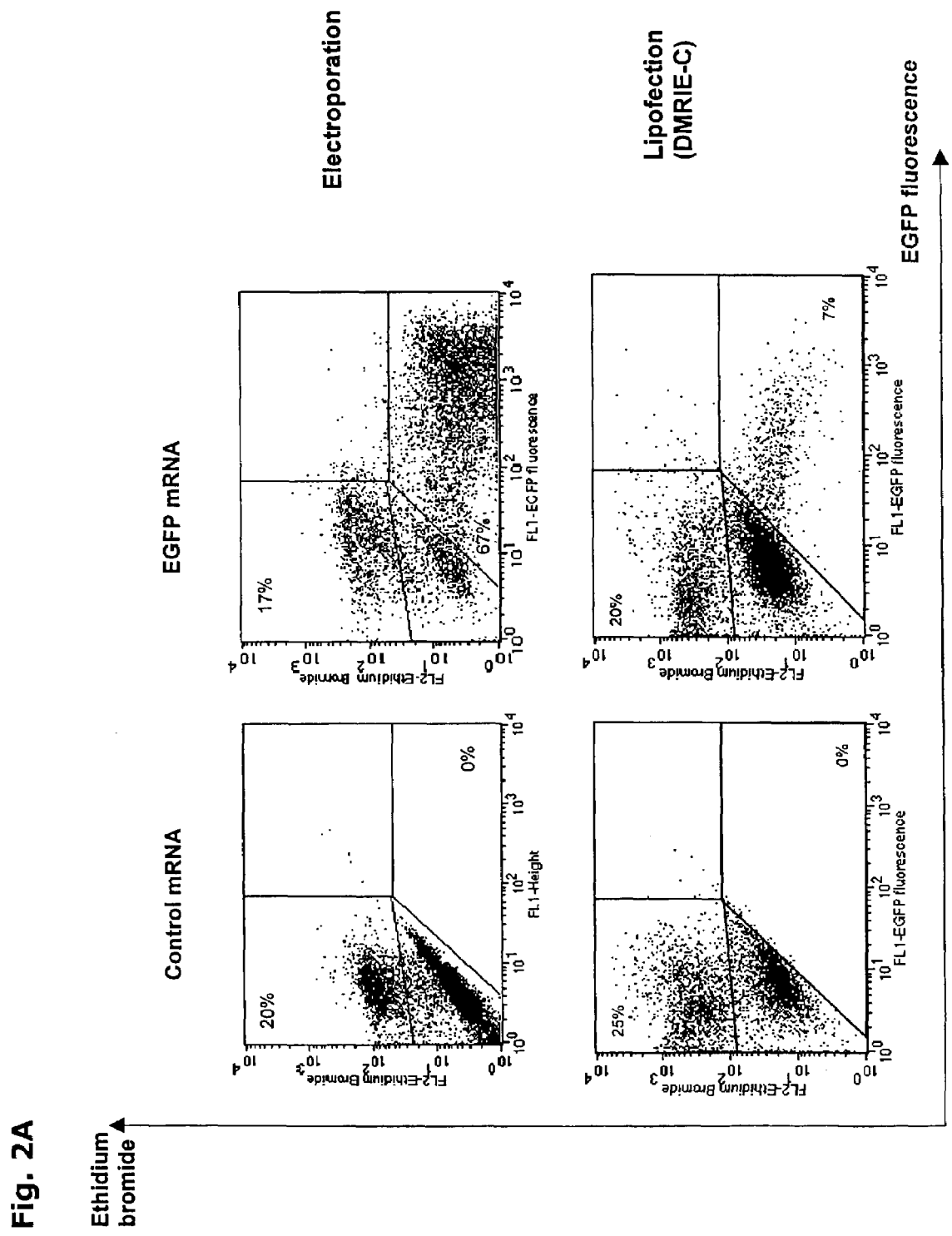
Figure 2B:
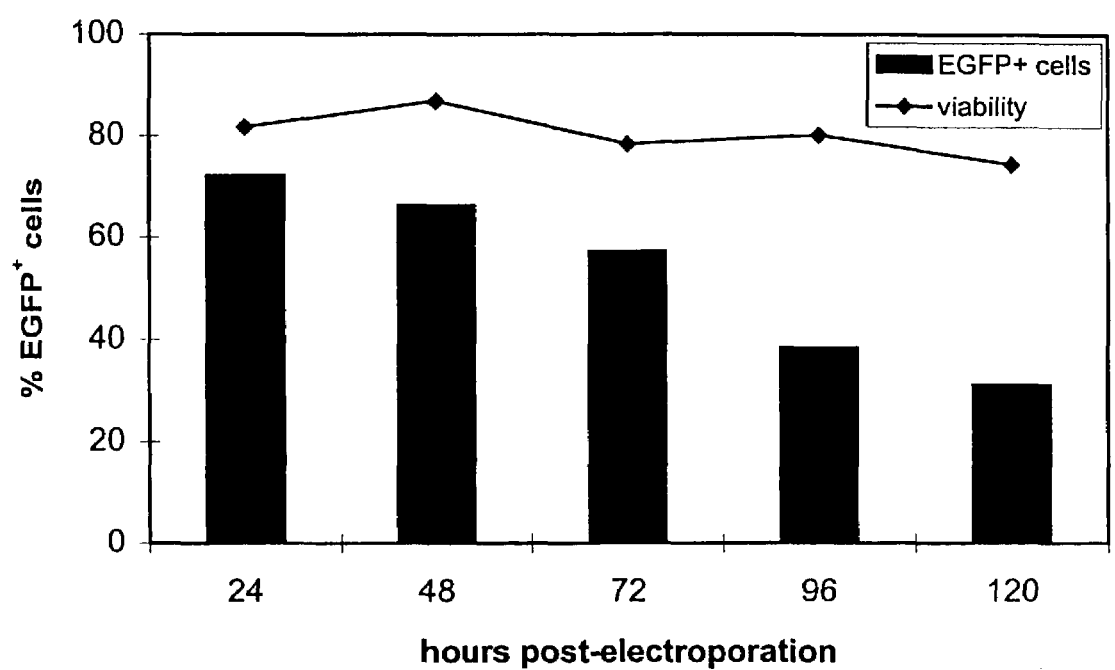
Figure 2C:
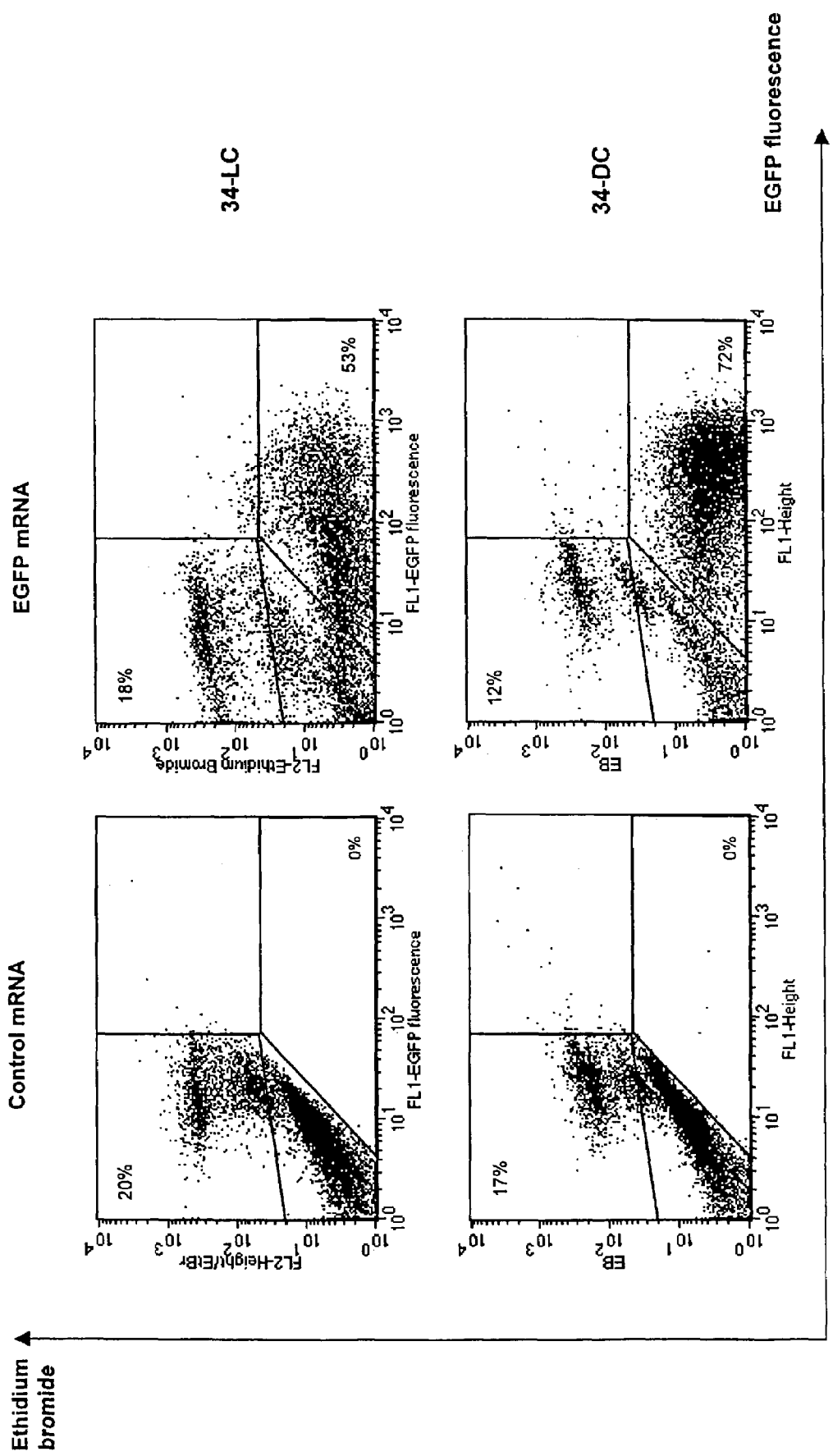

B. Efficiency of IVT mRNA transfection in different types of DC: Immature Mo-DC (iMo-DC) were generated from adherent PBMC in the presence of GM-CSF and IL-4. At day 5-6 of culture, Mo-DC were electroporated with EGFP mRNA. Optimization experiments revealed optimal settings similar to those of K562 cells (300 V, 150 µF), leading to maximal transfection efficiency combined with the lowest level of cell death. FCM analysis of EGFP expression showed more than 60% EGFP-expressing iMo-DC (FIG. 2A & Table 2). Mortality in Mo-DC after mRNA electroporation ranged from 15-30% (mean cell mortality rate 22±8%), although untransfected Mo-DC cultures already exhibited some degree of cell death (5-10%). When gating on the viable population, 85% of viable Mo-DC expressed EGFP to. some extent. TNFα+LPS-induced maturation of Mo-DC prior to transfection showed a significant decrease in electroporation and lipofection efficiency (Table 2). DC maturation following mRNA transfection had no effect on transgene expression (data not shown). Lipofection of EGFP mRNA in Mo-DC resulted in a much lower efficiency (7.5±0.5%) and was slightly more toxic (mean cell mortality rate 28±10%) to the cells than mRNA electroporation, as shown in FIG. 2A. Passive pulsing of DC with mRNA did not result in any detectable EGFP expression. Kinetic analysis of mRNA expression in Mo-DC showed a maximum 24 h after electroporation, followed by a slow decline in function of time (FIG. 2B). Five days after mRNA electroporation, EGFP was still detectable in a substantial proportion of Mo-DC (31% EGFP$^+$ cells), in contrast to transgene expression kinetics in K562 cells (9% EGFP$^+$ cells after 5 days). Monitoring of cell viability after mRNA electroporation revealed a somewhat stable viability in function of time (FIG. 2B).

mRNA transfection in bone marrow CD34$^+$ progenitor-derived DC (34-DC) and CD34$^+$ progenitor-derived Langerhans cells (34-LC) was also tested. Up to 72% and 53%, respectively, of these DC types were readily transfected by mRNA electroporation (FIG. 2C), but not by mRNA lipofection or mRNA pulsing (Table 2). Viability was always higher than 80% for both 34-DC and 34-LC (FIG. 2C). Table 2 summarizes efficiency of mRNA-based electroporation, lipofection and passive pulsing in the different types of DC.

TABLE 2

Efficiency of mRNA transfection in different types of DC

| Method of transfection | Transfection efficiency (%) | | | |
|---|---|---|---|---|
| | iMo-DC | mMo-DC | 34-LC | 34-DC |
| Electroporation | 63 ± 9 | 33 ± 8 | 50 ± 3 | 73 ± 3 |
| Lipofection | 7.5 ± 2.5 | 4 ± 2.3 | <BG | <BG |
| Passive pulsing | <BG | <BG | <BG | <BG |

Different types of DC were transfected with IVT EGFP mRNA using electroporation, lipofection or passive pulsing. One day after transfection, EGFP expression was analyzed by FCM to estimate transfection efficiency (% EGFP$^+$ DC). iMo-DC, immature Mo-DC; mMo-DC, mature Mo-DC; 34-LC, CD34$^+$ progenitor-derived Langerhans cells; 34-DC, CD34$^+$ progenitor-derived dendritic cells. Results are the mean±standard deviation (SD) of at least three independent experiments for passive pulsing, lipofection or electroporation; <BG, EGFP expression below background fluorescence.

Phenotype and maturation of mRNA-electroporated DC: Since DC have a delicate phenotype which can easily be disturbed by culture or transfection conditions, we assessed by FCM analysis whether electroporated DC retained their respective phenotype as well as their capacity to differentiate into mature DC. Control and EGFP mRNA-transfected Mo-DC were stained using monoclonal antibodies binding to characteristic DC markers including CD1a, HLA-DR, CD80, CD86 and CD83. Electroporation of mRNA showed no effect on the phenotype of Mo-DC, as electroporated Mo-DC co-expressing EGFP retained high levels of CD1a, HLA-DR and CD86 (FIG. 3A). Mock electroporation (electroporation without mRNA) gave similar results (data not shown). The capacity of mRNA-electroporated Mo-DC to differentiate to mature Mo-DC was evaluated by expression of mature DC markers including CD80 and CD83. FIG. 3B shows that mRNA electroporation itself did not induce DC maturation, but that the maturation potential after electroporation was retained since mRNA-transfected immature Mo-DC were able to upregulate CD83 and CD80 in the presence of a maturation cocktail (TNF-α+LPS).

Also, the phenotype of 34-DC was also not affected by mRNA electroporation (FIG. 3C). EGFP$^+$ 34-DC co-expressed HLA-DR, CD1a, CD80 and CD86. Similar findings were observed in 34-LC, with the exception that 34-LC exhibited lower levels of CD80 and CD86, compatible with their similarity to immature Langerhans-like DC (data not shown).

C. MHC class I-restricted antigen presentation by mRNA-transfected DC: Given the high transfection efficiency in Mo-DC, we investigated to what extent mRNA-transfected Mo-DC could process antigen and present MHC class I-restricted antigenic epitopes to an antigen-specific CTL clone. Therefore, we introduced mRNA encoding Melan-A/MART-1 into HLA-A2$^+$ Mo-DC using electroporation, lipofection or passive pulsing. Mo-DC electroporated or lipofected with Melan-A mRNA markedly stimulated an HLA-A2$^+$ Melan-A-specific CTL clone, as judged by IFN-γ secretion (FIG. 4). Mo-DC passively pulsed with Melan-A mRNA did not result in any CTL stimulation. HLA-A2$^+$ Mo-DC electroporated with EGFP mRNA or HLA-A2$^-$ Mo-DC electroporated with Melan-A mRNA did not stimulate the CTL clone to produce IFN-γ. Both HLA-A2$^+$ Melan-A$^+$ SK23-MEL melanoma cells and HLA-A2$^+$ Mo-DC, pulsed with the immunodominant Melan-A$_{27-35}$ peptide AAGIGILTV, were used as positive controls and induced strong IFN-γ production by the CTL clone. HLA-A2$^+$ Mo-DC pulsed with the M1 influenza peptide did not elicit any specific IFN-γ production. Mo-DC electroporated with Melan-A IVT mRNA stimulated the CTL clone more than twice stronger than mRNA-lipofected Mo-DC (FIG. 4), suggesting a correlation with the difference in transfection efficiency between the two gene transfer methods (Table 2). The observation that transfection efficiency and CTL activation were correlated, was also made when comparing efficiency of mRNA electroporation (Table 2) and the capacity to stimulate the CTL clone in the other types of DC (Table 3). Electroporation of HLA-A2$^+$ 34-DC and 34-LC with Melan mRNA, but not EGFP mRNA, led to specific CTL activation. In concordance with the absence of any detectable transfection level (Table 2), lipofection of 34-DC and 34-LC or passive pulsing of all types of DC with Melan-A mRNA did not result in any IFN-γ detectable above background levels (Table 3).

TABLE 3

CTL activation by different types of DC

| Method of transfection | CTL activation (IU IFN-γ/ml/24 h) | | | |
|---|---|---|---|---|
| | iMo-DC | mMo-DC | 34-LC | 34-DC |
| Electroporation | 11.3 ± 2.2 | 5.8 ± 1.8 | 6.9 ± 1.4 | 7.7 ± 3 |
| Lipofection | 3.7 ± 1.1 | 1.5 ± 0.8 | <BG | <BG |
| Passive pulsing | <BG | <BG | <BG | <BG |

Different types of DC were transfected with IVT Melan mRNA using electroporation, lipofection or passive pulsing. One day after transfection, 10$^5$ transfected DC were cocultured for 24 h with 10$^5$ Melan-A-specific CTL at 37° C. Afterwards, supernatants were collected and IFN-γ secretion was checked by IFN-γ ELISA, as described in the Materials and Methods section. Results are the mean±SD of at least five independent experiments for electroporation and of 3 independent experiments for passive pulsing and lipofection. iMo-DC, immature Mo-DC; mMo-DC, mature Mo-DC; 34-LC, CD34$^+$ progenitor-derived Langerhans cells; 34-DC, CD34$^+$ progenitor-derived DC; <BG, IFN-γ production below background.

D. Effect of maturation on mRNA loading in Mo-DC: Mo-DC obtained by culturing PBMC in the presence of GM-CSF and IL-4 for 5-7 days exhibit predominantly an immature phenotype (Romani, N. et al., J. Immunol. Methods, 196:137-151 (1996)). These immature Mo-DC are specialized in capturing large amounts of antigens from the environment (Sallusto, F., Lanzavecchia, A., J. Exp. Med., 179:1109-1118 (1994)). However, for optimal presentation to CTL, Mo-DC need to undergo a maturation process which can be induced by bacterial products (e.g. LPS), inflammatory cytokines (e.g. TNF-α) and/or CD40 ligation by T helper cells (Bancherau, J., Steinmann, R. N., Nature, 392:245-252 (1998)). Therefore, in order to test whether maturation and the sequence of loading affected the antigen-presenting capacity of Mo-DC, we evaluated the ability of Mo-DC loaded with Melan-A by mRNA electroporation to stimulate the CTL clone prior to and after maturation with LPS+TNF-α. FIG. 5 clearly indicates that the most potent CTL activation was obtained when mRNA loading by electroporation or lipofection was performed prior to maturation of Mo-DC. When maturation occurred prior to mRNA loading, there was a significant decrease in IFN-γ secretion by TIL cells (FIG. 5), likely to be correlated with the lower degree of transfectability of mature Mo-DC which were matured with LPS and TNF-α (Table 2).

E. cDNA loading versus mRNA loading: In contrast to Mo-DC, 34-LC and 34-DC can also be transfected by plasmid DNA electroporation (Van Tendeloo, V. F. I. et al., Gene Ther., 5:700-707 (1998)). Therefore, we evaluated whether plasmid DNA-transfected DC can also induce antigen-specific CTL activation. HLA-A2$^+$ 34-LC electroporated with plasmid DNA or IVT mRNA encoding Melan-A were incubated with the Melan-A specific CTL to evaluate IFN-γ secretion (FIG. 6). Strikingly, we reproducibly obtained similar IFN-γ levels with Melan-A cDNA- as with control vector-transfected 34-LC, indicating nonspecific CTL stimulation. Transfection with two other irrelevant plasmids (pEGFP-N1 and pCMV-Luciferase) resulted in a similar nonspecific CTL stimulation. This phenomenon was never observed in mock-transfected (electroporation without plasmid DNA) 34-LC or when the DNA was digested by DNase I prior to electroporation (FIG. 6). Similar observations were made in 34-DC (data not shown).

Example 2

EGFP RNA-transfection of immature monocyte-derived dendritic cells (generated from leukapheresis products and matured by a cocktail of IL-1β+IL-6+TNFα+PEG$_2$ under GMP conditions for clinical application) by electroporation. Monocyte-derived immature Dendritic Cells (DC) were generated from leukapheresis products as described (Feuerstein, B. et al., J. Immunol. Methods 245: 15-29 (2000)). Immature DC (d6) were washed twice in RPMI and once in washing-solution of the Optimix®-Kit (EQUIBIO, Maidstone Kent, U.K.). DC were adjusted to a final cell concentration of 10×10$^6$/ml in Optimix®-Medium. Then 0.2 ml of the cell suspension were mixed with 20 µg in vitro transcribed EGFP RNA in a 1.5 ml reaction tube. After incubation at room temperature for a maximum of 3 minutes the cell suspension were transferred in a 0.4-cm-gap electroporation-cuvette. Pulse were triggered at a voltage of 300 V and a capacitance of 150 µF with the Gene Pulser II (BioRad, Munich, Germany) resulting in pulse time of 7-10 msec. Immediately after that the cell suspensions were transferred to 6-well-plates (1×10$^6$ DC/well/3 ml culture medium supplemented with GM-CSF and IL-4). In the half number of the wells terminal maturation was induced by addition of IL-1β, IL-6, TNF-α and PGE$_2$ as described (Feuerstein, B. et al., J. Immunol. Methods 245: 15-29 (2000)). 48 h after electroporation the DC were counterstained with the indicated mouse mAbs and PE-conjugated anti-mouse Ig followed by FACS-analysis. The results are summarised in FIG. 7.

The addition of a maturation cocktail after transfection leads to a population of Dendritic Cells that is more mature as indicated by expression of CD83 and CD25 by a much higher percentage of DC. This is important as only mature DC induce immunity in vivo while immature ones can induce tolerance (Roncarolo, M. G. et al., Exp. Med. 15; 193(2):F5-9. Review. (2001)).

Monocyte-derived immature Dendritic Cells (DC) were processed as described above, and following addition of the maturation stimulus the longevity of EGFP expression in mature transfected DC was examined. Expression of EGFP is maintained in the majority of cells even after 4 days. The results are summarised in FIG. 8.

Example 3

EGFP RNA-transfection of Monocyte-derived Dendritic Cells by Electroporation—Titration of Voltage A: Influence of Voltage on Cell Size and Granularity Monocyte-derived immature Dendritic Cells (DC) were generated from leukapheresis products as described (Feuerstein, B. et al., J. Immunol. Methods 245: 15-29 (2000)). Immature DC (d6) were washed twice in RPMI and once in washing-solution of the Optimix®-Kit (EQUIBIO, Maidstone Kent, U.K.). DC were adjusted to a final cell concentration of 10×10$^6$/ml in Optimix®-Medium. Then 0.2 ml of the cell suspension were mixed with or without 20 µg in vitro transcribed EGFP RNA in a 1.5 ml reaction tube. After incubation at room temperature for a maximum of 3 minutes the cell suspension were transferred in a 0.4-cm-gap electroporation-cuvette. Pulse were triggered at the indicated voltage and a capacitance of 150 µF with the Gene Pulser II (BioRad, Munich, Germany) resulting in pulse time of 7-10 ms. Immediately after that the cell suspensions were transferred to 6-well-plates (1×10$^6$ DC/well/3 ml culture medium). Terminal maturation was induced by addition of IL-1β, IL-6, TNF-a and PGE$_2$ as described (Feuerstein, B. et al., J. Immunol. Methods 245: 15-29 (2000)). 48 h after electroporation the DC were analyzed. The contour-plots of FIG. 9A show on the x-axis the forward side scatter and on y-axis the sideward scatter.

The Forward and Side Scatter analysis addition reveals that for monocyte-derived Dendritic Cells that are generated from leukapheresis products, RNA-transfected by electroporation, and fully matured by adding a maturation cocktail consisting of of IL-1β, IL-6, TNF-a and PGE$_2$ (Feuerstein, B. et al., J. Immunol. Methods, 245: 15-29 (2000)) the use of 260 V is slightly better as the integrity of the cells is somewhat better preserved.

B: Influence of Voltage on CD83 and CD25

Figure 9B:
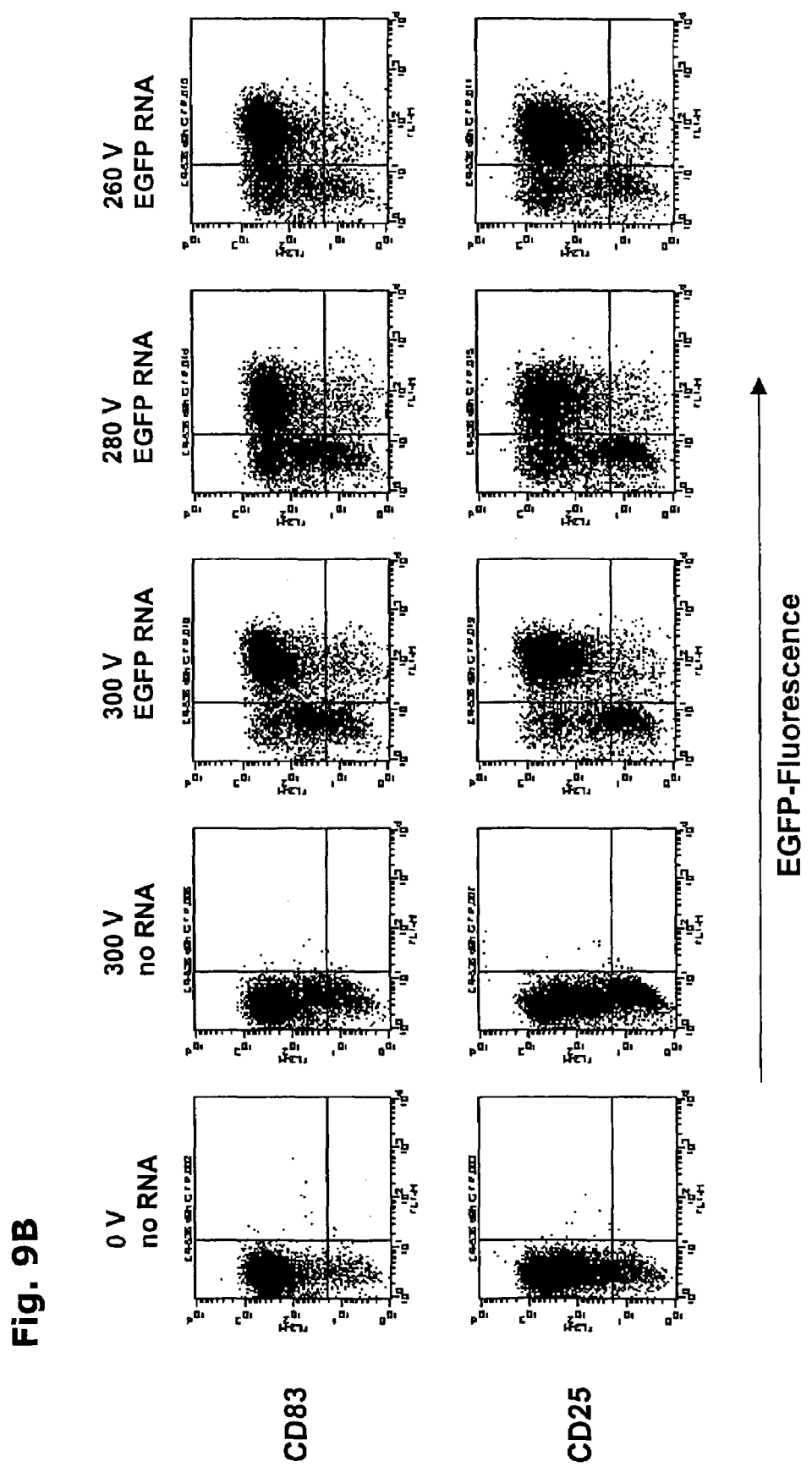

Immature DC (d6)—see FIG. 9A—were washed twice in RPMI and once in washing-solution of the Optimix®-Kit (EQUIBIO, Maidstone Kent, U.K.). DC were adjusted to a final cell concentration of 10×10$^6$/ml in Optimix®-Medium. Then 0.2 ml of the cell suspension were mixed with or without 20 µg in vitro transcribed EGFP RNA in a 1.5 ml reaction tube. After incubation at room temperature for a maximum of 3 minutes the cell suspension was transferred in a 0.4-cm-gap electroporation-cuvette. Pulses were triggered at the indicated voltage and a capacitance of 150 µF with the Gene Pulser II (BioRad, Munich, Germany) resulting in pulse time of 7-10 msec. Immediately after that the cell suspensions were transferred to 6-well-plates (1×10$^6$ DC/well/3 ml culture medium). Terminal maturation was induced by addition of IL-1β, IL-6, TNF-a and PGE$_2$. 48 h after electroporation the DC were counterstained with the indicated mouse mAbs and PE-conjugated anti-mouse Ig followed by FACS-analysis. The results are shown in FIG. 9B.

The phenotypic analysis reveals that for monocyte-derived Dendritic Cells that are generated from leukapheresis products, RNA-transfected by electroporation, and fully matured by adding a maturation cocktail consisting of of IL-1β, IL-6, TNF-a and PGE$_2$ (Feuerstein, B. et al., J. Immunol. Methods, 245: 15-29 (2000)) the use of 260 V is slightly better as more cells are in the upper right quadrant, i.e. expressing both EGFP and the maturation markers CD83 and CD25.

Example 4

EGFP RNA-transfection of already matured monocyte-derived dendritic cells (generated from leukapheresis cells and matured by a cocktail of IL-1β+IL-6+TNFα+PGE$_2$ under GMP conditions for clinical application) by electroporation.

A: Monocyte-derived immature Dendritic Cells (DC) were generated from leukapheresis products as described (Feuerstein, B. et al., J. Immunol. Methods, 245:15-29 (2000)). Immature DC (d6) were induced to undergo terminal maturation by addition of IL-1β, IL-6, TNF-β and PGE$_2$ as described in Feuerstein, B. et al., J. Immunol. Methods 245: 15-29 (2000). Mature DC were transfected with EGFP-RNA by electroporation as described in Example 2.

Figure 10A:
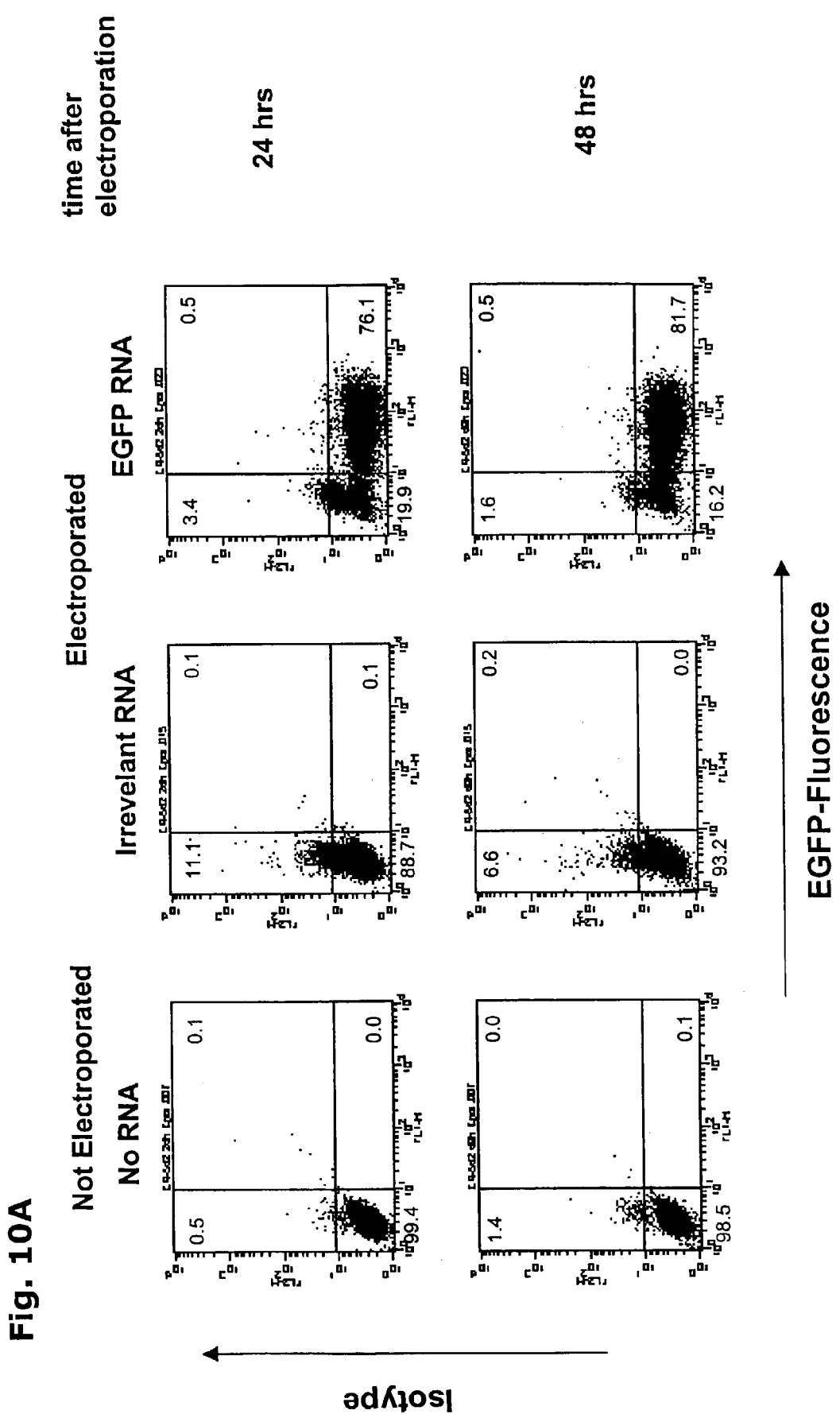
Figure 10B:
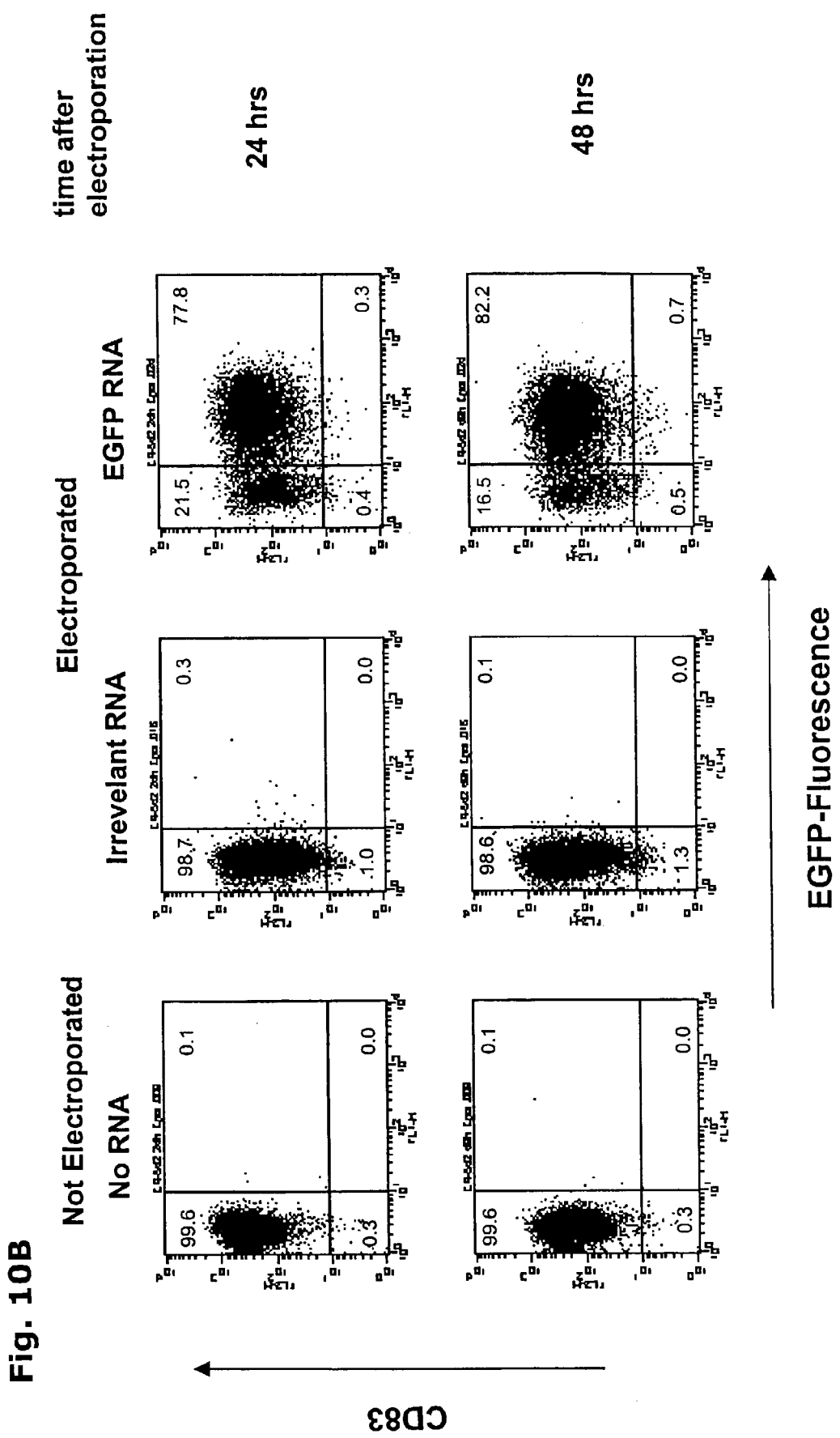
Figure 10D:
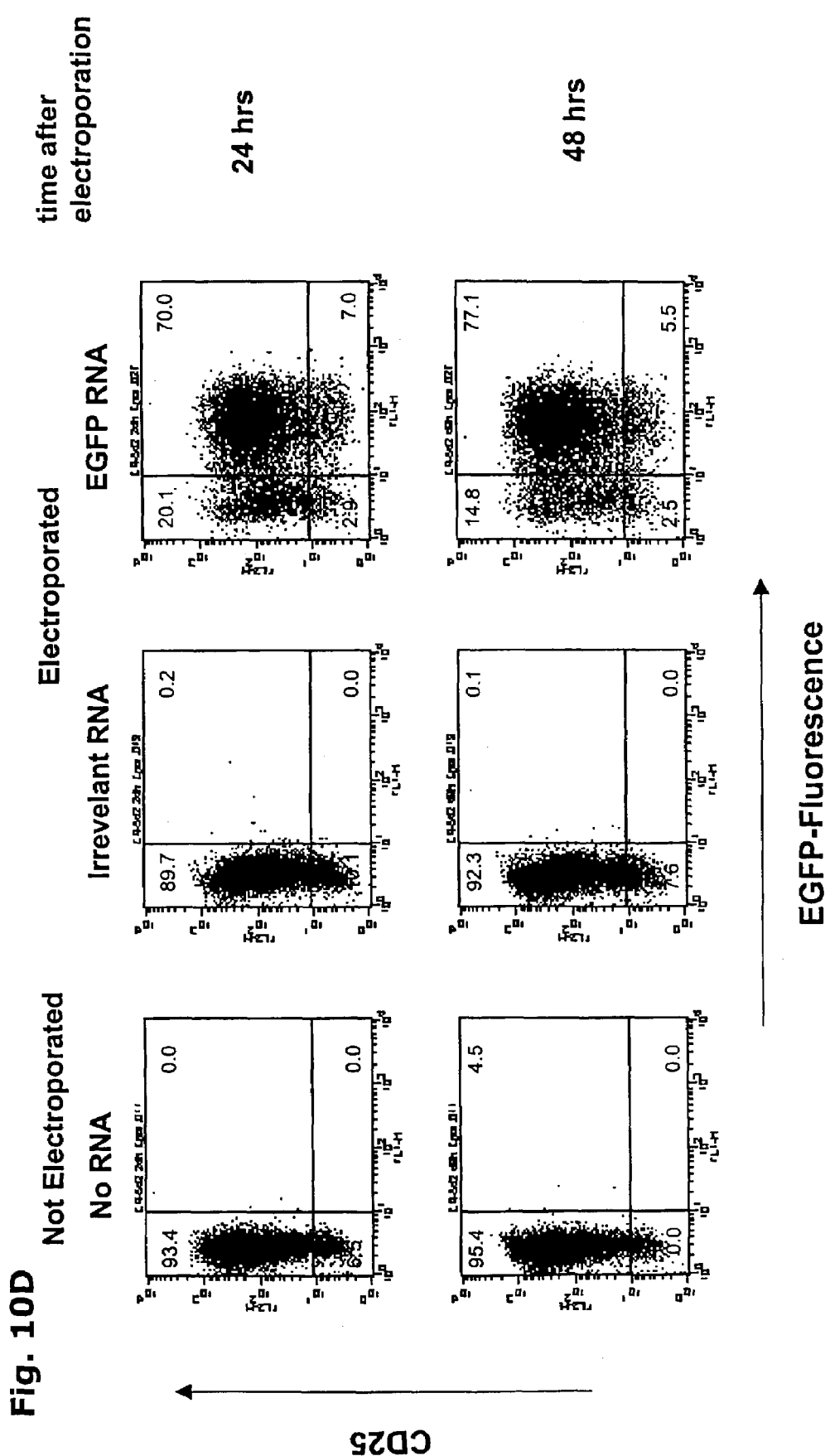
Figure 10E:
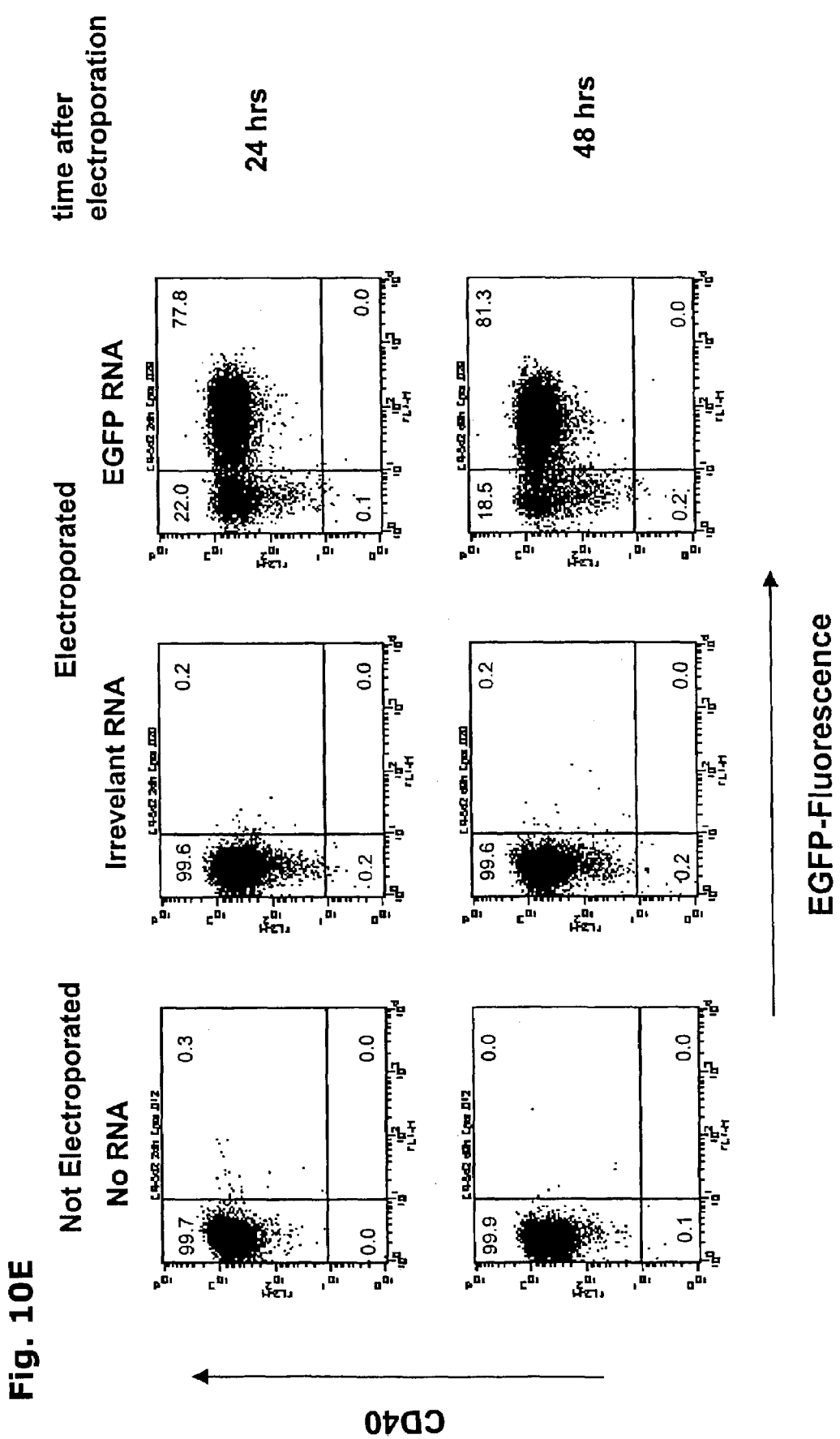
Figure 10G:
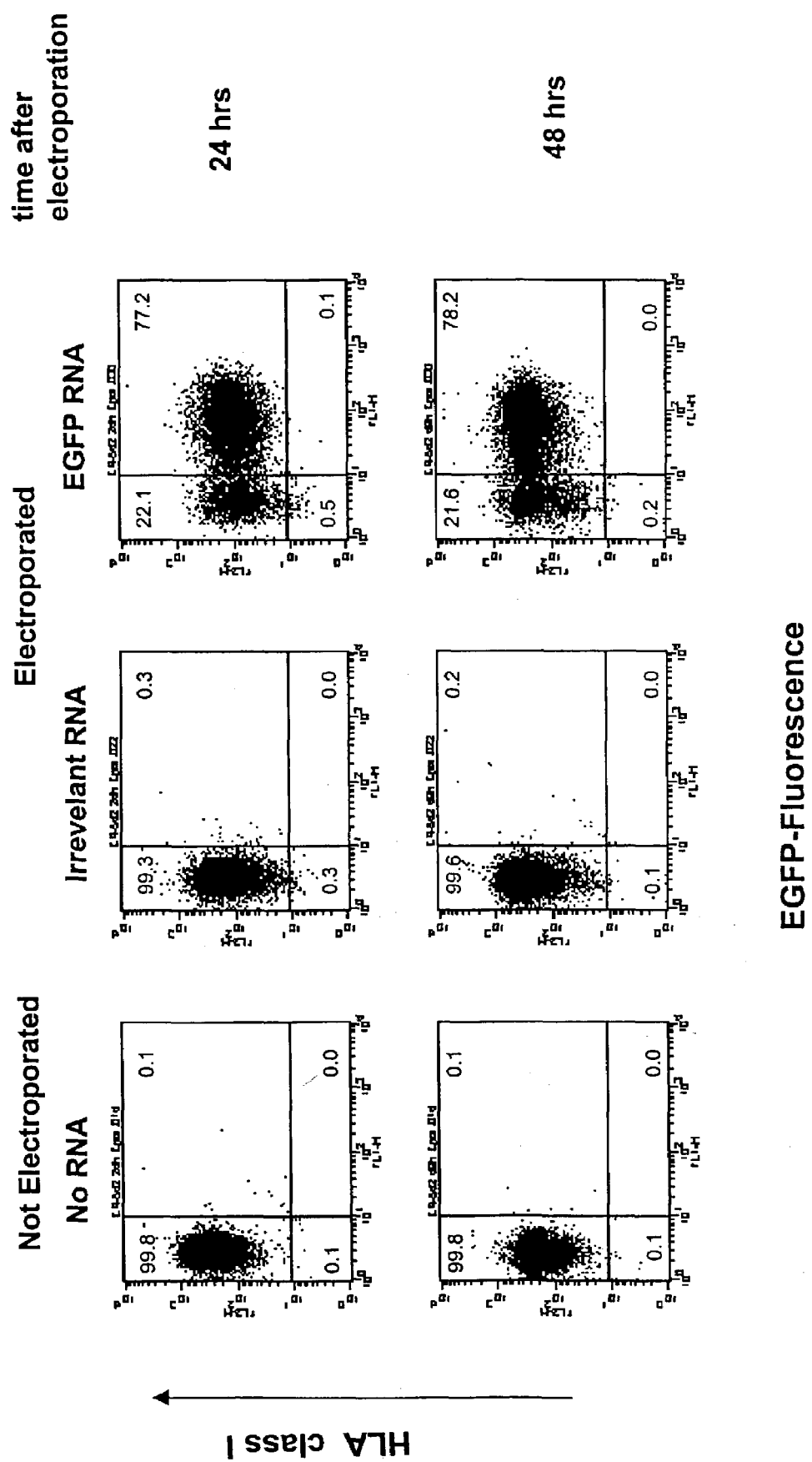
Figure 10H:
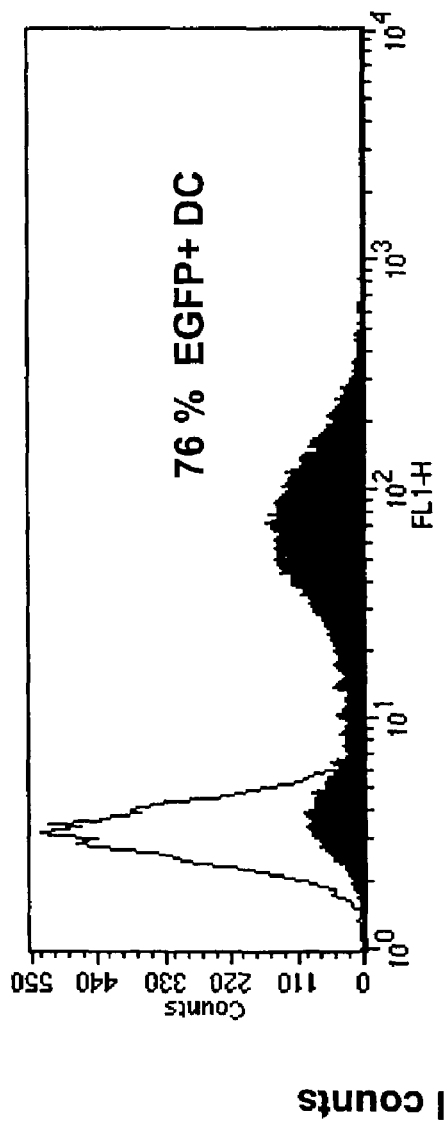
Figure 10H:
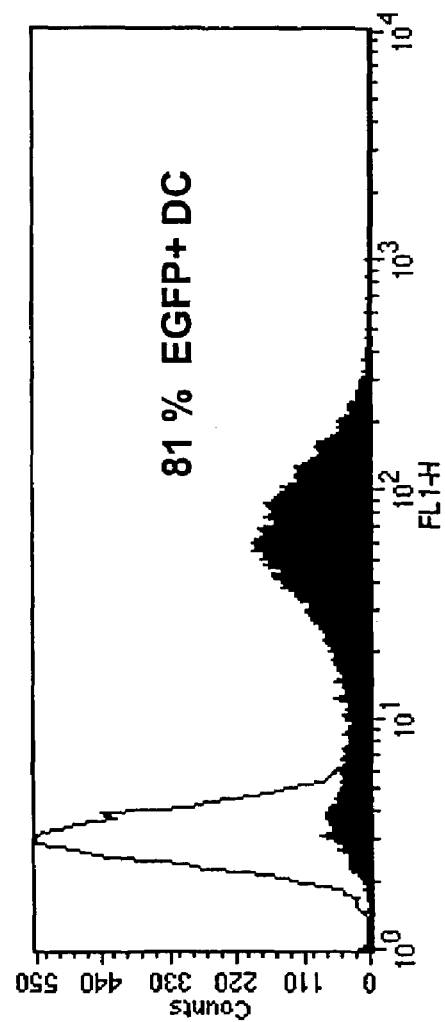

While DC matured by TNFα+LPS are transfected only to a mean of 33%, from the results depicted in FIGS. 10A and H it can be concluded that mature monocyte-derived Dendritic Cells (matured by an optimised maturation cocktail consisting of IL-1β+IL-6+TNFα+PGE$_2$) are efficiently transfected, and maintain EGFP expression over the 48 h time period tested.

B: Mature monocyte-derived Dendritic Cells (DC) are efficiently transfected, and maintain their mature phenotype (high expression of CD83, CD80, CD25, CD40, HLA-DR and MHC class I) over the 48 h time period tested as it is confirmed by FIGS. 10B-G.

The addition of a maturation cocktail after transfection leads to a population of Dendritic Cells that is more mature as indicated by expression of CD83 and CD25 by a much higher percentage of DC. This is important as only mature DC induce immunity in vivo while immature ones can induce tolerance (Roncarolo, M. G et al., J. Exp. Med. 15; 193(2): F5-9. Review. (2000)).

Example 5 mRNA-electroporated mature dendritic cells retain transgene expression, phenotypical properties and stimulatory capacity after cryopreservation.

TABLE 4

Transgene expression in cryopreserved mRNA-electroporated K562 cells

| | % EGFP + cells | MFI EGFP + cells | % dead cells |
|---|---|---|---|
| Control: EGFP expression in mRNA-electroporated K562 cells (n = 2) | | | |
| 3 h after EP | 66 ± 1 | 109 ± 15 | 19 ± 2 |
| 24 h after EP | 72 ± 1 | 363 ± 62 | 17 ± 1 |
| 48 h after EP | 73 ± 9 | 319 ± 67 | 18 ± 8 |
| Protocol 1: K562 cells frozen 3 hours after mRNA electroporation (n = 3) | | | |
| 3 h after thawing | 60 ± 2 | 286 ± 11 | 31 ± 2 |
| 24 h after thawing | 73 ± 1 | 454 ± 19 | 18 ± 1 |
| 48 h after thawing | 80 ± 1 | 207 ± 2 | 11 ± 1 |
| Protocol 2: K562 cells frozen 24 hours after mRNA electroporation (n = 3) | | | |
| 3 h after thawing | 72 ± 1 | 363 ± 62 | 22 ± 1 |
| 24 h after thawing | 77 ± 1 | 178 ± 43 | 13 ± 2 |
| 48 h after thawing | 80 ± 1 | 97 ± 43 | 7 ± 1 |

K562 cells were electroporated with EGFP mRNA and cryopreserved 3 or 24 hours after transfection. For cryopreservation, K562 cells were resuspended in cryotubes (Nunc CryoTube Vials, Nalgene Nunc International, Denmark) at a concentration of 10×10$^6$ per ml in pure FCS. Next, the suspension was mixed on ice with an equal volume of FCS supplemented with 20% DMSO (Sigma, St. Louis, Mo., USA). Cell suspensions were slowly frozen (−1° C./min) to −80° C. by using a cryo freezing container (Nalgene Nunc International). Cells were frozen at −80° C. for more than 24 hours before use in further experiments. Cells were analyzed at different time points before and after cryopreservation by FCM for EGFP expression to estimate transfection efficiency (=% EGFP+ cells) and the mean fluorescence intensity of EGFP$^+$ cells (=MFI EGFP+ cells). The number of dead cells was determined by ethidium bromide staining (=% dead cells). Results are shown as mean±standard error.

There was slightly less cell survival in cultures frozen 3 hours after the electroporation as compared to cultures frozen 24 hours after electroporation (p=0.0025). Cells need to recover for a short time after the electroporation.

Electroporated mRNA was still functional after cryopreservation. In cultures that had been frozen 3 hours after the electroporation, the MFI of expressed EGFP almost doubled between 3 and 24 hours after thawing (p=0.0009).

TABLE 5

Transgene expression in cryopreserved mRNA-electroporated DC

| | % EGFP + cells | MFI EGFP + cells | % dead cells |
|---|---|---|---|
| Control 1: EGFP expression in mRNA-electroporated iMo-DC (n = 3) | | | |
| 24 h after EP | 73 ± 5 | 246 ± 63 | 12 ± 3 |
| 48 h after EP | 59 ± 10 | 218 ± 57 | 24 ± 9 |
| Cryopreservation: iMo-DC cells frozen 18 h after mRNA electroporation (n = 4) | | | |
| 6 h after thawing | 61 ± 2 | 215 ± 14 | 26 ± 1 |
| 24 after thawing | 27 ± 1 | 251 ± 24 | 64 ± 2 |
| Control 2: EGFP expression in mRNA-electroporated iMo-DC + maturation (n = 3) | | | |
| 24 h after EP | 71 ± 3 | 431 ± 60 | 13 ± 1 |
| 48 h after EP | 73 ± 3 | 428 ± 64 | 11 ± 1 |
| Cryopreservation: mMo-DC cells frozen 24 h after mRNA electroporation (n = 4) | | | |
| 6 after thawing | 63 ± 1 | 464 ± 24 | 20 ± 1 |
| 24 after thawing | 60 ± 1 | 390 ± 19 | 25 ± 2 |

Immature Mo-DC were electroporated with EGFP mRNA. Cells were cryopreserved as immature DC 18 hours after transfection or as mature DC 24 hours after transfection. Maturation was induced by adding a maturation cocktail (TNF-α+PGE$_2$+IL-1+IL-6) directly after transfection. Cells were analyzed by FCM at different time points before and after cryopreservation for EGFP expression, in order to estimate transfection efficiency (=% EGFP+ cells) and the mean fluorescence intensity of EGFP+ cells (=MFI EGFP+ cells). The number of dead cells was determined by ethidium bromide staining (=% dead cells). Results are shown as mean±standard error. EP, electroporation.

As seen in a non-frozen control of immature and mature DC (Table 5, respectively control 1 and control 2), viability is not significantly affected by this electroporation in function of time (p-value respectively 0.1849 and 0.1362) and cells express high levels of EGFP (Table 5; FIGS. 11A&B).

Immature DC that were frozen 18 hours after electroporation seemed to survive the freezing cycle well 6 hours after thawing. There was a small increase in cell mortality (+13%, p=0.0008), but the MFI of EGFP expressing cells was approximately the same as in non-frozen control DC (p=0.5185). However, 24 hours after thawing, there was high level of cell mortality in the frozen cultures as compared to non-frozen control DC that have been cultured for 48 hours after electroporation (64% versus 24%, p=0.0017) (Table 2; FIG. 11A).

For the cryopreservation of mature DC, immature Mo-DC were electroporated, followed by a 2 hour incubation in medium supplemented with GM-CSF and IL-4, in order to allow transgene expression to start. Following this, the DC maturation cocktail was added and the level of EGFP expression and cell survival was determined 24 and 48 hours after transfection. DC were frozen 24 hours after mRNA electroporation and transgene expression and cell survival was determined 6 and 24 hours after thawing (Table 2; FIG. 1B). Six hours after thawing, DC cultures appeared to survive the freezing and have a similar number of EGFP+ cells and MFI level of EGFP+ cells as compared to non-frozen cultures (p-value respectively 0.0033 and 0.5183). Mature DC survived the thawing procedure better than frozen immature DC (64% cell death for immature DC versus 25% for mature DC after 24 hours of culture, p=0.00004).

Example 6

A combination of a serum-free culture protocol and a poly-I:C maturation stimulus results in the rapid generation of fully mature and viable CD83+ DC from peripheral blood monocytes. This provides for an efficient and clinical applicable antigen loading strategy for these short-term cultured DC, based on mRNA electroporation of monocytes. The T-cell activation capacity of these short-term and serum-free cultured Mo-DC was found to be highly stimulatory in an influenza antigen model system using influenza matrix protein M1 peptide-pulsed and matrix protein mRNA-electroporated DC. In the following (including the corresponding Figures) results are expressed as mean±standard deviation. Comparisons were validated using Student's t-test. A p-value ≦0.05 was considered to be statistically significant.

A. Characterization of short-term and serum-free in vitro cultured DC, with or without poly-I:C maturation: After monocyte enrichment from PBMC, cells were cultured for 2 days in AIM-V medium supplemented with GM-CSF only. To obtain mature DC, poly-I:C was added after 24 hours of culture. Cultured cells were analyzed after a total culture period of 48 hours by flow cytometry. One observed difference with classical DC cultured for 6-7 days in serum-containing medium supplemented with GM-CSF and IL-4, was a lower forward- and side-scatter profile of the serum-free-cultured cells (FIG. 1, upper panels). However, this was not due to serum-free- or poly-I:C-induced mortality, since ethidium bromide staining showed cell populations with a mean viability of more than 80% (FIG. 14, lower panels). Immune phenotyping was also performed after 48 hours of culture (FIG. 15). A majority of the cultured cells showed downregulation of CD14 expression, demonstrating loss of a characteristic monocyte marker. This downregulation is most likely due to serum-free culture of monocytes, since in experimental conditions, where human AB serum (1%) was added to the DC culture medium, no downregulation of CD14 was observed (data not shown). Cells cultured without poly-I:C showed moderate expression of HLA-DR, and only a small fraction showed expression of CD83 and of the costimulatory molecules CD80 and CD86. This corresponds with a typical immature DC phenotype. In contrast, cells that were exposed to poly-I:C, showed a fast upregulation of HLA-DR, CD83, and the costimulatory molecules CD80 and CD86, corresponding with the typical phenotype of mature DC. CD1a was present on a small proportion of the cells (FIG. 15).

B. Poly-I:C maturated serum-free-cultured DC are more potent than their immature counterparts in inducing in vitro T-cell immune responses: In order to determine whether the new cultured cell types also had the functional properties of DC, their stimulatory capacity was first evaluated in a modified allogeneic mixed leucocyte reaction (MLR). For this, immature and mature DC were cultured for 7 days with allogeneic PBMC. Next, the stimulated PBMC were restimulated with PBMC from the DC donor, and IFN-γ secretion in the supernatant was analyzed by ELISA (FIG. 16). Based on the level of IFN-γ secretion against the PBMC targets, the results show that mature DC were more potent in inducing an allogeneic MLR response than immature DC (3.1±0.1 IU/ml/6 h for immature DC vs. 21.3±0.8 IU/ml/6 h for mature DC, p=0.0004). Autologous antigen-specific stimulatory capacity was evaluated in an influenza model system, DC were pulsed with an HLA-A2-restricted influenza matrix protein M1-specific peptide and cocultured with autologous PBMC. After 7 days of coculture, cultured PBMC were restimulated with M1 peptide- or E7 control peptide-pulsed T2 cells. After a 6-hour restimulation, IFN-γ secretion in the supernatant was analyzed by ELISA (FIGS. 17A and 17B). Based on the level of IFN-γ secretion against the influenza M1 target, the results show that mature DC were more potent in inducing an autologous immune response than immature DC (FIG. 17A: 2.3±0.3 IU/ml/6 h for immature DC vs. 22.9±3.1 IU/ml/6 h for mature DC, p=0.0006). The specificity of this immune response was shown by a significantly lower amount of IFN-γ production against the control HPV E7 target as compared to the influenza M1 target (FIG. 17A: for mature DC p=0.0079, for immature DC p=0.0461; FIG. 4B: for mature DC p=0.0064). In order to show that IFN-γ was produced by CD8+ T lymphocytes, we used an IFN-γ-secreting assay in which, after restimulation of cultured PBMC with an influenza (T2/M1) or control (T2/E7) target, IFN-γ-secreting cells are directly stained for detection by flow cytometry (FIG. 18). Flow cytometric analysis showed detectable M1-specific IFN-γ-secreting T-cells within the CD8+ T-cell population of PBMC cultures initially stimulated with mature DC pulsed with M1 peptide. This immune response was virtually not seen in cultures initially stimulated with immature DC.

C. mRNA electroporation of monocytes followed by differentiation to DC: Using a previously optimized mRNA electroporation protocol, we examined the possibility of genetic modification of the above-described DC. In these experiments, the EGFP reporter gene was used to assess mRNA transfection efficiency. After optimization, the following mRNA electroporation and culture protocol resulted in the generation of antigen-loaded mature DC. First, monocytes were isolated from PBMC by CD14 immunobead magnetic separation. After electroporation, cells were resuspended in serum-free AIM-V medium supplemented with GM-CSF. After 24 hours of culture, poly-I:C was added to the cultures to obtain mature DC. The cultured DC were analyzed 48 hours after electroporation of the monocytes. No difference was observed in scatter profile between non-electroporated and EGFP mRNA-electroporated monocytes that were cultured to DC (FIG. 19A). The mean electroporation-related mortality in the DC cultures was 10% (mean of 3 independent experiments, FIG. 19B). This low cell mortality was most probably due to the serum-free culture condition, because addition of autologous plasma following electroporation resulted in lack of electroporation-related mortality (data not shown). Comparing the level of EGFP fluorescense in non-electroporated and EGFP mRNA-electroporated short-term cultured DC, the data show low, but detectable, EGFP expression in practically all of the viable mRNA-loaded DC (FIG.

19C). The phenotype of the cultured cells was examined by flow cytometry for the characteristic DC markers (FIG. 20). We observed no difference in phenotype between non-electroporated and EGFP mRNA-electroporated short-term and serum-free cultured mature DC. Remarkable, as compared to the data shown in FIG. 15, in which DC were cultured from adherent monocytes, less downregulation of CD14 was observed on DC grown from CD14$^+$ positively isolated monocytes (<10% CD14$^+$ DC generated from adherent PBMC versus around 50% CD14$^+$ DC generated from CD14$^+$ monocytes).

D. Stimulatory capacity of mRNA-loaded short-term-cultured mature DC: We examined in an influenza model system whether mRNA-electroporated monocytes rapidly differentiated in serum-free medium into mature DC could stimulate antigen-specific T-cells upon coculture with PBMC. In these experiments, monocytes were electroporated with mRNA encoding influenza matrix protein M1, and further cultured to mature DC as described above. Next, DC were cocultured with autologous PBMC without the addition of exogenous cytokines. After 7 days of culture, primed PBMC were restimulated with T2 cells pulsed with a MHC class I-restricted influenza matrix protein M1 peptide (T2/M1), and IFN-γ secretion was determined after 6 hours by ELISA (FIG. 21). Upon restimulation with peptide-pulsed T2 cells, the activated T cells in the primed PBMC culture produced IFN-γ against the immunodominant M1 matrix protein peptide. The specificity of this activation was shown by only background IFN-γ production of the primed PBMC culture against HPV E7 peptide-pulsed T2 cells (T2/M1 vs. T2/E7, for FIG. 8A: p=0.0002, for FIG. 8B: p<0.0001).

Discussion: In the first part of this study we describe an alternative culture protocol for Mo-DC. The present serum-free culture and poly-I:C maturation protocol resulted in the rapid generation of fully mature, viable, and highly stimulatory CD83+ DC. The observed phenotypical properties (FIG. 15) are in accordance with previous reported data by Czerniecki et al. on similar DC culture protocols for short-term and serum-free-cultured DC (Czerniecki, B. J., et al. 2001. Diverse functional activity of CD83+ monocyte-derived dendritic cells and implications for cancer vaccines. *Crit. Rev. Immunol.* 21:157). The observed difference in CD14 down-regulation between DC cultured from adherent monocytes (FIG. 15, CD14+ cells less than 10%) and DC cultured from magnetic bead-isolated monocytes (FIG. 20, around 50% CD14$^+$ cells), could likely be ascribed to the CD14 selection procedure, and warrants further investigation, e.g. by comparing positive selections of CD14$^+$ cells and negative selection of CD14$^+$ cells by depletion of B-, T- and NK-cells. A similar observation was already reported by Cavanagh et al. where conventional DC, grown from adherent PBMC, were compared to DC generated from monocytes sorted by CD14 positive selection (Cavanagh, L. L. et al. 1998. Proleferation in monocyte-derived dendritic cell cultures is caused by progenitor cells capable of myeloid differentiation. *Blood.* 92:1598). The relatively rapid maturation of the presented short-term cultured DC, seen by the upregulation of HLA-DR, CD80, CD86 and CD83, as compared to immature DC is, according to previous reports, due to poly-I:C signaling via Toll-like receptor 3 (Alexopoulou, L. et al. 2001. Recognition of double-stranded RNA and activation of NF-κB by Toll-like receptor 3. *Nature* 413:732). This signaling pathway induces IFN-α production by the DC (Celia, M. et al. 1999. Maturation, activation, and protection of dendritic cells induced by double-stranded RNA. *J. Exp. Med.* 189:821), which can act as a strong maturation stimulus. Furthermore, type I interferons, like IFN-α, might induce IL-15 production and in this way strongly promote a T-helper 1 response, which is needed for induction of a strong CD8+ T cell response (Santini, S. M. et al. 2000. Type I interferon as a powerful adjuvant for monocyte-derived dendritic cell development and activity in vitro and in Hu-PBL-SCID mice. *J. Exp. Med.* 10:1777; Saikh, K. U., et al. 2001. IL-15-induced conversion of monocytes to mature dendritic cells. *Clin. Exp. Immunol.* 126:447). This might account for the differences we observed when comparing immature and mature short-term cultured DC in both allogeneic and autologous T-cell stimulatory capacity. These data also confirm recent experiments from Bhardwaj and colleagues, describing the need for mature DC to activate influenza-specific memory T-cells (Larsson, M. et al. 2000. Requirement of mature dendritic cells for efficient activation of influenza A-specific memory CD8+ T cells. *J. Immunol.* 165: 1182).

The second part of this study focused on the genetic modification of these short-term serum-free cultured DC. Previously, we developed an antigen loading strategy based on electroporation of mRNA into DC cultured in the presence of serum and GM-CSF+IL-4. This transfection technology resulted in high-level transgene expression in Mo-DC using an EGFP reporter gene. More than 70% of the transfected cells showed high level EGFP expression (relative fluorescence between $10^2$ and $10^3$ decade as measured by flow cytometry) and retained their phenotypical properties after transfection (Van Tendeloo, V. et al. 2001. Highly efficient gene delivery by mRNA electroporation in human hematopoietic cells: Superiority to lipofection and passive pulsing of mRNA and to electroporation of plasmid cDNA for tumor antigen loading of dendritic cells. *Blood.* 98:49; Ponsaerts, P. et al. 2002. mRNA-electroporated mature dendritic cells retain transgene expression, phenotypical properties and stimulatory capacity after cryopreservation. *Leukemia* (in press)). However, the use of this technology for transfection of short-term serum-free cultured DC, as presented in this study, resulted in substantial cell mortality among transfected cells (data not shown). Because a DC vaccine, in order to be effective, should have a high DC viability, we attempted to transfect fresh monocytes followed by rapid differentiation to DC. As shown by the data in FIG. 19, cell viability was high and antigen was still detectable in the DC two days after the initial electroporation in virtually all cells when using this strategy. Noteworthy, as compared to our previous results (Van Tendeloo, V. et al. 2001. Highly efficient gene delivery by mRNA electroporation in human hematopoietic cells: Superiority to lipofection and passive pulsing of mRNA and to electroporation of plasmid cDNA for tumor antigen loading of dendritic cells. *Blood.* 98:49; Ponsaerts, P. et al. 2002. mRNA-electroporated mature dendritic cells retain transgene expression, phenotypical properties and stimulatory capacity after cryopreservation. *Leukemia* (in press)), related to the electroporation of DC cultured in serum in the presence of GM-CSF and IL-4, the level of protein expression, e.g. EGFP, was much lower in monocytes after 24 hours (data not shown) and 48 hours (FIG. 19c). Monocytes that were electroporated with EGFP-mRNA and subsequently differentiated to mature DC showed only a small shift of EGFP fluorescence as compared to non-electroporated control DC. This can be explained by the difficulty of obtaining high protein expression levels in primary uncultured mononuclear cells (data not shown). However, there is no consensus yet that a high level of antigen expression in DC is mandatory for induction of a stronger immune response. Here, we provide functional evidence that, despite the lower level of antigen expression in these short-term-cultured DC, a specific immune response in an influenza model system could be initiated very efficiently. Previous experiments in our laboratory (Ponsaerts, P. et al. 2002. mRNA-electroporated mature dendritic cells retain transgene expression, phenotypical properties and stimulatory capacity after cryopreservation. *Leukemia* (in press)) focused on the stimulatory capacity of influenza matrix protein mRNA-electroporated conventional DC, i.e. DC cultured for 6-7 days in serum-containing medium supplemented with GM-CSF and IL-4, and maturated with a cocktail consisting of TNF-α, $PGE_2$, IL-1 and IL-6. Comparing the final outcome in terms of autologous influenza-specific T-cell activation, antigen mRNA-loaded conventional DC and short-term-cultured DC gave similar results, indicating the validity of this protocol.

In conclusion, this combined serum-free culture and poly-I:C maturation (and optional mRNA electroporation) of peripheral blood monocytes results in the rapid generation of fully mature, viable and highly stimulatory CD83+ DC. This ex vivo protocol results in an important reduction in time and consumables for preparation of mature DC as compared to classical culture protocols. This might be of importance not only for laboratory experiments, but also for clinical immunotherapy protocols.

Example 7 mRNA Electroporation of Adult Bone Marrow.
Total cells: 20 million NC
EP parameters: 300V, 1050 μF (mRNA settings) or 260V, 150 μF (DNA settings)

Cells were washed twice in IMDM, once in Electroporation Wash Buffer and resuspended in Optimix medium at 5 million cells/200 μl. 20 μg of EGFP mRNA was added to the cells just before electroporation. In case DNA settings were used, 300 μl of Optimix® was added to the cells (total volume 500 μl). After shocking, cells were immediately put into 3 ml of warm culture medium (IMDM, 10% FCS) supplemented with IL-3, IL-6 and stem cell factor. EGFP analysis at 24 h-96 h and phenotypic analysis at 96 h by FACS. The results are summarized in Table 6

TABLE 6

| Time-point | Settings | Viability | Efficiency |
|---|---|---|---|
| 24 h | 300 V, 150 μF | 98% | 25% |
| | 260 V, 1050 μF | 95% | 21% |
| 96 h | 300 V, 150 μF | ND | 31% |
| | 260 V, 1050 μF | ND | 22.6% |

ND, not done

This experiment shows that the mRNA electroporation technology of the present invention is able to transfect human bone marrow mononuclear cells up to 25-30% efficiency. High levels of EGFP expression were observed in the myeloid fraction (CD33+ cells), in particular in the monocyte fraction (CD14+ cells) and the hematopoietic progenitor fraction (CD34+ cells) comprising the hematopoietic stem cells. A low but consistent transfection level was observed in the lymphoid fraction (CD7+ and CD19+ cells), concordant with the data obtained in peripheral blood (see FIGS. 22A to E).

Example 8 mRNA Electroporation of Mouse Embryonic Stem Cells.
Total cells: 15 million ES cells
EP parameters: 300V, 150 μF (mRNA settings)

5 million ES cells were thawed on 10/6 and put into culture in gelatin-coated 75 $cm^2$ flask and 3 million mitomycin C-treated mouse embryonic fibroblasts (MEF) feeder cells for 48 h. Then, ES cells were trypsinized, washed 3 times in DMEM, once in Electroporation Wash Buffer and resuspended in Optimix medium at 7.5 million cells/200 μl. 20 μg of EGFP mRNA or 20 μl RNase-free water (mock) was added to the cells just before electroporation. After shocking, cells were immediately put into gelatin-coated $25cm^2$ flasks with or without 1 million MEF feeder cells into 8 ml ES cell medium (DMEM, 15% FBS, glutamine, sodium pyruvate, NEAA, β-ME and antibiotics). EGFP fluorescence was checked by fluorescence microscopy at 24 h post-EP and simultaneous EGFP and phenotypic analysis was performed at 48 h post-EP by FACS (results see FIGS. 23A and B).

By this experiment it is shown that the mRNA electroporation technology of the present invention is able to transfect mouse embryonic stem (ES) cells to levels above 90% efficiency, implicating a powerful tool to genetically modify mouse ES cells, and possibly also human ES cells, be it in a transient manner. This could be of value for control of differentiation of ES cells by transgene expression of master regulator genes, skewing or biasing differentiation into distinct lineages for large-scale generation of differentiated cells and tissues in vitro.

Example 9 mRNA Electroporation of Adult Peripheral Blood
Total cells: 10 million NC
EP parameters: 300V, 150 μF (mRNA settings)

Fresh PBMC were washed twice in IMDM, once in Electroporation Wash Buffer and resuspended in Optimix medium at 5 million cells/200 μl. 20 μg of EGFP mRNA or 20 μl RNase-free water (mock) was added to the cells just before electroporation. After shocking, cells were immediately put into 3 ml of warm culture medium (IMDM, 10% FCS). Simultaneous EGFP and phenotypic analysis was performed at 24 h by FACS (results see FIGS. 24A-C).

This experiment shows that the mRNA electroporation technology of the present invention is able to transfect human peripheral blood mononuclear cells up to 4% efficiency. The low but consistent transfection levels were mainly observed in the monocyte fraction (CD14+ cells) and to a lower extent in the T lymphocytes (CD3+ cells) and the natural killer (NK) cells. B cells (CD19+ cells) could not be transfected using the current electroporation parameters, which warrants further optimization for this type of cells.

Example 10

A. Electroporation of mRNA at μs-range (soft pulse; general method): Immature (d6) or mature (d7) Mo-DC were washed once with Opti-Mem® or with washing-solution Optimix®, respectively. Cells were adjusted to a final cell concentration of $1-4\times10^7$/ml in electroporation buffer (Opti-Mem®, Optimix® or isoosomolar electroporation buffer). Then 0.2-0.8 ml of the cell suspension were mixed with IVT mRNA (up to 20 μg /$2\times10^6$ cells) in a 1.5 ml reaction tube. After incubation at room temperature for a maximum of 3 minutes the cell suspension were transferred in a 0.4-cm-gap electroporation cuvette. Cells were triggered at a voltage of 400 and a pulse time of 500 µs using Multiporator® (Eppendorf, Hamburg, Germany) or ECM 830® (Genetronics BTX, San Diego, Calif., USA). Immediately after that the cell suspension were transferred to 6-well-plates (1×10⁶ DC/ well/ 3 ml culture medium supplemented with GM-CSF and IL-4). In the case of immature DC terminal maturation were induced by addition of IL-1β, IL-6, TNF-α and $PGE_2$. FCM-analysis were performed in the time range of 24-96 h. The general settings are summarized in Table 7.

TABLE 7

| | |
|---|---|
| Machine | Multiporator ® (Eppendorf, Hamburg, Germany): Exponential decay pulse |
| | ECM830 ® (Genetronics BTX, San Diego, CA, USA): Rectangular pulse |
| Volume of cells | 2-8 × 10⁶/200 µl, |
| | 16 × 10⁶/400 µl, |
| | 32 × 10⁶/800 µl, |
| Electroporation medium | OPTI-MEM ® I (Gibco, Paisley, UK) |
| | OPTI-MIX ® Kit (EquiBio, Ashford, Middlesex, UK) |
| | Isoosomolar electroporation buffer (Eppendorf, Hamburg, DE) |
| Cuvette gap | 0.4 cm |
| Amount of RNA | 5-20 µg/2 × 10⁶ cells |
| Voltage | 200-600 V |
| Pulse Time | up to 500 µs |
| Electroporation temperature | Room temperature |

B. mRNA-Transfection of Mo-DC by electroporation at the µs-range, Influence of voltage on transfection efficiency and viability: More than 90% of the Mo-DC were EGFP+ using a voltage of 400 V and a pulse time of 500 µs (FIG. 25A). Further increasing of the voltage resulted in increasing transgene expression as indicated by increasing mean fluorescence intensity (MFI). Kinetic analysis revealed only a weak decrease of the MFI, even 96 hrs after electroporation. Determination of the cell viability with propidium jodide showed, that the increase of the voltage resulted only in a weak increase of the percentage of dead cells (FIG. 25B). Using a voltage of 600 V even 96 hrs after electroporation the amount of dead cells are only approximately 16%.

C. Influence of pulse form on transfection efficiency and phenotype: Comparison of two electroporation machines delivering exponential decay or rectangular pulse revealed that the form of the pulse has no influence on transfection efficiency when electroporation of Mo-DC were performed in their immature stage (FIG. 26). In comparison with exponential decay pulses delivery of rectangular pulses resulted in a higher transgene expression when electroporation were performed with mature DC. Phenotypical FCM-analysis showed that electroporation of Mo-DC in their immature stage following by addition of the maturation cocktail IL-1β+IL-6+TNF-a+PGE2 resulted in a higher transgene expression in comparison with electroporation of mature Mo-DC (FIG. 27). This effect is shown for a early (CD83) as well as for a late appearing (CD25) surface antigen of mature Mo-DC.

D. Scale-up of the number of cells per electroporation cuvette: In order to determine the maximal cell number per cuvette which can efficiently electroporated, scaling-up experiments were performed. Increasing of the volume of cell suspension resulted in a slightly increase of transgene expression (FIG. 28A). Efficient electroporation were possible up to 32×10⁶ Mo-DC using the maximal volume of 0.8 ml of the 0.4 cm-gap-cuvette. Calculation of the cell number immediately after electroporation showed a recovery of more than 60% (FIG. 28B). Even after a culture time of 24 hrs less amounts of cells were lost.

The invention claimed is:

1. A method for transfection of hematopoietic cells or stem cells with one or more linear polynucleotides, which method comprises electroporation of a suspension containing the hematopoietic cells or stem cells and the linear polynucleotides to be transfected at a capacitance of 100 to below 300 µF.

2. The method of claim 1, wherein
   (i) the pulse is an exponential decay pulse; and/or
   (ii) the electroporation is performed at a voltage from 100 to 500 V; and/or
   (iii) the pulsing time is from 1 to 40 ms.

3. A method for transfection of hematopoietic cells or stem cells with one or more linear polynucleotides, which method comprises electroporation of a suspension containing the hematopoietic cells or stem cells and the linear polynucleotides to be transfected with a soft pulse at 300 to 600 V for 100 us to 1 ms.

4. The method of claim 3, wherein the soft pulse is a square wave pulse or an exponential decay pulse, with 350 to 500 V for 300 to 600 us.

5. The method according to claim 1, wherein
   (i) the concentration of the cells in the suspension is 100 to $1 \times 10^9$ cells per ml, and
   (ii) the linear polynucleotides to be transfected are naked polynucleotides selected from the group consisting of DNA, RNA or DNA-RNA hybrids and mRNA.

6. A method for the transfection of Mo-DC with linear mRNA, which method comprises electroporation of a suspension containing the Mo-DC, and the linear mRNA to be transfected, wherein the transfection is performed at a voltage of 250-300 V, a capacitance below 300 µF and a cell concentration of $1 \times 10^7$ to $4 \times 10^7$ cells/ml.

7. The method according to claim 1, wherein the linear polynucleotides
   (i) encode proteins or peptides to be expressed in the eukaryotic cells, wherein said proteins or peptides may or may not have a function in the cells, the proteins or peptides being selected from the group consisting of tumor antigens, microbial antigens, viral antigens, immunostimulatory or tolerogenic molecules, anti-apoptotic molecules, adhesion and homing molecules and antigen processing molecules; or
   (ii) are functional or regulatory sequences selected from the group consisting of differentiation-regulating genes, differentiation-associated genes and tissue-specific genes.

8. A method for the transfection of human mature Mo-DC with linear mRNA, which method comprises electroporation of a suspension containing the human mature Mo-DC and the linear mRNA to be transfected at a capacitance below 300 µF, wherein the method may further comprise further maturation of the transfected Mo-DC by providing a maturation stimulus.

9. A method for the transfection of human immature Mo-DC with linear mRNA, which method comprises electroporation of a suspension containing the human immature Mo-DC and the linear mRNA to be transfected at a capacitance below 300 µF, wherein the method may further comprise maturation of the transfected Mo-DC by providing a maturation-inducing compound.

10. The method according to claim 9, wherein the maturation-inducing compound comprises one or more of the compounds selected from the group consisting of IL-1β, IL-6, TNF-α, $PGE_2$, lipopolysaccharide, immunostimulatory DNA sequences, CD40 ligand, and poly-I:C.

11. The method of claim 1, wherein the method further comprises cryoconservation of the transfected cells.

12. The method of claim 1, wherein the transfection is performed at a voltage of 250 to 300 V, a capacitance of 150 to 250 µF and a cell concentration of $1 \times 10^7$ to $4 \times 10^7$ cells/ml, at a pulse time of 7 to 10 ms.

13. The method of claim 1, wherein the hematopoietic cells are selected from the group consisting of mononuclear cells, hematopoietic stem cells, marrow CD34+ progenitor derived dendritic cells, CD34+ progenitor derived Langehans cells, and monocyte-derived dendritic cells (Mo-DC).

14. The method of claim 1, wherein the cells are hematopoietic cells.

15. The method according to claim 10, wherein the maturation-inducing compound is a mixture comprising IL-1β, IL-6, TNF-α and $PGE_2$.

16. The method of claim 2, wherein the pulsing time is from 2.5 to 25 ms.

17. The method of claim 2, wherein the pulsing time is from 7 to 10 ms.

* * * * *